United States Patent
Matsumoto et al.

(10) Patent No.: US 9,456,495 B2
(45) Date of Patent: Sep. 27, 2016

(54) NORBORNANE-2-SPIRO-α-CYCLOALKANONE-α'-SPIRO-2"-NORBORNANE-5,5",6,6"-TETRACARBOXYLIC DIANHYDRIDE, NORBORNANE-2-SPIRO-α-CYCLOALKANONE-α'-SPIRO-2"-NORBORNANE-5,5", 6,6"-TETRACARBOXYLIC ACID AND ESTER THEREOF, METHOD FOR PRODUCING NORBORNANE-2-SPIRO-α-CYCLOALKANONE-α'-SPIRO-2"-NORBORNANE-5,5",6,6"-TETRACARBOXYLIC DIANHYDRIDE, POLYIMIDE OBTAINED BY USING THE SAME, AND METHOD FOR PRODUCING POLYIMIDE

(71) Applicants: Toshihiko Matsumoto, Atsugi (JP); Shinichi Komatsu, Tokyo (JP)

(72) Inventors: Toshihiko Matsumoto, Atsugi (JP); Shinichi Komatsu, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 0 days.

(21) Appl. No.: 14/303,317

(22) Filed: Jun. 12, 2014

(65) Prior Publication Data

US 2015/0086753 A1  Mar. 26, 2015

Related U.S. Application Data

(63) Continuation-in-part of application No. 13/578,086, filed on Sep. 26, 2012, now abandoned.

(51) Int. Cl.
    *C08G 73/10* (2006.01)
    *C07D 493/10* (2006.01)
    (Continued)

(52) U.S. Cl.
    CPC ............. *H05K 1/0346* (2013.01); *C07C 67/38* (2013.01); *C07C 69/757* (2013.01);
    (Continued)

(58) Field of Classification Search
    CPC ...................................................... C08G 73/10
    USPC .................. 528/128, 220; 549/237; 560/117; 562/498
    See application file for complete search history.

(56) References Cited

U.S. PATENT DOCUMENTS

| 3,326,940 A | 6/1967 | Dunkel et al. |
| 4,271,079 A | 6/1981 | Maeda et al. |

(Continued)

FOREIGN PATENT DOCUMENTS

| JP | 55-36406 A | 3/1980 |
| JP | 63-057589 A | 3/1988 |

(Continued)

OTHER PUBLICATIONS

Matsomoto et al; Method for production and use of norbornane—and resistance to heat; Aug. 2011; Polytechnic University; Chem Abstract 155:329093.*

(Continued)

*Primary Examiner* — Duc Truong
(74) *Attorney, Agent, or Firm* — Fitch, Even, Tabin & Flannery LLP

(57) ABSTRACT

A norbornane-2-spiro-α-cycloalkanone-α'-spiro-2"-norbornane-5,5",6,6"-tetracarboxylic dianhydride represented by the following general formula (1):

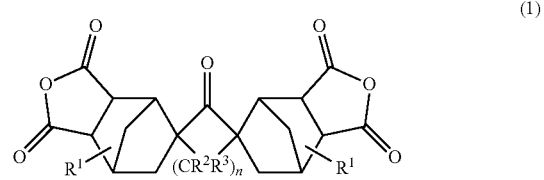

wherein the formula (1), n represents an integer of 0 to 12, and $R^1$s, $R^2$, $R^3$ each independently represents a hydrogen atom or the like.

19 Claims, 27 Drawing Sheets

(51) Int. Cl.
- *C07C 69/757* (2006.01)
- *H05K 1/03* (2006.01)
- *C07C 67/38* (2006.01)
- *C09D 179/08* (2006.01)
- *C07C 235/82* (2006.01)

(52) U.S. Cl.
CPC ......... *C07D 493/10* (2013.01); *C08G 73/105* (2013.01); *C08G 73/1078* (2013.01); *C09D 179/08* (2013.01); *C07C 2103/94* (2013.01); *H05K 1/0393* (2013.01); *H05K 2201/0154* (2013.01); *Y10T 428/24802* (2015.01)

(56) References Cited

U.S. PATENT DOCUMENTS

| | | | |
|---|---|---|---|
| 2009/0182114 | A1 | 7/2009 | Kusaka et al. |
| 2012/0310013 | A1 | 12/2012 | Komatsu et al. |
| 2014/0224313 | A1 | 8/2014 | Wu et al. ............... 136/256 |
| 2014/0224318 | A1 | 8/2014 | Komatsu et al. |
| 2015/0158980 | A1 | 6/2015 | Oka et al. |
| 2015/0218317 | A1 | 8/2015 | Komatsu et al. |
| 2015/0307662 | A1 | 10/2015 | Oka et al. |

FOREIGN PATENT DOCUMENTS

| | | | |
|---|---|---|---|
| JP | 5-271409 A | 10/1993 | |
| JP | 07-304868 A | 11/1995 | |
| JP | 10-310640 A | 11/1998 | |
| JP | 2001-002670 A | 1/2001 | |
| JP | 2002-255955 A | 9/2002 | |
| JP | 2004-018422 A | 1/2004 | |
| JP | 2004-111152 A | 4/2004 | |
| JP | 2005-336246 A | 12/2005 | |
| JP | 2008-31406 A | 2/2008 | |
| JP | 2010-184898 A | 8/2010 | |
| JP | 2011-162479 A | 8/2011 | |
| WO | 2011/099517 A | 8/2011 | |
| WO | WO 2011/099517 A1 | 8/2011 | |
| WO | 2013/021942 A | 2/2013 | |
| WO | WO 2013/021942 A1 | 2/2013 | |
| WO | 2014/034760 A | 3/2014 | |
| WO | WO 2014/034760 A1 | 3/2014 | |

OTHER PUBLICATIONS

Kataoka Shunro, "Engineering Plastics", publisher, Kyoritsu Shuppan Co., Ltd., pp. 88-95,(1987), with English Translation.

Masatoshi Kusama et al., Soluble Polyimides with Polyalicyclic Structure. 3.1 Polyimides from (4arH,8acH)-Decahydro-1t,4t:5c8c-dimethanonaphthalene-2t,3t,6c,7c-tetracarboxylic 2,3:6,7-Dianhydride, Macromolecules, vol. 27, pp. 1117-1123 (1994).

Saishin Poriimido—Kiso to Ouyou—(Current Polyimides—Fundamentals and Applications—), NTS INC., Chapter 1, Alicyclic polyimides, pp. 388-408, (2002), with English Translation.

International Search report dated Mar. 8, 2011, issued against International Application No. PCT/JP2011/052739.

International Preliminary Report on Patentability dated Sep. 27, 2012 issued in PCT/JP2011/052739.

Ryosuke Kimura et al., Japanese Journal of Polymer Science and Technology, 68(3)127-131 (Mar. 25, 2011) with English translation.

Polyimide & Aromatic Polymers Recent Development, pp. 175-183 (Aug. 31, 2013) with English translation.

* cited by examiner

NORBORNANE-2-SPIRO-α-CYCLOALKANONE-α'-SPIRO-2"-NORBORNANE-5,5",6,6"-TETRACARBOXYLIC DIANHYDRIDE, NORBORNANE-2-SPIRO-α-CYCLOALKANONE-α'-SPIRO-2"-NORBORNANE-5,5",6,6"-TETRACARBOXYLIC ACID AND ESTER THEREOF, METHOD FOR PRODUCING NORBORNANE-2-SPIRO-α-CYCLOALKANONE-α'-SPIRO-2"-NORBORNANE-5,5",6,6"-TETRACARBOXYLIC DIANHYDRIDE, POLYIMIDE OBTAINED BY USING THE SAME, AND METHOD FOR PRODUCING POLYIMIDE

CROSS-REFERENCE TO RELATED APPLICATION

This Application is a Continuation-in-Part of U.S. application Ser. No. 13/578,086 having a 371 filing date of Sep. 26, 2012 now ABN (filed on Aug. 9, 2012), which is the U.S. National Stage Application filed under 35 U.S.C. §371 of International Application PCT/JP2011/052739, filed Feb. 9, 2011, designating the United States, and claims priority from Japanese Patent Application 2010-026952, filed Feb. 9, 2010, and Japanese Patent Application 2010-026955, filed Feb. 9, 2010, the complete disclosures of all of the aforesaid applications are hereby incorporated herein by reference in their entirety.

TECHNICAL FIELD

The present invention relates to a norbornane-2-spiro-α-cycloalkanone-α'-spiro-2"-norbornane-5,5",6,6"-tetracarboxylic dianhydride; a norbornane-2-spiro-α-cycloalkanone-α'-spiro-2"-norbornane-5,5",6,6"-tetracarboxylic acid and an ester thereof; a method for producing a norbornane-2-spiro-α-cycloalkanone-α'-spiro-2"-norbornane-5,5",6,6"-tetracarboxylic dianhydride; a polyimide obtained by using the same; and a method for producing the polyimide.

BACKGROUND ART

In general, tetracarboxylic dianhydrides are useful as raw materials for producing polyimide resins, as epoxy curing agents, and as the like. Of these tetracarboxylic dianhydrides, for example, aromatic tetracarboxylic dianhydrides such as pyromellitic dianhydride have mainly been used as raw materials of polyimide resins used in the fields of electronics devices and the like. However, polyimide resins obtained from such aromatic tetracarboxylic dianhydrides are colored due to their aromatic characteristics. Hence, the aromatic tetracarboxylic dianhydrides are not sufficient as raw materials of polyimide resins used in applications in the optical field and the like. In addition, polyimide resins obtained by using such aromatic tetracarboxylic dianhydrides are poorly soluble in solvents, and hence are insufficient in terms of processability thereof. For these reasons, various aliphatic tetracarboxylic dianhydrides have been tested in order to produce a polyimide resin having a high light transmittance and an excellent solubility in solvents.

For example, Japanese Unexamined Patent Application Publication No. Sho 55-36406 (PTL 1) discloses 5-(2,5-dioxotetrahydro-3-furanyl)-3-methyl-3-cyclohexene-1,2-dicarboxylic anhydride. Meanwhile, Japanese Unexamined Patent Application Publication No. Sho 63-57589 (PTL 2) discloses bicyclo[2.2.1]heptane-2,3,5,6-tetracarboxylic dianhydrides. In addition, Japanese Unexamined Patent Application Publication No. Hei 7-304868 (PTL3) discloses bicyclo[2.2.2]octanetetracarboxylic dianhydrides as raw materials of polyimide resins. Moreover, Japanese Unexamined Patent Application Publication No. 2001-2670 (PTL 4) and Japanese Unexamined Patent Application Publication No. 2002-255955 (PTL 5) disclose 1,2-bis(4'-oxa-3',5'-dioxotricyclo[5.2.1.0$^{2,6}$]decan-8'-yloxy)ethane. Moreover, Japanese Unexamined Patent Application Publication No. Hei 10-310640 (PTL 6) discloses bicyclo[2.2.1]heptane-2,3,5-tricarboxyl-5-acetic 2,3:5,5-dianhydride. However, when conventional aliphatic tetracarboxylic dianhydrides as described in PTLs 1 to 6 are used, the obtained polyimide resins are insufficient in terms of heat resistance, and hence insufficient in a practical sense.

Moreover, wholly aromatic polyimide (for example, trade name "Kapton") has been conventionally known as a material necessary for cutting-edge industries for aerospace and aviation applications and the like. Such a wholly aromatic polyimide is synthesized from a combination of an aromatic tetracarboxylic dianhydride and an aromatic diamine by utilizing a reaction represented by the following reaction formula (I):

[Chem. 1]

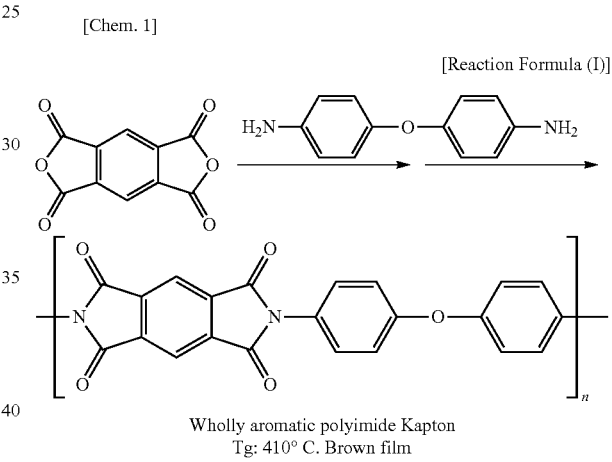

[Reaction Formula (I)]

Wholly aromatic polyimide Kapton
Tg: 410° C. Brown film

The wholly aromatic polyimide is known to exhibit one of the highest levels of heat resistances (glass transition temperature (Tg): 410° C.) among heat resistance polymers (see Engineering plastics, Kyoritsu Shuppan Co., Ltd., 1987, p. 88 (NPL 1)). However, such a wholly aromatic polyimide is colored in brown, because intramolecular charge transfer (CT) occurs between a tetracarboxylic dianhydride unit of an aromatic ring system and a diamine unit of another aromatic ring system. Hence, the wholly aromatic polyimide cannot be used in optical applications and the like, where transparency is necessary. For this reason, in order to produce a polyimide usable in optical applications and the like, research has been conducted on alicyclic polyimides in which no intramolecular CT occurs, and which has a high light transmittance.

There are three kinds of alicyclic polyimides: one is a combination of an alicyclic tetracarboxylic dianhydride and an alicyclic diamine; another is a combination of an alicyclic tetracarboxylic dianhydride and an aromatic diamine; and the other is a combination of an aromatic tetracarboxylic dianhydride and an alicyclic diamine. However, of these alicyclic polyimides, the ones using an alicyclic diamine are difficult to obtain with high molecular weights. This is because an alicyclic diamine has a basicity which is $10^5$ to 10⁶ times greater than that of an aromatic diamine, and hence the polymerization behavior of an alicyclic diamine is totally different from that of an aromatic diamine, so that a salt precipitates during the polymerization. On the other hand, alicyclic polyimides each obtained by combining an alicyclic tetracarboxylic dianhydride and an aromatic diamine can be produced with direct application of general synthetic procedures for the wholly aromatic polyimide, and are easy to obtain with high molecular weights. For this reason, of the alicyclic polyimides, alicyclic polyimides each obtained by combining an alicyclic tetracarboxylic dianhydride and an aromatic diamine have attracted attention in recent years, and investigations have been conducted on alicyclic polyimides using alicyclic tetracarboxylic dianhydrides of a monocyclic ring system, a bicyclic ring system, a tricyclic ring system, a tetracyclic ring system, or a spiro ring system.

For example, as the alicyclic polyimide using an alicyclic tetracarboxylic dianhydride of a tetracyclic ring system, an alicyclic polyimide is known which is obtained from a dimethanonaphthalene-type tetracarboxylic dianhydride by utilizing a reaction represented by the following reaction formula (II) (see Macromolecules, Vol. 27, 1994, p. 1117 (NPL 2)):

[Chem. 2]

[Reaction Formula (II)]

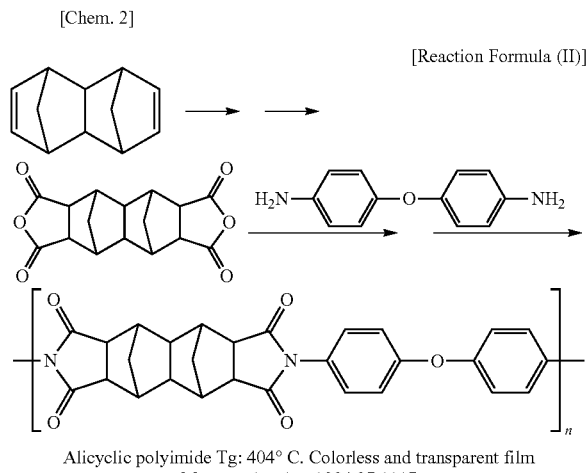

Alicyclic polyimide Tg: 404° C. Colorless and transparent film
Macromolecules, 1994,27,1117

In addition, the alicyclic polyimide obtained from the dimethanonaphthalene-type tetracarboxylic dianhydride is also known to exhibit a heat resistance (glass transition temperature (Tg): 404° C.) close to that of the wholly aromatic polyimide (see SAISHIN PORIIMIDO—KISO TO OUYOU—(Current Polyimides—Fundamentals and Applications—), NTS INC., 2002, Chapter 1, alicyclic polyimides, p. 388 (NPL 3)). However, it has been still impossible to obtain such an alicyclic polyimide having a sufficiently high level of heat resistance comparable to the above-described wholly aromatic polyimide (for example, trade name "Kapton").

CITATION LIST

Patent Literature

[PTL 1] Japanese Unexamined Patent Application Publication No. Sho 55-36406
[PTL 2] Japanese Unexamined Patent Application Publication No. Sho 63-57589
[PTL 3] Japanese Unexamined Patent Application Publication No. Hei 7-304868
[PTL 4] Japanese Unexamined Patent Application Publication No. 2001-2670
[PTL 5] Japanese Unexamined Patent Application Publication No. 2002-255955
[PTL 6] Japanese Unexamined Patent Application Publication No. Hei 10-310640

Non Patent Literature

[NPL 1] Engineering plastics, Kyoritsu Shuppan Co., Ltd., published in 1987, p. 88
[NPL 2] Macromolecules, Vol. 27, published in 1994, p. 1117
[NPL 3] SAISHIN PORIIMIDO—KISO TO OUYOU—(Current polyimides—fundamentals and applications—), NTS INC., 2002, Chapter 1, alicyclic polyimides, p. 388

SUMMARY OF INVENTION

Technical Problem

The present invention has been made in view of the above-described problem of the conventional technologies, and an object of the present invention is to provide a norbornane-2-spiro-α-cycloalkanone-α'-spiro-2"-norbornane-5,5",6,6"-tetracarboxylic dianhydride which can be used as a raw material monomer for producing a polyimide having a high light transmittance, a sufficiently excellent solubility in a solvent, and further a sufficiently high level of heat resistance; a norbornane-2-spiro-α-cycloalkanone-α'-spiro-2"-norbornane-5,5",6,6"-tetracarboxylic acid and an ester thereof which are obtained as intermediates thereof; and a method for producing a norbornane-2-spiro-α-cycloalkanone-α'-spiro-2"-norbornane-5,5",6,6"-tetracarboxylic dianhydride, the method being capable of efficiently and reliably producing a norbornane-2-spiro-α-cycloalkanone-α'-spiro-2"-norbornane-5,5",6,6"-tetracarboxylic dianhydride. In addition, another object of the present invention is to provide a polyimide which can have a high light transmittance and a sufficiently high level of heat resistance, and a method for producing a polyimide capable of efficiently and reliably producing the polyimide.

Solution to Problem

The present inventors have conducted earnest study to achieve the above objects. As a result, the present inventors have found that a norbornane-2-spiro-α-cycloalkanone-α'-spiro-2"-norbornane-5,5",6,6"-tetracarboxylic dianhydride represented by the following general formula (1) makes it possible to produce a polyimide having a high light transmittance, an excellent solubility in a solvent, and further a sufficiently high level of heat resistance. This finding has led to the completion of the present invention. Moreover, the present inventors have found that when a polyimide having a repeating unit represented by the following general formula (4) is produced, the polyimide has a high light transmittance and a sufficiently high level of heat resistance. This finding has lead to the completion of the present invention.

Specifically, first, a norbornane-2-spiro-α-cycloalkanone-α'-spiro-2"-norbornane-5,5",6,6"-tetracarboxylic dianhydride of the present invention is represented by the following general formula (1):

[Chem. 3]

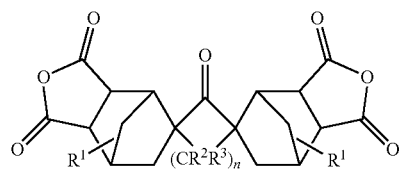

(1)

[in the formula (1), $R^1$s, $R^2$, and $R^3$ each independently represent one selected from the group consisting of a hydrogen atom, alkyl groups having 1 to 10 carbon atoms, and a fluorine atom, and n represents an integer of 0 to 12].

Meanwhile, a norbornane-2-spiro-α-cycloalkanone-α'-spiro-2"-norbornane-5,5",6,6"-tetracarboxylic acid and an ester thereof of the present invention are represented by the following general formula (2):

[Chem. 4]

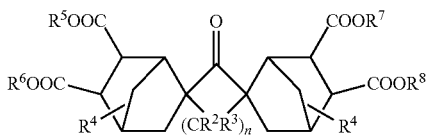

(2)

[in the formula (2), $R^2$, $R^3$, and $R^4$s each independently represent one selected from the group consisting of a hydrogen atom, alkyl groups having 1 to 10 carbon atoms, and a fluorine atom, $R^5$, $R^6$, $R^7$, and $R^8$ each independently represent one selected from the group consisting of a hydrogen atom, alkyl groups having 1 to 10 carbon atoms, cycloalkyl groups having 3 to 10 carbon atoms, alkenyl groups having 2 to 10 carbon atoms, aryl groups having 6 to 20 carbon atoms, and aralkyl groups having 7 to 20 carbon atoms, and n represents an integer of 0 to 12].

Moreover, a method for producing a norbornane-2-spiro-α-cycloalkanone-α'-spiro-2"-norbornane-5,5",6,6"-tetracarboxylic dianhydride of the present invention is a method comprising:

a step of reacting a 5-norbornene-2-spiro-α-cycloalkanone-α'-spiro-2"-5"-norbornene with an alcohol and carbon monoxide in the presence of a palladium catalyst and an oxidizing agent, to thereby obtain at least one compound of norbornane-2-spiro-α-cycloalkanone-α'-spiro-2"-norbornane-5,5",6,6"-tetracarboxylic acids and esters thereof, the 5-norbornene-2-spiro-α-cycloalkanone-α'-spiro-2"-5"-norbornene being represented by the following general formula (3):

[Chem. 5]

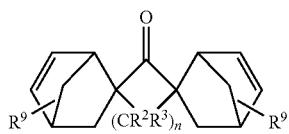

(3)

[in the formula (3), $R^2$, $R^3$, and $R^9$s each independently represent one selected from the group consisting of a hydrogen atom, alkyl groups having 1 to 10 carbon atoms, and a fluorine atom, and n represents an integer of 0 to 12], the norbornane-2-spiro-α-cycloalkanone-α'-spiro-2"-norbornane-5,5",6,6"-tetracarboxylic acids and esters thereof being represented by the following general formula (2):

[Chem. 6]

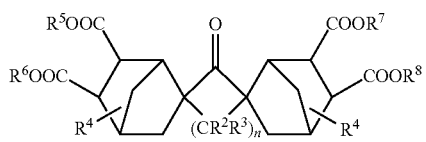

(2)

[in the formula (2), $R^2$, $R^3$, and $R^4$s each independently represent one selected from the group consisting of a hydrogen atom, alkyl groups having 1 to 10 carbon atoms, and a fluorine atom, $R^5$, $R^6$, $R^7$, and $R^8$ each independently represent one selected from the group consisting of a hydrogen atom, alkyl groups having 1 to 10 carbon atoms, cycloalkyl groups having 3 to 10 carbon atoms, alkenyl groups having 2 to 10 carbon atoms, aryl groups having 6 to 20 carbon atoms, and aralkyl groups having 7 to 20 carbon atoms, and n represents an integer of 0 to 12]; and a step of obtaining a norbornane-2-spiro-α-cycloalkanone-α'-spiro-2"-norbornane-5,5",6,6"-tetracarboxylic dianhydride from the compound by using formic acid, an acid catalyst, and acetic anhydride, the norbornane-2-spiro-α-cycloalkanone-α'-spiro-2"-norbornane-5,5",6,6"-tetracarboxylic dianhydride being represented by the following general formula (1):

[Chem. 7]

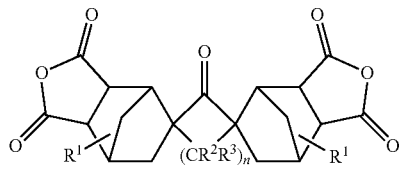

(1)

[in the formula (1), $R^1$s, $R^2$, and $R^3$ each independently represent one selected from the group consisting of a hydrogen atom, alkyl groups having 1 to 10 carbon atoms, and a fluorine atom, and n represents an integer of 0 to 12].

A polyimide of the present invention comprises a repeating unit represented by the following general formula (4):

[Chem. 8]

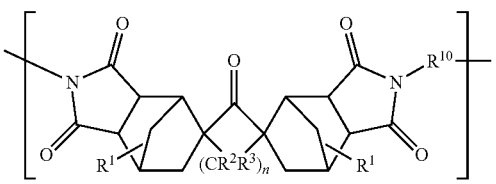

(4)

[in the formula (4), $R^1$s, $R^2$, and $R^3$ each independently represent one selected from the group consisting of a hydrogen atom, alkyl groups having 1 to 10 carbon atoms, and a fluorine atom, $R^{10}$ represents an aryl group having 6 to 40 carbon atoms, and n represents an integer of 0 to 12].

Note that, although it is not exactly clear why the polyimide having the repeating unit represented by the general formula (4) exhibits a sufficiently high level of heat resistance, the present inventors speculate as follows. Specifically, the repeating unit has a structure which has a ketone group being capable of improving the heat resistance of the polyimide and being a polar group not inhibiting the polymerization reaction, and which has no active α hydrogen remaining on carbon atoms adjacent to the ketone group. Hence, the polyimide has a chemically efficiently stable structure, so that the sufficiently high level of heat resistance is achieved.

In addition, the polyamic acid of the present invention comprises a repeating unit represented by the following general formula (9):

[Chem. 9]

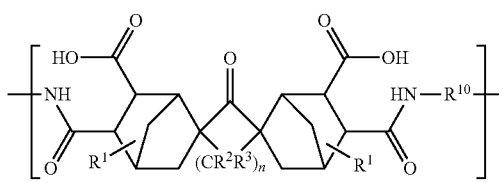
(9)

[in the formula (9), $R^1$s, $R^2$, and $R^3$ each independently represent one selected from the group consisting of a hydrogen atom, alkyl groups having 1 to 10 carbon atoms, and a fluorine atom, $R^{10}$ represents an aryl group having 6 to 40 carbon atoms, and n represents an integer of 0 to 12].

Note that the polyamic acid can be obtained as a reaction intermediate when the polyimide of the present invention is produced. In addition, the polyamic acid is preferably such that the polyamic acid has an intrinsic viscosity [η] of 0.05 to 3.0 dL/g, the intrinsic viscosity [η] being measured with a kinematic viscometer under a temperature condition of 30° C. by using a solution of the polyamic acid at a concentration of 0.5 g/dL obtained by dissolving the polyamic acid in N,N-dimethylacetamide.

In addition, in each of the polyimide of the present invention and the polyamic acid of the present invention, $R^{10}$ is preferably at least one of groups represented by the following general formulae (5) to (8):

[Chem. 10]

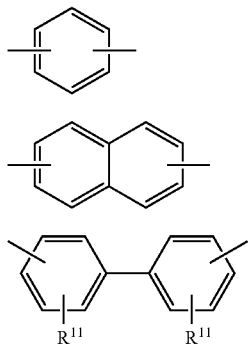

(5)

(6)

(7)

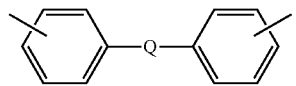
(8)

[in the formula (7), $R^{11}$s represent one selected from the group consisting of a hydrogen atom, a fluorine atom, a methyl group, an ethyl group, and a trifluoromethyl group, and in the formula (8), Q represents one selected from the group consisting of groups represented by the formulae: —O—, —S—, —CO—, —CONH—, —SO$_2$—, —C(CF$_3$)$_2$—, —C(CH$_3$)$_2$—, —CH$_2$—, —O—C$_6$H$_4$—C(CH$_3$)$_2$—C$_6$H$_4$—O—, —O—C$_6$H$_4$—SO$_2$—C$_6$H$_4$—O—, —C(CH$_3$)$_2$—C$_6$H$_4$—C(CH$_3$)$_2$—, —O—C$_6$H$_4$—C$_6$H$_4$—O—, and —O—C$_6$H$_4$—O—].

A method for producing a polyimide of the present invention is a method comprising:

a step of reacting a norbornane-2-spiro-α-cycloalkanone-α'-spiro-2"-norbornane-5,5",6,6"-tetracarboxylic dianhydride with an aromatic diamine in the presence of an organic solvent, to thereby obtain a polyamic acid, the norbornane-2-spiro-α-cycloalkanone-α'-spiro-2"-norbornane-5,5",6,6"-tetracarboxylic dianhydride being represented by the following general formula (1):

[Chem. 11]

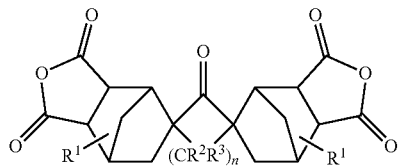
(1)

[in the formula (1), $R^1$s, $R^2$, and $R^3$ each independently represent one selected from the group consisting of a hydrogen atom, alkyl groups having 1 to 10 carbon atoms, and a fluorine atom, and n represents an integer of 0 to 12], the aromatic diamine being represented by the following general formula (10):

[Chem. 12]

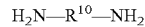

H$_2$N—R$^{10}$—NH$_2$  (10)

[in the formula (10), $R^{10}$ represents an aryl group having 6 to 40 carbon atoms], the polyamic acid having a repeating unit represented by the following general formula (9):

[Chem. 13]

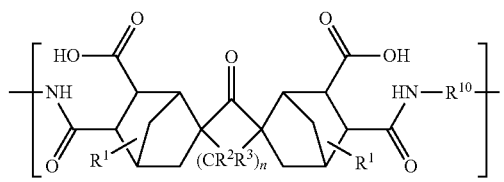
(9)

[in the formula (9), $R^1$s, $R^2$, and $R^3$ each independently represent one selected from the group consisting of a hydrogen atom, alkyl groups having 1 to 10 carbon atoms, and a fluorine atom, $R^{10}$ represents an aryl group having 6 to 40 carbon atoms, and n represents an integer of 0 to 12]; and a step of subjecting the polyamic acid to imidization, to thereby obtain a polyimide having a repeating unit represented by the following general formula (4):

[Chem. 14]

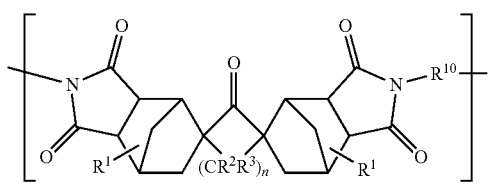

(4)

[in the formula (4), $R^1$s, $R^2$, and $R^3$ each independently represent one selected from the group consisting of a hydrogen atom, alkyl groups having 1 to 10 carbon atoms, and a fluorine atom, $R^{10}$ represents an aryl group having 6 to 40 carbon atoms, and n represents an integer of 0 to 12].

A film of the present invention comprises the above-described polyimide of the present invention.

A flexible printed wiring board of the present invention comprises the above-described polyimide of the present invention.

A liquid crystal orientation film of the present invention comprises the above-described polyimide of the present invention.

A transparent electrode substrate of the present invention comprises the above-described polyimide of the present invention.

A transparent electrode substrate of an organic EL of the present invention comprises the above-described polyimide of the present invention.

A transparent electrode substrate of a solar cell of the present invention comprises the above-described polyimide of the present invention.

A transparent electrode substrate of an electronic paper of the present invention comprises the above-described polyimide of the present invention.

A heat resistant insulating tape of the present invention comprises the above-described polyimide of the present invention.

An enamel for a wire of the present invention comprises the above-described polyimide of the present invention.

A protective coating of a semiconductor of the present invention comprises the above-described polyimide of the present invention.

A transfer belt of the present invention comprises the above-described polyimide of the present invention.

An interlayer dielectric film of the present invention comprises the above-described polyimide of the present invention.

A substrate for a sensor of the present invention comprises the above-described polyimide of the present invention.

A solution of the present invention comprises the above-described polyamic acid of the present invention, and an organic solvent.

Advantageous Effects of Invention

According to the present invention, it is possible to provide a norbornane-2-spiro-α-cycloalkanone-α'-spiro-2''-norbornane-5,5'',6,6''-tetracarboxylic dianhydride which can be used as a raw material monomer for producing a polyimide having a high light transmittance, a sufficiently excellent solubility in a solvent, and further a sufficiently high level of heat resistance; a norbornane-2-spiro-α-cycloalkanone-α'-spiro-2''-norbornane-5,5'',6,6''-tetracarboxylic acid and an ester thereof which are obtained as intermediates thereof; and a method for producing a norbornane-2-spiro-α-cycloalkanone-α'-spiro-2''-norbornane-5,5'',6,6''-tetracarboxylic dianhydride, the method being capable of efficiently and reliably producing a norbornane-2-spiro-α-cycloalkanone-α'-spiro-2''-norbornane-5,5'',6,6''-tetracarboxylic dianhydride.

In addition, according to the present invention, it is possible to provide a polyimide which can have a high light transmittance and a sufficiently high level of heat resistance, and a method for producing a polyimide capable of efficiently and reliably producing the polyimide.

DESCRIPTION OF EMBODIMENTS

Figure 1:
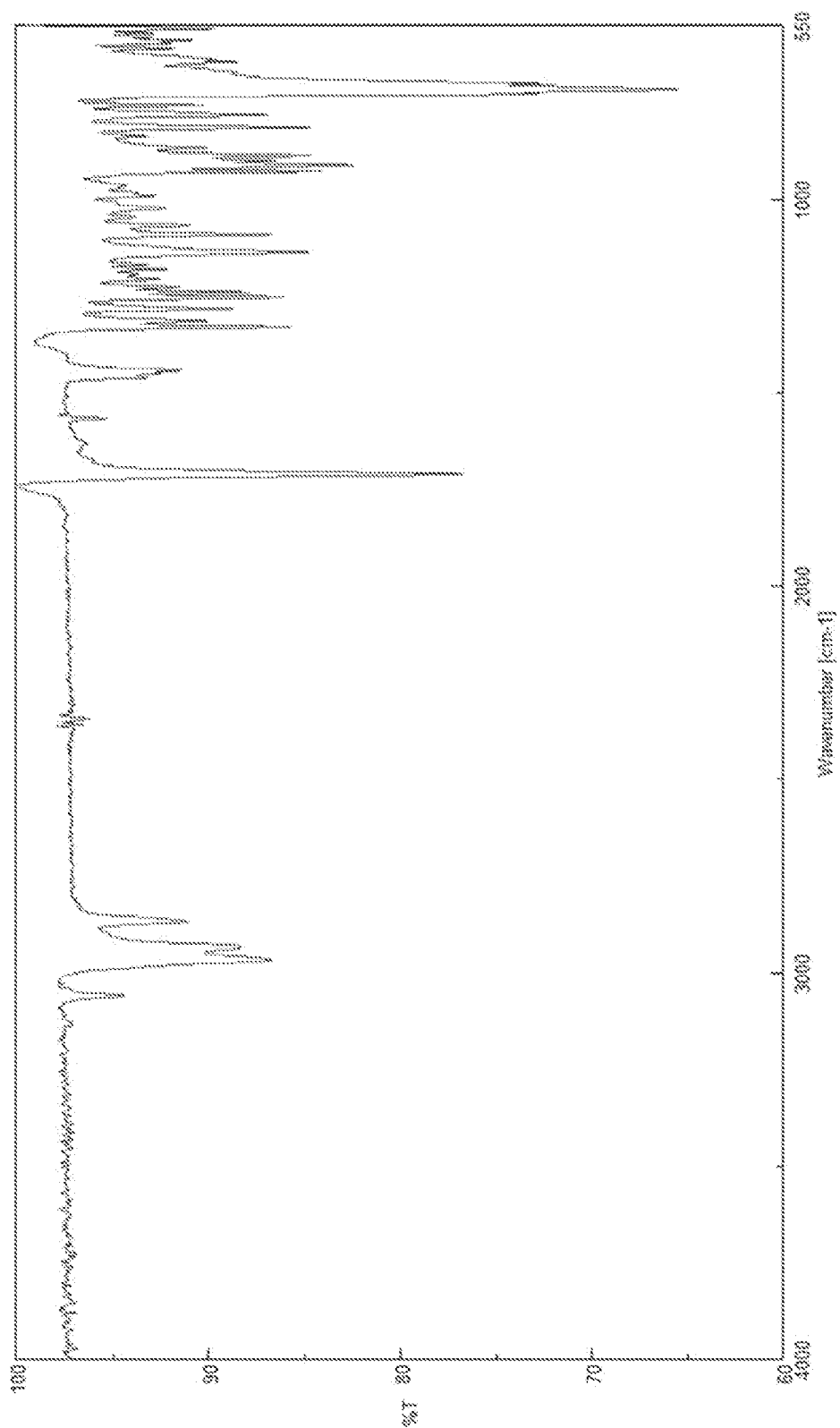
FIG. 1 is a graph showing an IR spectrum of 5-norbornene-2-spiro-α-cyclopentanone-α'-spiro-2''-5''-norbornene obtained in Synthesis Example 1.

Hereinafter, the present invention will be described in detail based on preferred embodiments thereof.

First, a norbornane-2-spiro-α-cycloalkanone-α'-spiro-2"-norbornane-5,5",6,6"-tetracarboxylic dianhydride of the present invention is described. Specifically, the norbornane-2-spiro-α-cycloalkanone-α'-spiro-2"-norbornane-5,5",6,6"-tetracarboxylic dianhydride of the present invention is represented by the following general formula (1):

[Chem. 15]

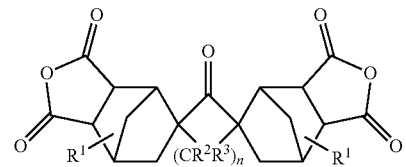

[in the formula (1), R$^1$s, R$^2$, and R$^3$ each independently represent one selected from the group consisting of a hydrogen atom, alkyl groups having 1 to 10 carbon atoms, and a fluorine atom, and n represents an integer of 0 to 12].

The alkyl group which can be selected as each R$^1$ in the general formula (1) is an alkyl group having 1 to 10 carbon atoms. If the number of carbon atoms exceeds 10, the heat resistance of a polyimide obtained in the case of use as a monomer for the polyimide is lowered. In addition, the number of carbon atoms of the alkyl group which can be selected as R$^1$ is preferably 1 to 6, more preferably 1 to 5, further preferably 1 to 4, and particularly preferably 1 to 3, from the viewpoint that a higher level of heat resistance is obtained when a polyimide is produced. In addition, the alkyl group which can be selected as R$^1$ may be linear or branched.

R$^1$s in the general formula (1) are more preferably each independently a hydrogen atom or an alkyl group having 1 to 10 carbon atoms, from the viewpoint that a higher level of heat resistance is obtained when a polyimide is produced. Of these, each R$^1$ is more preferably a hydrogen atom, a methyl group, an ethyl group, a n-propyl group, or an isopropyl group, and particularly preferably a hydrogen atom or a methyl group, from the viewpoints that raw materials are readily available, and that the purification is easier. In addition, the plural R$^1$s in the formula are particularly preferably the same, from the viewpoints of ease of purification and the like.

In addition, n in the general formula (1) represents an integer of 0 to 12. If the value of n exceeds the upper limit, it becomes difficult to purify the norbornane-2-spiro-α-cycloalkanone-α'-spiro-2"-norbornane-5,5",6,6"-tetracarboxylic dianhydride. In addition, an upper limit value of the numeric value range of n in the general formula (1) is more preferably 5, and particularly preferably 3, from the viewpoint that the purification becomes easier. In addition, a lower limit value of the numeric value range of n in the general formula (1) is more preferably 1, and particularly preferably 2, from the viewpoints of the stability of raw materials and the like. Accordingly, n in the general formula (1) is particularly preferably an integer of 2 to 3.

Meanwhile, the alkyl groups having 1 to 10 carbon atoms which can be selected as R$^2$ or R$^3$ in the general formula (1) are the same as the alkyl groups having 1 to 10 carbon atoms which can be selected as R$^1$. Of these substituents, the substituent which can be selected as R$^2$ or R$^3$ is preferably a hydrogen atom, or an alkyl group having 1 to 10 (preferably 1 to 6, more preferably 1 to 5, further preferably 1 to 4, and particularly preferably 1 to 3) carbon atoms, and is particularly preferably a hydrogen atom or a methyl group, from the viewpoint of ease of purification.

In addition, examples of the norbornane-2-spiro-α-cycloalkanone-α'-spiro-2"-norbornane-5,5",6,6"-tetracarboxylic dianhydride represented by the general formula (1) include norbornane-2-spiro-α-cyclopentanone-α'-spiro-2"-norbornane-5,5",6,6"-tetracarboxylic dianhydride (also referred to as "norbornane-2-spiro-2'-cyclopentanone-5'- spiro-2"-norbornane-5,5",6,6"-tetracarboxylic dianhydride"), methylnorbornane-2-spiro-α-cyclopentanone-α'-spiro-2"-(methylnorbornane)-5,5",6,6"-tetracarboxylic dianhydride, norbornane-2-spiro-α-cyclohexanone-α'-spiro-2"-norbornane-5,5",6,6"-tetracarboxylic dianhydride (also referred to as "norbornane-2-spiro-2'-cyclohexanone-6'-spiro-2"-norbornane-5,5",6,6"-tetracarboxylic dianhydride"), methylnorbornane-2-spiro-α-cyclohexanone-α'-spiro-2"-(methylnorbornane)-5,5",6,6"-tetracarboxylic dianhydride, norbornane-2-spiro-α-cyclopropanone-α'-spiro-2"-norbornane-5,5",6,6"-tetracarboxylic dianhydride, norbornane-2-spiro-α-cyclobutanone-α'-spiro-2"-norbornane-5,5",6,6"-tetracarboxylic dianhydride, norbornane-2-spiro-α-cycloheptanone-α'-spiro-2"-norbornane-5,5",6,6"-tetracarboxylic dianhydride, norbornane-2-spiro-α-cyclooctanone-α'-spiro-2"-norbornane-5,5",6,6"-tetracarboxylic dianhydride, norbornane-2-spiro-α-cyclononanone-α'-spiro-2"-norbornane-5,5",6,6"-tetracarboxylic dianhydride, norbornane-2-spiro-α-cyclodecanone-α'-spiro-2"-norbornane-5,5",6,6"-tetracarboxylic dianhydride, norbornane-2-spiro-α-cycloundecanone-α'-spiro-2"-norbornane-5,5",6,6"-tetracarboxylic dianhydride, norbornane-2-spiro-α-cyclododecanone-α'-spiro-2"-norbornane-5,5",6,6"-tetracarboxylic dianhydride, norbornane-2-spiro-α-cyclotridecanone-α'-spiro-2"-norbornane-5,5",6,6"-tetracarboxylic dianhydride, norbornane-2-spiro-α-cyclotetradecanone-α'-spiro-2"-norbornane-5,5",6,6"-tetracarboxylic dianhydride, norbornane-2-spiro-α-cyclopentadecanone-α'-spiro-2"-norbornane-5,5",6,6"-tetracarboxylic dianhydride, norbornane-2-spiro-α-(methylcyclopentanone)-α'-spiro-2"-norbornane-5,5",6,6"-tetracarboxylic dianhydride, norbornane-2-spiro-α-(methylcyclohexanone)-α'-spiro-2"-norbornane-5,5",6,6"-tetracarboxylic dianhydride, and the like.

Next, a norbornane-2-spiro-α-cycloalkanone-α'-spiro-2"-norbornane-5,5",6,6"-tetracarboxylic acid and an ester thereof of the present invention are described. The norbornane-2-spiro-α-cycloalkanone-α'-spiro-2"-norbornane-5,5",6,6"-tetracarboxylic acid and the ester thereof of the present invention are represented by the following general formula (2):

[Chem. 16]

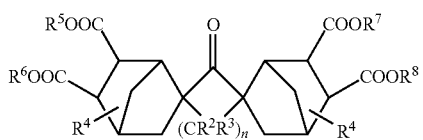

(2)

[in the formula (2), $R^2$, $R^3$, and $R^4$s each independently represent one selected from the group consisting of a hydrogen atom, alkyl groups having 1 to 10 carbon atoms, and a fluorine atom, $R^5$, $R^6$, $R^7$, and $R^8$ each independently represent one selected from the group consisting of a hydrogen atom, alkyl groups having 1 to 10 carbon atoms, cycloalkyl groups having 3 to 10 carbon atoms, alkenyl groups having 2 to 10 carbon atoms, aryl groups having 6 to 20 carbon atoms, and aralkyl groups having 7 to 20 carbon atoms, and n represents an integer of 0 to 12].

$R^4$s in the general formula (2) are the same as those for $R^1$s in the general formula (1), and preferred examples thereof are also the same as those of $R^1$s in the general formula (1). In addition, $R^2$ and $R^3$ in the general formula (2) are the same as those for $R^2$ and $R^3$ in the general formula (1), and preferred examples thereof are also the same as those of $R^2$ and $R^3$ in the general formula (1). Moreover, n in the general formula (2) is the same integer as that for n in the general formula (1), and preferred values thereof are also the same as those of n in the general formula (1).

In addition, the alkyl group which can be selected as $R^5$, $R^6$, $R^7$, or $R^8$ in the general formula (2) is an alkyl group having 1 to 10 carbon atoms. If the number of carbon atoms of the alkyl group exceeds 10, the purification becomes difficult. In addition, the number of carbon atoms of the alkyl group which can be selected as $R^5$, $R^6$, $R^7$, or $R^8$ is more preferably 1 to 5, and further preferably 1 to 3, from the viewpoint that the purification becomes easier. In addition, the alkyl group which can be selected as $R^5$, $R^6$, $R^7$, or $R^8$ may be linear or branched.

Meanwhile, the cycloalkyl group which can be selected as $R^5$, $R^6$, $R^7$, or $R^8$ in the general formula (2) is a cycloalkyl group having 3 to 10 carbon atoms. If the number of carbon atoms of the cycloalkyl group exceeds 10, the purification becomes difficult. In addition, the number of carbon atoms of the cycloalkyl group which can be selected as $R^5$, $R^6$, $R^7$, or $R^8$ is more preferably 3 to 8, and further preferably 5 to 6, from the viewpoint that the purification becomes easier.

In addition, the alkenyl group which can be selected as $R^5$, $R^6$, $R^7$, or $R^8$ in the general formula (2) is an alkenyl group having 2 to 10 carbon atoms. If the number of carbon atoms of the alkenyl group exceeds 10, the purification becomes difficult. In addition, the number of carbon atoms of the alkenyl group which can be selected as $R^5$, $R^6$, $R^7$, or $R^8$ is more preferably 2 to 5, and further preferably 2 to 3, from the viewpoint that the purification becomes easier.

Moreover, the aryl group which can be selected as $R^5$, $R^6$, $R^7$, or $R^8$ in the general formula (2) is an aryl group having 6 to 20 carbon atoms. If the number of carbon atoms of the aryl group exceeds 20, the purification becomes difficult. In addition, the number of carbon atoms of the aryl group which can be selected as $R^5$, $R^6$, $R^7$, or $R^8$ is more preferably 6 to 10, and further preferably 6 to 8, from the viewpoint that the purification becomes easier.

In addition, the aralkyl group which can be selected as $R^5$, $R^6$, $R^7$, or $R^8$ in the general formula (2) is an aralkyl group having 7 to 20 carbon atoms. If the number of carbon atoms of the aralkyl group exceeds 20, the purification becomes difficult. In addition, the number of carbon atoms of the aralkyl group which can be selected as $R^5$, $R^6$, $R^7$, or $R^8$ is more preferably 7 to 10, and further preferably 7 to 9, from the viewpoint that the purification becomes easier.

Moreover, $R^5$, $R^6$, $R^7$, and $R^8$ in the general formula (2) are each independently preferably a hydrogen atom, a methyl group, an ethyl group, a n-propyl group, an isopropyl group, a n-butyl group, an isobutyl group, sec-butyl, t-butyl, an 2-ethylhexyl group, a cyclohexyl group, an allyl group, a phenyl group, or a benzyl group, and particularly preferably a methyl group, from the viewpoint that the purification becomes easier. Note that $R^5$, $R^6$, $R^7$, and $R^8$ in the general formula (2) may be the same or different. However, $R^5$, $R^6$, $R^7$, and $R^8$ are more preferably the same, from the viewpoint of synthesis.

Examples of the norbornane-2-spiro-α-cycloalkanone-α'-spiro-2"-norbornane-5,5",6,6"-tetracarboxylic acid and the ester thereof represented by the general formula (2) include norbornane-2-spiro-α-cyclopentanone-α'-spiro-2"-norbornane-5,5",6,6"-tetracarboxylic acid tetramethyl ester, norbornane-2-spiro-α-cyclopentanone-α'-spiro-2"-norbornane-5,5",6,6"-tetracarboxylic acid tetraethyl ester, norbornane- 2-spiro-α-cyclopentanone-α'-spiro-2"-norbornane-5,5",6,6"-tetracarboxylic acid tetrapropyl ester, norbornane-2-spiro-α-cyclopentanone-α'-spiro-2"-norbornane-5,5",6,6"-tetracarboxylic acid tetrabutyl ester, norbornane-2-spiro-α-cyclopentanone-α'-spiro-2"-norbornane-5,5",6,6"-tetracarboxylic acid tetra(2-ethylhexyl) ester, norbornane-2-spiro-α-cyclopentanone-α'-spiro-2"-norbornane-5,5",6,6"-tetracarboxylic acid tetraallyl ester, norbornane-2-spiro-α-cyclopentanone-α'-spiro-2"-norbornane-5,5",6,6"-tetracarboxylic acid tetracyclohexyl ester, norbornane-2-spiro-α-cyclopentanone-α'-spiro-2"-norbornane-5,5",6,6"-tetracarboxylic acid tetraphenyl ester, norbornane-2-spiro-α-cyclopentanone-α'-spiro-2"-norbornane-5,5",6,6"-tetracarboxylic acid tetrabenzyl ester, norbornane-2-spiro-α-cyclopentanone-α'-spiro-2"-norbornane-5,5",6,6"-tetracarboxylic acid, methylnorbornane-2-Spiro-α-cyclopentanone-α'-spiro-2"-(methylnorbornane)-5,5",6,6"-tetracarboxylic acid tetramethyl ester, norbornane-2-spiro-α-cyclohexanone-α'-spiro-2"-norbornane-5,5",6,6"-tetracarboxylic ac id tetramethyl ester, norbornane-2-spiro-α-cyclohexanone-α'-spiro-2"-norbornane-5,5",6,6"-tetracarboxylic acid tetraethyl ester, norbornane-2-spiro-α-cyclohexanone-α'-spiro-2"-norbornane-5,5",6,6"-tetracarboxylic acid tetrapropyl ester, norbornane-2-spiro-α-cyclohexanone-α'-spiro-2"-norbornane-5,5",6,6"-tetracarboxylic acid tetrabutyl ester, norbornane-2-spiro-α-cyclohexanone-α'-spiro-2"-norbornane-5,5",6,6"-tetracarboxylic acid tetra(2-ethylhexyl) ester, norbornane-2-spiro-α-cyclohexanone-α'-spiro-2"-norbornane-5,5",6,6"-tetracarboxylic acid tetraallyl ester, norbornane-2-spiro-α-cyclohexanone-α'-spiro-2"-norbornane-5,5",6,6"-tetracarboxylic acid tetracyclohexyl ester, norbornane-2-spiro-α-cyclohexanone-α'-spiro-2"-norbornane-5,5",6,6"-tetracarboxylic acid tetraphenyl ester, norbornane-2-spiro-α-cyclohexanone-α'-spiro-2"-norbornane-5,5",6,6"-tetracarboxylic acid tetrabenzyl ester, norbornane-2-spiro-α-cyclohexanone-α'-spiro-2"-norbornane-5,5",6,6"-tetracarboxylic acid, methylnorbornane-2-spiro-α-cyclohexanone-α'-spiro-2"-(methylnorbornane)-5,5",6,6"-tetracarboxylic acid tetramethyl ester, norbornane-2-spiro-α-cyclopropanone-α'-spiro-2"-norbornane-5,5",6,6"-tetracarboxylic acid tetramethyl ester, norbornane-2-spiro-α-cyclobutanone-α'-spiro-2"-norbornane-5,5",6,6"-tetracarboxylic acid tetramethyl ester, norbornane-2-spiro-α-cycloheptanone-α'-spiro-2"-norbornane-5,5",6,6"-tetracarboxylic acid tetramethyl ester, norbornane-2-spiro-α-cyclooctanone-α'-spiro-2"-norbornane-5,5",6,6"-tetracarboxylic acid tetramethyl ester, norbornane-2-spiro-α-cyclononanone-α'-spiro-2"-norbornane-5,5",6,6"-tetracarboxylic acid tetramethyl ester, norbornane-2-spiro-α-cyclodecanone-α'-spiro-2"-norbornane-5,5",6,6"-tetracarboxylic acid tetramethyl ester, norbornane-2-spiro-α-cycloundecanone-α'-spiro-2"-norbornane-5,5",6,6"-tetracarboxylic acid tetramethyl ester, norbornane-2-spiro-α-cyclododecanone-α'-spiro-2"-norbornane-5,5",6,6"-tetracarboxylic acid tetramethyl ester, norbornane-2-spiro-α-cyclotridecanone-α'-spiro-2"-norbornane-5,5",6,6"-tetracarboxylic acid tetramethyl ester, norbornane-2-spiro-α-cyclotetradecanone-α'-spiro-2"-norbornane-5,5",6,6"-tetracarboxylic acid tetramethyl ester, norbornane-2-spiro-α-cyclopentadecanone-α'-spiro-2"-norbornane-5,5",6,6"-tetracarboxylic acid tetramethyl ester, norbornane-2-spiro-α-cyclopentanone-α'-spiro-2"-norbornane-5,5",6,6"-tetracarboxylic acid, norbornane-2-spiro-α-cyclohexanone-α'-spiro-2"-norbornane-5,5",6,6"-tetracarboxylic acid, and the like.

Next, a description is given of a method for producing a norbornane-2-spiro-α-cycloalkanone-α'-spiro-2"-norbornane-5,5",6,6"-tetracarboxylic dianhydride of the present invention, which can be preferably employed for producing the above-described norbornane-2-spiro-α-cycloalkanone-α'-spiro-2"-norbornane-5,5",6,6"-tetracarboxylic dianhydride of the present invention. Note that, in the method for producing a norbornane-2-spiro-α-cycloalkanone-α'-spiro-2"-norbornane-5,5",6,6"-tetracarboxylic dianhydride of the present invention, the above-described norbornane-2-spiro-α-cycloalkanone-α'-spiro-2"-norbornane-5,5",6,6"-tetracarboxylic acid and the ester thereof represented by the general formula (2) of the present invention can be obtained as intermediates during the production.

The method for producing a norbornane-2-spiro-α-cycloalkanone-α'-spiro-2"-norbornane-5,5",6,6"-tetracarboxylic dianhydride of the present invention is a method comprising:

a step (first step) of reacting a 5-norbornene-2-spiro-α-cycloalkanone-α'-spiro-2"-5"-norbornene with an alcohol and carbon monoxide in the presence of a palladium catalyst and an oxidizing agent, to thereby obtain at least one compound of norbornane-2-spiro-α-cycloalkanone-α'-spiro-2"-norbornane-5,5",6,6"-tetracarboxylic acids and esters thereof represented by the above-described general formula (2), the 5-norbornene-2-spiro-α-cycloalkanone-α'-spiro-2"-5"-norbornene being represented by the following general formula (3):

[Chem. 17]

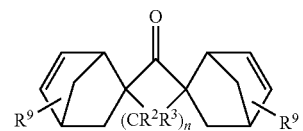

(3)

[in the formula (3), $R^2$, $R^3$, and $R^9$s each independently represent one selected from the group consisting of a hydrogen atom, alkyl groups having 1 to 10 carbon atoms, and a fluorine atom, and n represents an integer of 0 to 12]; and a step (second step) of obtaining a norbornane-2-spiro-α-cycloalkanone-α'-spiro-2"-norbornane-5,5",6,6"-tetracarboxylic dianhydride represented by the above-described general formula (1) from the compound by using formic acid, an acid catalyst, and acetic anhydride. The first step and the second step are described separately below.

The first step is a step of reacting a 5-norbornene-2-spiro-α-cycloalkanone-α'-spiro-2"-5"-norbornene represented by the above-described general formula (3) (hereinafter simply referred to as a "compound represented by the general formula (3)" in some cases) with an alcohol and carbon monoxide, to thereby obtain the norbornane-2-spiro-α-cycloalkanone-α'-spiro-2"-norbornane-5,5",6,6"-tetracarboxylic acid and the ester thereof represented by the general formula (2) (hereinafter simply referred to as "compound represented by the general formula (2)" in some cases).

In the 5-norbornene-2-spiro-α-cycloalkanone-α'-spiro-2"-5"-norbornene represented by the general formula (3) and used in the first step, $R^9$ s in the general formula (3) is the same as those for $R^1$s in the general formula (1), and preferred examples thereof are also the same as those of $R^1$s in the general formula (1). In addition, $R^2$ and $R^3$ in the general formula (3) are the same as those for $R^2$ and $R^3$ in the general formula (1), and preferred examples thereof are also the same as those of $R^2$ and $R^3$ in the general formula (1). Moreover, n in the general formula (3) is the same integer as that for n in the general formula (1), and preferred values thereof are also the same as those of n in the general formula (1).

Examples of the compound represented by the general formula (3) include 5-norbornene-2-spiro-α-cyclopentanone-α'-spiro-2''-5''-norbornene (also referred to as "5-norbornene-2-spiro-2'-cyclopentanone-5'-spiro-2''-5''-norbornene"), methyl-5-norbornene-2-spiro-α-cyclopentanone-α'-spiro-2''-(methyl-5''-norbornene), 5-norbornene-2-spiro-α-cyclohexanone-α'-spiro-2''-5''-norbornene (also referred to as "5-norbornene-2-spiro-2'-cyclohexanone-6'-spiro-2''-5''-norbornene"), methyl-5-norbornene-2-spiro-α-cyclohexanone-α'-spiro-2''-(methyl-5''-norbornene), 5-norbornene-2-spiro-α-cyclopropanone-α'-spiro-2''-5''-norbornene, 5-norbornene-2-spiro-α-cyclobutanone-α'-spiro-2''-5''-norbornene, 5-norbornene-2-spiro-α-cycloheptanone-α'-spiro-2''-5''-norbornene, 5-norbornene-2-spiro-α-cyclooctanone-α'-spiro-2''-5''-norbornene, 5-norbornene-2-spiro-α-cyclononanone-α'-spiro-2''-5''-norbornene, 5-norbornene-2-spiro-α-cyclodecanone-α'-spiro-2''-5''-norbornene, 5-norbornene-2-spiro-α-cycloundecanone-α'-spiro-2''-5''-norbornene, 5-norbornene-2-spiro-α-cyclododecanone-α'-spiro-2''-5''-norbornene, 5-norbornene-2-spiro-α-cyclotridecanone-α'-spiro-2''-5''-norbornene, 5-norbornene-2-spiro-α-cyclotetradecanone-α'-spiro-2''-5''-norbornene, 5-norbornene-2-spiro-α-cyclopentadecanone-α'-spiro-2''-5''-norbornene, 5-norbornene-2-spiro-α-(methylcyclopentanone)-α'-spiro-2''-5''-norbornene, 5-norbornene-2-spiro-α-(methylcyclohexanone)-α'-spiro-2''-5''-norbornene, and the like.

In addition, a method for producing the compound represented by the general formula (3) is not particularly limited, and, as the method, for example, a method can be employed in which the compound represented by the general formula (3) is produced by utilizing a reaction represented by the following reaction formula (III):

[Chem. 18]

[Reaction Formula (III)]

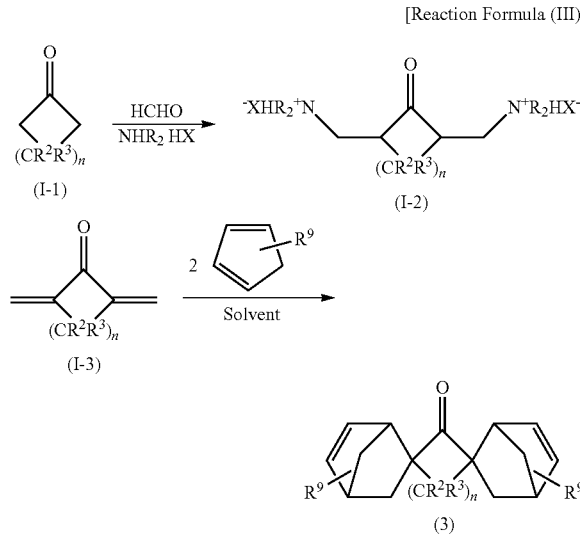

[in the reaction formula (III), n, $R^2$, and $R^3$ have the same meanings as those of n, $R^2$, and $R^3$ in the general formula (1); $R^9$s have the same meanings as those of $R^9$s in the general formula (3); Rs each independently represent a monovalent organic group (for example, a linear chain saturated hydrocarbon group having 1 to 20 carbon atoms, or the like) capable of forming an amine; and $X^-$ is a monovalent ion capable of forming an ammonium salt with an amine (for example, a halogen ion, a hydrogen sulfate ion, an acetate ion, or the like)]. The method represented by the reaction formula (III) proceeds as follows. Specifically, an acidic reaction liquid is obtained by using a cycloalkanone (cyclopentanone, cyclohexanone, or the like) represented by the general formula (I-1), an ammonium salt of a secondary amine (for example, a hydrochloric acid salt, a sulfuric acid salt, an acetic acid salt, or the like: a compound represented by the formula: $NHR_2HX$ in the reaction formula (III)) in an amount of 2 equivalents or more to the cycloalkanone, a formaldehyde derivative, and an acid (hydrochloric acid, sulfuric acid, acetic acid, or the like). Then, the reaction liquid is heated under an inert gas atmosphere at 30 to 180° C. for 0.5 to 10 hours, to thereby allow a Mannich reaction to proceed among the cyclic ketone having active α-hydrogens at both neighboring positions of the carbonyl group, the formaldehyde, and the secondary amine in the reaction liquid. Thus, the Mannich base represented by the general formula (I-2) is synthesized. Subsequently, a mixture is obtained by adding, to the reaction liquid without isolating the obtained Mannich base, an organic solvent (the organic solvent may be any, as long as the organic solvent can be used for a Diels-Alder reaction, and is preferably an organic solvent such as tetrahydrofuran, methanol, ethanol, isopropanol, butanol, acetonitrile, methyl cellosolve, ethyl cellosolve, ethylene glycol, propylene glycol monomethyl ether, propylene glycol, or the like), and a cyclopentadiene which may have, as a substituent, a group which is the same as that selectable as $R^1$ in the general formula (1) (in an amount of 2 equivalents or more to the Mannich base). Then, the mixture is adjusted to be neutral or basic by introducing a base thereto, and the mixture is stirred for 0.1 to 48 hours under a condition of 0 to 150° C. (preferably about 60° C.). Thus, a divinyl ketone represented by general formula (I-3) is synthesized in the mixture from the Mannich base represented by the general formula (I-2), and then the divinyl ketone represented by the general formula (I-3) and the cyclopentadiene which may have a substituent are reacted with each other (Diels-Alder reaction). In this manner, the compound represented by the general formula (3) is produced by this method. Note that, as the formaldehyde derivative, any known formaldehyde derivative which is used for producing a Mannich base can be used as appropriate, and, for example, formalin, paraformaldehyde, trioxane, 1,3-dioxolane, or the like can be used as appropriate. In addition, the divinyl ketone is synthesized when an amine compound is eliminated from the Mannich base during the stirring of the mixture under the condition of 0 to 150° C.

In addition, examples of the cycloalkanone represented by the general formula (I-1) in the reaction formula (III) include cyclopropanone, cyclobutanone, cyclopentanone, cyclohexanone, cycloheptanone, cyclooctanone, cyclononanone, cyclodecanone, cycloundecanone, cyclododecanone, cyclotridecanone, cyclotetradecanone, cyclopentadecanone, 3-methylcyclobutanone, 3-methylcyclopentanone, 3-methylcyclohexanone, 3-methylcycloheptanone, 3-methylcyclooctanone, 3-methylcyclononanone, 3-methylcyclodecanone, 3-methylcycloundecanone, 3-methylcyclododecanone, 3-methylcyclotridecanone, 3-methylcyclotetradecanone, 3-methylcyclopentadecanone, and the like. Meanwhile, examples of the ammonium salt of the secondary amine include salts (secondary amine salts in which the aforementioned $X^-$ serves as a counter anion) of secondary amines such as dimethylamine, diethylamine, di-n-propylamine, diisopropylamine, di-n-butylamine, diisobutylamine, di-sec-butylamine, di-t-butylamine, dipentylamine, dicyclopentylamine, dihexylamine, dicyclohexylamine, diheptylamine, dioctylamine, di(2-ethylhexyl) amine, dinonylamine, didecylamine, diundecylamine, didodecylamine, ditridecylamine, ditetradecylamine, dipentadecylamine, dihexadecylamine, diheptadecylamine, dioctadecylamine, dinonadecylamine, morpholine, diethanolamine, aziridine, azetidine, pyrrolidine, piperidine, indoline, and isoindoline. In addition, $X^-$ in the reaction formula (III) is a so-called counter anion, and examples thereof include $F^-$, $Cl^-$, $Br^-$, $I^-$, $CH_3COO^-$, $CF_3COO^-$, $CH_3SO_3^-$, $CF_3SO_3^-$, $C_6H_5SO_3^-$, $CH_3C_6H_4SO_3^-$, $HOSO_3^-$, $H_2PO_4^-$, and the like. In addition, the divinyl ketone is synthesized when an amine compound is eliminated from the Mannich base during the stirring of the mixture under the condition of 0 to 150° C.

In addition, the alcohol used in the first step is preferably an alcohol represented by the following general formula (11):

$$R^{12}OH \qquad (11)$$

[in the formula (11), $R^{12}$ is an atom or a group which can be selected as $R^5$, $R^6$, $R^7$ or $R^8$ in the general formula (2), but which is not a hydrogen atom]. Specifically, as the alcohol, an alkyl alcohol having 1 to 10 carbon atoms, a cycloalkyl alcohol having 3 to 10 carbon atoms, an alkenyl alcohol having 2 to 10 carbon atoms, an aryl alcohol having 6 to 20 carbon atoms, or an aralkyl alcohol having 7 to 20 carbon atoms is preferably used. Specific examples of the alcohol include methanol, ethanol, butanol, allyl alcohol, cyclohexanol, benzyl alcohol, and the like. Of these, methanol and ethanol are more preferable, and methanol is particularly preferable, from the viewpoint that it becomes easier to purify an obtained compound. In addition, these alcohols may be used alone or as a mixture of two or more kinds.

The reaction in the first step using the alcohol is a reaction (esterification reaction) in which the compound represented by the general formula (3) is reacted with the alcohol ($R^{12}OH$) and carbon monoxide (CO) in the presence of a palladium catalyst and an oxidizing agent, and thereby ester groups each represented by the following general formula (12):

$$-COOR^{12} \qquad (12)$$

[in the formula (12), $R^{12}$ is an atom or a group which can be selected as $R^5$, $R^6$, $R^7$, or $R^8$ in the general formula (2), but which is not a hydrogen atom]
(in each position in which the ester group is introduced, each of $R^{12}$s may represent the same or different one) are introduced at olefinic positions in the 5-norbornene-2-spiro-α-cycloalkanone-α'-spiro-2"-5"-norbornene represented by the general formula (3), so that the norbornane-2-spiro-α-cycloalkanone-α'-spiro-2"-norbornane-5,5",6,6"-tetracarboxylic acid ester represented by the general formula (2) is obtained.

The amount of the alcohol used in the esterification reaction is not particularly limited, as long as the compound represented by the general formula (2) can be obtained. For example, it is possible to add the alcohol in an amount more than the amount (theoretical amount) theoretically necessary to obtain the compound represented by the general formula (2), and use the excessive alcohol as a solvent, as it is.

In addition, in the esterification reaction, the amount of the above-described carbon monoxide is any, as long as a necessary amount of carbon monoxide is supplied to the reaction system. Accordingly, it is unnecessary to use high-purity carbon monoxide gas as the carbon monoxide, but it is possible to use a mixture gas obtained by mixing carbon monoxide with an inert gas (for example, nitrogen) for the esterification reaction. In addition, the pressure of the carbon monoxide is not particularly limited, and is preferably not lower than normal pressure (approximately 0.1 MPa [1 atm]) but not higher than 10 MPa.

In addition, the palladium catalyst used in the first step is not particularly limited, and a known catalyst containing palladium can be used as appropriate. Examples thereof include palladium inorganic acid salts, palladium organic acid salts, catalysts in which palladium is supported on a support, and the like. Specific examples of the palladium catalyst include palladium chloride, palladium nitrate, palladium sulfate, palladium acetate, palladium propionate, palladium carbon, palladium alumina, palladium black, and the like. The amount of the palladium catalyst used is preferably set such that the molar amount of palladium in the palladium catalyst can be 0.001 to 0.1 times the molar amount of the compound represented by the general formula (3).

Moreover, the oxidizing agent used in the first step is not particularly limited, as long as the oxidizing agent can oxidize $Pd^0$ to $Pd^{2+}$, when $Pd^{2+}$ in the palladium catalyst is reduced to $Pd^0$ in the esterification reaction. Examples of the oxidizing agent include copper compounds, iron compounds, and the like. Specific examples of the oxidizing agent include copper(II) chloride, copper(II) nitrate, copper (II) sulfate, copper(II) acetate, iron(III) chloride, iron(III) nitrate, iron(III) sulfate, iron(III) acetate, and the like. The molar amount of the oxidizing agent used is preferably 2 to 16 times (more preferably about 8 times) the molar amount of the 5-norbornene-2-spiro-α-cycloalkanone-α'-spiro-2"-5"-norbornene represented by the general formula (3).

In addition, it is preferable to use a solvent for the reaction (esterification reaction) of the compound represented by the general formula (3) with the alcohol and carbon monoxide. The solvent is not particularly limited, and examples thereof include hydrocarbon-based solvents such as n-hexane, cyclohexane, heptane, and pentane.

Moreover, since an acid is by-produced from the oxidizing agent and the like in the esterification reaction, a base may be added to remove the acid. The base is preferably a fatty acid salt such as sodium acetate, sodium propionate, sodium butyrate, or the like. In addition, the amount of the base used may be adjusted as appropriate depending on the amount of the acid generated and the like.

In addition, a reaction temperature condition in the esterification reaction is not particularly limited, and is preferably 0° C. to 100° C. {more preferably about normal temperature (25° C.)}. If the reaction temperature exceeds the upper limit, the yield tends to decrease. Meanwhile, if the reaction temperature is lower than the lower limit, the reaction rate tends to decrease. In addition, a reaction time of the esterification reaction is not particularly limited, and is preferably set to about 30 minutes to 24 hours.

In addition, in order to convert $R^5$, $R^6$, $R^7$, or $R^8$ in the general formula (2) into a hydrogen atom, a hydrolysis treatment or a transesterification reaction with a carboxylic acid may be conducted, after the introduction of the groups represented by the above-described formula: $-COOR^{12}$ by the esterification reaction. A method for the reaction is not particularly limited, and a known method capable of converting the groups represented by the formula: $-COOR^{12}$ into those represented by the formula: $-COOH$ can be employed as appropriate.

In addition, after the esterification reaction, the hydrolysis, or the like is conducted as described above, a purification step such as recrystallization may be conducted as appropriate in order to obtain a compound having a higher purity. A method for the purification is not particularly limited, and a known method can be employed as appropriate. Thus, the norbornane-2-spiro-α-cycloalkanone-α'-spiro-2"-norbornane-5,5",6,6"-tetracarboxylic acid ester represented by the general formula (2) of the present invention can be obtained in a high yield by the first step.

Next, the second step is described. The second step is a step of obtaining a norbornane-2-spiro-α-cycloalkanone-α'-spiro-2"-norbornane-5,5",6,6"-tetracarboxylic dianhydride represented by general formula (1) (hereinafter simply referred to as a "compound represented by the general formula (1)" or a "tetracarboxylic dianhydride represented by the general formula (1)" in some cases) from at least one compound of the norbornane-2-spiro-α-cycloalkanone-α'-spiro-2"-norbornane-5,5",6,6"-tetracarboxylic acids and esters thereof by using formic acid, an acid catalyst, and acetic anhydride.

The acid catalyst used in the second step is not particularly limited, and is preferably p-toluenesulfonic acid, benzenesulfonic acid, hydrochloric acid, nitric acid, sulfuric acid, phosphoric acid, methanesulfonic acid, or trifluoroacetic acid, and more preferably p-toluenesulfonic acid, from the viewpoint of the acid strength. The molar amount of the acid catalyst used in the second step is preferably 0.01 to 0.2 times the molar amount of the compound represented by the general formula (2). If the amount of the acid catalyst used is less than the lower limit, the reaction rate tends to decrease. Meanwhile, if the amount of the acid catalyst exceeds the upper limit, the yield tends to decrease.

In addition, the amount of formic acid used in the second step is not particularly limited, and the molar amount of formic acid is preferably 4 to 100 times the molar amount of the compound represented by the general formula (2). If the amount of formic acid used is less than lower limit, the reaction rate tends to decrease. Meanwhile, if the amount of formic acid exceeds the upper limit, the yield tends to decrease.

Moreover, the amount of acetic anhydride used in the second step is not particularly limited, and the molar amount of acetic anhydride is preferably 4 to 100 times the molar amount of the compound represented by the general formula (2). If the amount of acetic anhydride used is less than the lower limit, the reaction rate tends to decrease. Meanwhile, if the amount of acetic anhydride exceeds the upper limit, the yield tends to decrease.

In addition, the second step is not particularly limited, but, for example, preferably comprises the following steps (A) to (C). Specifically, the second step preferably comprises: a step (A) of preparing a mixture liquid of the compound represented by the general formula (2) with formic acid and the acid catalyst, and heating the mixture liquid under reflux; a step (B) of obtaining a liquid concentrate by concentrating the mixture liquid by partially evaporating liquid in the mixture liquid under reduced pressure, adding formic acid again to an obtained liquid concentrate and heating the mixture under reflux, and then concentrating again the obtained mixture liquid by partially evaporating liquid in the obtained mixture liquid under reduced pressure; and a step (C) of adding formic acid and acetic anhydride to the liquid concentrate, and heating the mixture under reflux, to thereby obtain a compound represented by the general formula (1). The employment of this method makes it possible to obtain more efficiently the compound represented by the general formula (1) from the compound represented by the general formula (2).

In addition, when such a method is employed, the step of performing the addition of formic acid to the liquid concentrate and the concentration of the liquid concentrate is preferably conducted repeatedly (preferably conducted 1 to 5 times repeatedly) in the step (B). By repeatedly conducting the step of performing the addition of formic acid to the liquid concentrate and the concentration of the liquid concentrate in the step (B), a tetra ester can be completely converted into a tetracarboxylic acid, when any one of $R^5$, $R^6$, $R^7$ and $R^8$ in the general formula (2) is a group other than a hydrogen atom, and the compound represented by the general formula (1) can be obtained more efficiently in the step (C) conducted after the step (B). Moreover, the molar amount of formic acid used in the production of the mixture liquid in the step (A) is preferably about 50 times as the molar amount of the compound represented by the general formula (2). In addition, the amount of formic acid added to the liquid concentrate in each of the steps (B) and (C) is preferably approximately equal to the amount of the liquid evaporated during the concentration.

In addition, a method for the concentration (evaporation under reduced pressure) of the mixture liquid in the step (B) is not particularly limited, and a known method can be employed as appropriate. In addition, a temperature condition of the heating under reflux each of in the steps (A) to (C) is preferably 100° C. to 140° C. If the temperature of the heating under reflux is lower than the lower limit, the yield tends to decrease. Meanwhile, if the temperature exceeds the upper limit, by-products tend to increase. In addition, a time of the heating under reflux is preferably set to about 30 minutes to 24 hours.

Moreover, after a crude product of the compound represented by the general formula (1) is obtained from the compound represented by the general formula (2) in the second step, the crude product may be subjected to a purification step such as recrystallization or sublimation as appropriate. The purification step makes it possible to obtain the compound represented by the general formula (1) having a higher purity. A method for the purification is not particularly limited, and a known method can be employed as appropriate.

By conducting the second step as described above, the norbornane-2-spiro-α-cycloalkanone-α'-spiro-2"-norbornane-5,5",6,6"-tetracarboxylic dianhydride represented by the general formula (1) of the present invention can be obtained in a high yield.

Hereinabove, the method for producing a norbornane-2-spiro-α-cycloalkanone-α'-spiro-2"-norbornane-5,5",6,6"-tetracarboxylic dianhydride of the present invention is described. Next, a description is given of other methods capable of producing the norbornane-2-spiro-α-cycloalkanone-α'-spiro-2"-norbornane-5,5",6,6"-tetracarboxylic dianhydride of the present invention. An example of the other methods is as follows. Specifically, after a norbornane-2-spiro-α-cycloalkanone-α'-spiro-2"-norbornane-5,5",6,6"-tetracarboxylic acid ester represented by the general formula (2) is obtained by conducting the first step, the norbornane-2-spiro-α-cycloalkanone-α'-spiro-2"-norbornane-5,5",6,6"-tetracarboxylic acid ester is hydrolyzed in the presence of an acid catalyst or a base catalyst, to thereby produce the norbornane-2-spiro-α-cycloalkanone-α'-spiro-2"-norbornane-5,5",6,6"-tetracarboxylic acid. After that, the obtained norbornane-2-spiro-α-cycloalkanone-α'-spiro-2"-norbornane-5,5",6,6"-tetracarboxylic acid is subjected to dehydrating ring closure by heating or by use of a dehydrating agent, to thereby produce the norbornane-2-spiro-α-cycloalkanone-α'-spiro-2"-norbornane-5,5",6,6"-tetracarboxylic dianhydride represented by the general formula (1).

In addition, the norbornane-2-spiro-α-cycloalkanone-α'-spiro-2"-norbornane-5,5",6,6"-tetracarboxylic dianhydride represented by the general formula (1) of the present invention is particularly useful as a raw material for polyamic acids, and as a raw material for heat-resistant resins such as polyimides.

As a method for producing a polyimide, a method may be employed, for example, in which the norbornane-2-spiro-α-cycloalkanone-α'-spiro-2"-norbornane-5,5",6,6"-tetracarboxylic dianhydride represented by the general formula (1) is reacted with a diamine compound in a solvent, to thereby obtain a polyamic acid, and then the polyamic acid is subjected to dehydrating ring closure with heating or an acid anhydride, to thereby obtain a polyimide.

The diamine compound is not particularly limited, and a known diamine compound which can be used for producing a polyimide or a polyamic acid can be used as appropriate. For example, an aromatic diamine, an aliphatic diamine, an alicyclic diamine, or the like can be used as the diamine compound as appropriate. Examples of the aromatic diamine include diaminodiphenylmethane, diaminodiphenyl ether, phenylenediamine, diaminodiphenylsulfonic acid, bis(aminophenoxy)benzene, diaminobiphenyl, diaminonaphthalene, and the like. Examples of the aliphatic diamine include ethylenediamine, propylenediamine, trimethylenediamine, tetramethylenediamine, hexamethylenediamine, and the like. In addition, examples of the alicyclic diamine include 4,4'-diamino-dicyclohexylmethane, 3,3'-dimethyl-4,4'-diamino-dicyclohexylmethane, 3,3'-diethyl-4,4'-diamino-dicyclohexylmethane, 3,3',5,5'-tetramethyl-4,4'-diamino-dicyclohexylmethane, 3,3',5,5'-tetraethyl-4,4'-diamino-dicyclohexylmethane, 3,5-diethyl-3',5'-dimethyl-4,4'-diamino-dicyclohexylmethane, and the like. Note that these diamine compounds may be used alone or in combination of two or more kinds.

In addition, the solvent used for producing the polyimide is not particularly limited, and a known solvent which can be used for producing a polyimide can be used as appropriate. Examples of the solvent include dimethylformamide, dimethylacetamide, N-methylpyrrolidone, dimethyl sulfoxide, cresol, and the like.

In addition, the amounts of the norbornane-2-spiro-α-cycloalkanone-α'-spiro-2"-norbornane-5,5",6,6"-tetracarboxylic dianhydride represented by the general formula (1) and the diamine compound used are not particularly limited, and are preferably set such that the molar ratio therebetween ([the compound represented by general formula (1)]:[the diamine compound]) can be 0.5:1.0 to 1.0:0.5 (more preferably 0.9:1.0 to 1.0:0.9). If the amount of the compound represented by the general formula (1) used is less than the lower limit, the yield tends to decrease. Meanwhile, if the amount exceeds the upper limit, the yield also tends to decrease.

In addition, a temperature condition and a heating time in the step of heating the polyamic acid are not particularly limited, and may be adjusted as appropriate to conditions under which a polyimide can be produced. For example, conditions of heating at about 100 to 400° C. for about 0.1 to 24 hours may be employed. Moreover, the acid anhydride used for the dehydrating ring closure of the polyamic acid is not particularly limited, as long as the acid anhydride is capable of causing dehydrating ring closure of the polyamic acid. A known acid anhydride can be used as the acid anhydride as appropriate. Examples thereof include propionic anhydride, acetic anhydride, and the like. In addition, a method for the dehydrating ring closure using the acid anhydride is not particularly limited, and known conditions under which the polyamic acid can be subjected to the dehydrating ring closure may be employed as appropriate.

In addition, the polyimide obtained as described above use, as one of the monomers, the norbornane-2-spiro-α-cycloalkanone-α'-spiro-2"-norbornane-5,5",6,6"-tetracarboxylic dianhydride represented by the general formula (1). Hence, although the aliphatic tetracarboxylic dianhydride is used, the polyimide can be colorless and transparent, while having a sufficiently high level of solubility in a solvent, have a sufficiently high heat resistance in terms of a glass transition temperature (Tg), which is an index of heat resistance, and have a sufficiently higher level of Tg than those of polyimides produced from conventionally known aliphatic tetracarboxylic dianhydrides. Accordingly, the norbornane-2-spiro-α-cycloalkanone-α'-spiro-2"-norbornane-5,5",6,6"-tetracarboxylic dianhydride represented by the general formula (1) of the present invention is particularly useful as a material for producing polyimides for flexible printed wiring boards, polyimides for heat resistant insulating tapes, polyimides for enamels for wires, polyimides for protective coatings of semiconductors, polyimides for liquid crystal orientation films, and the like.

Next, a polyimide of the present invention is described. Specifically, the polyimide of the present invention has a repeating unit represented by the following general formula (4):

[Chem. 19]

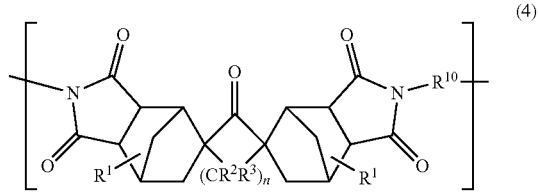

(4)

[in the formula (4), $R^1$s, $R^2$, and $R^3$ each independently represent one selected from the group consisting of a hydrogen atom, alkyl groups having 1 to 10 carbon atoms, and a fluorine atom, $R^{10}$ represents an aryl group having 6 to 40 carbon atoms, and n represents an integer of 0 to 12].

The alkyl group which can be selected as each $R^1$, $R^2$, or $R^3$ in the general formula (4) is an alkyl group having 1 to 10 carbon atoms. If the number of carbon atoms exceeds 10, the glass transition temperature is lowered, so that a sufficiently high level of heat resistance cannot be achieved. In addition, the number of carbon atoms of the alkyl group which can be selected as $R^1$, $R^2$, or $R^3$ is preferably 1 to 6, more preferably 1 to 5, further preferably 1 to 4, and particularly preferably 1 to 3, from the viewpoint that the purification becomes easier. In addition, the alkyl group which can be selected as $R^1$, $R^2$, or $R^3$ may be linear or branched. Moreover, the alkyl group is more preferably a methyl group or an ethyl group, from the viewpoint of ease of purification.

$R^1$s, $R^2$, and $R^3$ in the general formula (4) are each independently more preferably a hydrogen atom or an alkyl group having 1 to 10 carbon atoms, from the viewpoint that a higher level of heat resistance can be obtained when a polyimide is produced. Of these, $R^1$s, $R^2$, and $R^3$ are each independently more preferably a hydrogen atom, a methyl group, an ethyl group, a n-propyl group, or an isopropyl group, and particularly preferably a hydrogen atom or a methyl group, from the viewpoints that raw materials are readily available, and that the purification is easier. In addition, the plural $R^1$s, $R^2$s, and $R^3$s in the formula are particularly preferably the same, from the viewpoints of ease of purification and the like.

In addition, the aryl group which can be selected as $R^{10}$ in the general formula (4) is an aryl group having 6 to 40 carbon atoms. In addition, the number of the carbon atoms is preferably 6 to 30, and more preferably 12 to 20. If the number of carbon atoms exceeds the upper limit, the heat resistance tends to deteriorate. Meanwhile, if the number of carbon atoms is less than the lower limit, the solubility of the obtained polyimide in a solvent tends to decrease.

In addition, from the viewpoint of the balance between the heat resistance and the solubility, $R^{10}$ in the general formula (4) is preferably at least one of groups represented by the following general formulae (5) to (8):

[Chem. 20]

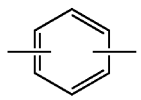

(5)

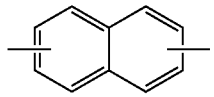

(6)

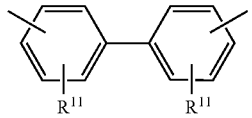

(7)

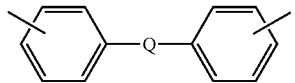

(8)

[in the formula (7), $R^{11}$s represent one selected from the group consisting of a hydrogen atom, a fluorine atom, a methyl group, an ethyl group, and a trifluoromethyl group, and in the formula (8), Q represents one selected from the group consisting of groups represented by the formulae: —O—, —S—, —CO—, —CONH—, —SO$_2$—, —C(CF$_3$)$_2$—, —C(CH$_3$)$_2$—, —CH$_2$—, —O—C$_6$H$_4$—C(CH$_3$)$_2$—C$_6$H$_4$—O—, —O—C$_6$H$_4$—SO$_2$—C$_6$H$_4$—O—, —C(CH$_3$)$_2$—C$_6$H$_4$—C(CH$_3$)$_2$—, —O—C$_6$H$_4$—C$_6$H$_4$—O—, and —O—C$_6$H$_4$—O—].

$R^{11}$s in the general formula (7) are each more preferably a hydrogen atom, a fluorine atom, a methyl group, or an ethyl group, and particularly preferably a hydrogen atom, from the viewpoint of the heat resistance.

In addition, Q in the general formula (8) is preferably a group represented by the formula: —O—C$_6$H$_4$—O—, —O—, —C(CH$_3$)$_2$—, —CH$_2$—, or —O—C$_6$H$_4$—C(CH$_3$)$_2$—C$_6$H$_4$—O—, and particularly preferably a group represented by the formula: —O—C$_6$H$_4$—O— or —O—, from the viewpoint of the balance between the heat resistance and the solubility.

In addition, the group which can be selected as $R^{10}$ and is represented by the general formulae (5) to (8) is more preferably a group represented by the general formula (7) or (8), and particularly preferably a group represented by the general formula (8), from the viewpoint that a higher level of heat resistance can be obtained.

In addition, n in the general formula (4) represents an integer of 0 to 12. If the value of n exceeds the upper limit, the purification becomes difficult. In addition, an upper limit value of the numeric value range of n in the general formula (4) is more preferably 5, and particularly preferably 3, from the viewpoint that the purification becomes easier. In addition, a lower limit value of the numeric value range of n in the general formula (4) is more preferably 1, and particularly preferably 2, from the viewpoint of the stability of a raw material of the tetracarboxylic dianhydride represented by the general formula (1). Accordingly, n in the general formula (4) is particularly preferably an integer of 2 or 3.

The polyimide is preferably one having a 5% weight loss temperature of 400° C. or above, and more preferably one having a 5% weight loss temperature of 450 to 550° C. If the 5% weight loss temperature is lower than the lower limit, it tends to be difficult to achieve a sufficient heat resistance. Meanwhile, if the 5% weight loss temperature exceeds the upper limit, it tends to be difficult to produce a polyimide having such a characteristic. Note that the 5% weight loss temperature can be determined by gradually heating a sample from room temperature (25° C.) under a nitrogen gas atmosphere with a nitrogen gas flow and measuring a temperature at which the weight loss of the sample used reaches 5%.

In addition, the polyimide is preferably one having a glass transition temperature (Tg) of 250° C. or above, and more preferably one having a glass transition temperature (Tg) of 300 to 500° C. If the glass transition temperature (Tg) is lower than the lower limit, it tends to be difficult to achieve a sufficient heat resistance. Meanwhile, if the glass trans it ion temperature (Tg) exceeds the upper limit, it tends to be difficult to produce a polyimide having such a characteristic. Note that the glass transition temperature (Tg) can be measured by using a differential scanning calorimeter (manufactured by SII NanoTechnology Inc., under the trade name of "DSC220").

In addition, the polyimide is preferably one having a thermal decomposition temperature (Td) of 450° C. or above, and more preferably one having a thermal decomposition temperature (Td) of 480 to 600° C. If the thermal decomposition temperature (Td) is lower than the lower limit, it tends to be difficult to achieve a sufficient heat resistance. Meanwhile, if the thermal decomposition temperature (Td) is higher than the upper limit, it tends to be difficult to produce a polyimide having such a characteristic. Note that the thermal decomposition temperature (Td) can be determined by measuring a temperature at which tangent lines of decomposition curves before and after a thermal decomposition intersect with each other, by using a TG/DTA 220 thermogravimetric analyzer (manufactured by SII NanoTechnology Inc.), under conditions of a nitrogen atmosphere and a rate of temperature rise of 10° C./min.

Moreover, the number average molecular weight (Mn) of the polyimide is preferably 1000 to 1000000, and more preferably 10000 to 100000, in terms of polystyrene. If the number average molecular weight is lower than the lower limit, it tends to be difficult to achieve a sufficient heat resistance. Meanwhile, if the number average molecular weight exceeds the upper limit, the processing tends to be difficult.

Meanwhile, a weight average molecular weight (Mw) of the polyimide is preferably 1000 to 5000000 in terms of polystyrene. In addition, a lower limit value of the numeric value range of the weight average molecular weight (Mw) is more preferably 1000, further preferably 5000, and particularly preferably 10000. Meanwhile, an upper limit value of the numeric value range of the weight average molecular weight (Mw) is more preferably 5000000, further preferably 500000, and particularly preferably 50000. If the weight average molecular weight (Mw) is lower than the lower limit, it tends to be difficult to achieve a sufficient heat resistance. Meanwhile, if the weight average molecular weight (Mw) exceeds the upper limit, the processing tends to be difficult.

Moreover, the molecular weight distribution (Mw/Mn) of the polyimide is preferably 1.1 to 5.0, and more preferably 1.5 to 3.0. If the molecular weight distribution (Mw/Mn) is lower than the lower limit, the production tends to be difficult. Meanwhile, if the molecular weight distribution (Mw/Mn) exceeds the upper limit, it tends to be difficult to obtain a uniform film. Note that each molecular weight (Mw or Mn) and the molecular weight distribution (Mw/Mn) of the polyimide can be determined by measurement using, as a measuring apparatus, a gel permeation chromatography (GPC, manufactured by Tosoh Corporation, trade name: HLC-8020/Four columns: manufactured by Tosoh Corporation, trade name: TSK gel GMH$_{HR}$ and the like), and also using, as a solvent, tetrahydrofuran (THF), and then converting the obtained data in terms of polystyrene.

In addition, the polyimide is more preferably one mainly comprising the repeating unit represented by the general formula (4) (further preferably one in which the content of the repeating unit represented by the general formula (4) is 50 to 100% by mole relative to all the repeating units). Note that the polyimide may comprise other repeating units, as long as the effects of the present invention are not impaired. Examples of the other repeating units include repeating units derived from tetracarboxylic dianhydrides other than the above-described norbornane-2-spiro-α-cycloalkanone-α'-spiro-2"-norbornane-5,5",6,6"-tetracarboxylic dianhydride represented by the general formula (1), and the like.

Next, a polyamic acid of the present invention is described. The polyamic acid of the present invention has a repeating unit represented by the following general formula (9):

[Chem. 21]

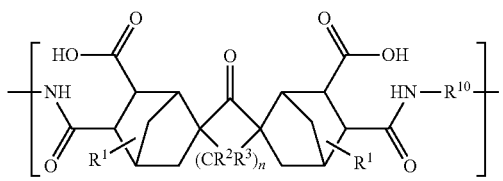

(9)

[in the formula (9), R$^1$s, R$^2$, and R$^3$ each independently represent one selected from the group consisting of a hydrogen atom, alkyl groups having 1 to 10 carbon atoms, and a fluorine atom, R$^{10}$ represents an aryl group having 6 to 40 carbon atoms, and n represents an integer of 0 to 12].

The polyamic acid can be obtained as a reaction intermediate (precursor) in producing the polyimide of the present invention by utilizing a method for producing a polyimide of the present invention to be described later. R$^1$s, R$^2$, R$^3$, R$^{10}$, and n in the general formula (9) are the same as those for R$^1$s, R$^2$, R$^3$, R$^{10}$, and n in the general formula (4), and preferred examples thereof are also the same as those of R$^1$s, R$^2$, R$^3$, R$^{10}$, and n in the general formula (4).

In addition, the polyamic acid is preferably one having an intrinsic viscosity [η] of 0.05 to 3.0 dL/g, and more preferably one having an intrinsic viscosity [η] of 0.1 to 2.0 dL/g. If the intrinsic viscosity [η] is lower than 0.05 dL/g, a film obtained when a film-shaped polyimide is produced by using this polyamic acid tends to be brittle. Meanwhile, if the intrinsic viscosity [η] exceeds 3.0 dL/g, the processability deteriorates because of the excessively high viscosity, so that it becomes difficult to obtain a uniform film when the film is produced from this polyamic acid, for example. In addition, the intrinsic viscosity [η] can be measured as follows. Specifically, first, a measurement sample (solution) is obtained by using N,N-dimethylacetamide as a solvent, and dissolving the polyamic acid into the N,N-dimethylacetamide at a concentration of 0.5 g/dL. Next, by using the measurement sample, the viscosity of the measurement sample is measured with a kinematic viscometer under a temperature condition of 30° C., and the thus determined value is employed as the intrinsic viscosity [η]. Note that a kinematic viscometer manufactured by THOMAS SCIENTIFIC CO. under the trade name of "KINEMATIC VISCOMETER TV-5S" is used as the kinematic viscometer.

Next, a description is given of a method for producing a polyimide of the present invention which can be preferably used also as a method for producing the polyimide of the present invention. The method for producing a polyimide of the present invention is a method comprising:

a step (step (I)) of reacting a norbornane-2-spiro-α-cycloalkanone-α'-spiro-2"-norbornane-5,5",6,6"-tetracarboxylic dianhydride with an aromatic diamine in the presence of an organic solvent, to thereby obtain a polyamic acid having a repeating unit represented by the general formula (9), the norbornane-2-spiro-α-cycloalkanone-α'-spiro-2"-norbornane-5,5",6,6"-tetracarboxylic dianhydride being represented by the following general formula (1):

[Chem. 22]

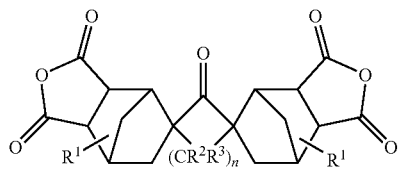

(1)

[in the formula (1), R$^1$s, R$^2$, and R$^3$ each independently represent one selected from the group consisting of a hydrogen atom, alkyl groups having 1 to 10 carbon atoms, and a fluorine atom, and n represents an integer of 0 to 12], the aromatic diamine being represented by the following general formula (10):

[Chem. 23]

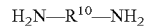

$H_2N-R^{10}-NH_2$ (10)

[in the formula (10), R$^{10}$ represents an aryl group having 6 to 40 carbon atoms]; and a step (step (II)) of subjecting the polyamic acid to imidization, to thereby obtain a polyimide having a repeating unit represented by the general formula (4). The step (I) and the step (II) are described separately below.

(Step (I))

The step (I) is a step of reacting the tetracarboxylic dianhydride represented by the general formula (1) with the aromatic diamine represented by the general formula (10) in the presence of an organic solvent, to thereby obtain a polyamic acid having a repeating unit represented by the general formula (9).

Regarding the tetracarboxylic dianhydride represented by the general formula (1) and used in the step (I), $R^1$s, $R^2$, $R^3$, and n in the formula (1) are the same as those for $R^1$s, $R^2$, $R^3$, and n in the general formula (4), and preferred examples thereof are also the same as those of $R^1$s, $R^2$, $R^3$, and n in the general formula (4).

In addition, a method for producing the tetracarboxylic dianhydride represented by the general formula (1) and used in the step (I) is not particularly limited, and, for example, a method may be employed in which a compound represented by the general formula (3) is obtained by using the reaction represented by the above-described reaction formula (III), and then the compound represented by the general formula (3) is converted into a tetracarboxylic dianhydride by utilizing a known method or the like as appropriate, to thereby obtain the tetracarboxylic dianhydride represented by the general formula (1).

In addition, a method for converting the compound represented by the general formula (3) into a tetracarboxylic dianhydride is not particularly limited, and a known method can be used as appropriate. For example, the method described in Macromolecules published in 1994 (Vol. 27), p. 1117 may be employed. Specifically, as a method for conversion into the a tetracarboxylic dianhydride, it is possible to employ a method in which the compound represented by the general formula (3) is converted into a tetra ester with carbon monoxide and methanol in the presence of a Pd catalyst, copper chloride (II), and sodium acetate; the obtained tetramethyl ester is subjected to transesterification reaction with formic acid in the presence of an acid catalyst such as p-toluenesulfonic acid, to thereby obtain a tetracarboxylic acid; and then the tetracarboxylic acid is converted with acetic anhydride into a tetracarboxylic dianhydride by causing acetic anhydride to coexist in a reaction system of the transesterification reaction; or a method in which the tetracarboxylic acid is once isolate, and then subjected to a thermal dehydration reaction in a sublimation purification apparatus under a vacuum condition.

Note that, as a method for producing the tetracarboxylic dianhydride represented by the general formula (1) and used in the step (I), the above-described method for producing a norbornane-2-spiro-α-cycloalkanone-α'-spiro-2''-norbornane-5,5'',6''-tetracarboxylic dianhydride of the present invention can be used preferably.

In addition, in the aromatic diamine represented by the general formula (10) and used in the step (I), $R^{10}$ in the formula (10) is the same as that for $R^{10}$ in the general formula (4), and preferred examples thereof are also the same as those of $R^{10}$ in the general formula (4).

Examples of the aromatic diamine represented by the general formula (10) include 4,4'-diaminodiphenylmethane, 3,3'-diaminodiphenylmethane, 4,4'-diaminodiphenylethane, 3,3'-diaminodiphenylethane, 4,4'-diaminobiphenyl, 3,3'-diaminobiphenyl, 4,4'-diaminodiphenyl ether, 3,3'-diaminodiphenyl ether, 2,2-bis(4-aminophenoxyphenyl)propane, 1,3-bis(4-aminophenoxy)benzene, 1,3-bis(3-aminophenoxy)benzene, bis[4-(4-aminophenoxy)phenyl]sulfone, bis[4-(3-aminophenoxy)phenyl]sulfone, 2,2'-bis(trifluoromethyl)-4,4'-diaminobiphenyl, 3,4'-diaminodiphenyl ether, 4,4'-diaminobenzophenone, 3,3'-diaminobenzophenone, 9,9-bis(4-aminophenyl)fluorene, p-diaminobenzene, m-diaminobenzene, o-diaminobenzene, 4,4'-diaminobiphenyl, 3,3'-diaminobiphenyl, 2,2'-diaminobiphenyl, 3,4'-diaminobiphenyl, 2,6-diaminonaphthalene, 1,4-diaminonaphthalene, 1,5-diaminonaphthalene, 4,4'-[1,3-phenylenebis(1-methylethylidene)]bisaniline, 4,4'-[1,4-phenylenebis(1-methylethylidene)]bisaniline, 2,2'-dimethyl-4,4'-diaminobiphenyl, 3,3'-dimethyl-4,4'-diaminobiphenyl, 3,3'-diaminodiphenyl sulfone, 4,4'-diaminodiphenyl sulfone, 4,4'-diaminodiphenyl sulfide, 1,4-bis(4-aminophenoxy)benzene, 4,4'-bis(4-aminophenoxy)biphenyl, 4,4'-diaminobenzanilide, 9,9'-bis(4-aminophenyl)fluorene, o-tolidine sulfone, 1,3'-bis(4-aminophenoxy)-2,2-dimethylpropane, 2,3,5,6-tetramethyl-1,4-phenylenediamine, 3,3',5,5'-tetramethylbenzidine, 1,5-bis(4-aminophenoxy)pentane, and the like.

A method for producing the aromatic diamine is not particularly limited, and a known method can be employed as appropriate. In addition, as the aromatic diamine, a commercially available one can be used as appropriate.

In addition, the organic solvent used in the step (I) is preferably an organic solvent capable of dissolving both the tetracarboxylic dianhydride represented by the general formula (1) and the aromatic diamine represented by the general formula (10). Examples of the organic solvent include aprotic polar solvents such as N-methyl-2-pyrrolidone, N,N-dimethylacetamide, N,N-dimethylformamide, dimethyl sulfoxide, γ-butyrolactone, propylene carbonate, tetramethylurea, 1,3-dimethyl-2-imidazolidinone, hexamethylphosphoric triamide, and pyridine; phenol-based solvents such as m-cresol, xylenol, phenol, and halogenated phenols; ether-based solvents such as tetrahydrofuran, dioxane, cellosolves, and glymes; aromatic solvents such as benzene, toluene, and xylene; and the like. These organic solvents may be used alone or as a mixture of two or more kinds.

In addition, the ratio between the tetracarboxylic dianhydride represented by the general formula (1) and the aromatic diamine represented by the general formula (10) used in the step (I) is such that the acid anhydride groups of the tetracarboxylic dianhydride represented by the general formula (1) are preferably 0.2 to 2 equivalents, and more preferably 0.3 to 1.2 equivalents, relative to 1 equivalent of the amino groups of the aromatic diamine represented by the general formula (10). If the ratio of the use is less than the lower limit, there is a tendency that the polymerization reaction proceeds inefficiently, so that a polyamic acid having a high molecular weight cannot be obtained. Meanwhile, if the ratio of the use exceeds the upper limit, there is a tendency that a polyamic acid having a high molecular weight cannot be obtained, as in the above-described case.

Moreover, the amount of the organic solvent used in the step (I) is preferably such that a total amount of the tetracarboxylic dianhydride represented by the general formula (1) and the aromatic diamine represented by the general formula (10) can be 0.1 to 50% by mass (more preferably 10 to 30% by mass) relative to the entire amount of the reaction solution. If the amount of the organic solvent used is less than the lower limit, there is a tendency that a polyamic acid cannot be obtained efficiently. Meanwhile, if the amount of the organic solvent used exceeds the upper limit, stirring tends to be difficult because of the high viscosity.

In addition, a basic compound may be further added to the organic solvent in reacting the tetracarboxylic dianhydride represented by the general formula (1) with the aromatic diamine represented by the general formula (10) in the step (I), from the viewpoints of improving the reaction rate, and of obtaining a polyamic acid with a high degree of polymerization. The basic compound is not particularly limited, and examples thereof include triethylamine, tetrabutylamine, tetrahexylamine, 1,8-diazabicyclo[5.4.0]-undecene-7, pyridine, isoquinoline, α-picoline, and the like. In addition, the amount of the basic compound used is preferably 0.001 to equivalents, and more preferably 0.01 to 0.1 equivalents, relative to 1 equivalent of the tetracarboxylic dianhydride represented by the general formula (1). If the amount of the basic compound used is less than the lower limit, there is a tendency that an effect of the addition is not observed. Meanwhile, if the amount of the basic compound used exceeds the upper limit, coloring and the like tend to be caused.

In addition, a reaction temperature in reacting the tetracarboxylic dianhydride represented by the general formula (1) with the aromatic diamine represented by the general formula (10) in the step (I) may be adjusted as appropriate to a temperature at which these compounds can be reacted with each other. The reaction temperature is not particularly limited, and is preferably set to 15 to 30° C. In addition, a method for reacting the tetracarboxylic dianhydride represented by the general formula (1) with the aromatic diamine represented by the general formula (10) employable in the step (I) is not particularly limited, and a method capable of conducting a polymerization reaction of a tetracarboxylic dianhydride with an aromatic diamine can be used as appropriate. For example, a method may be employed in which the aromatic diamine is dissolved in a solvent under an inert atmosphere of nitrogen, helium, argon, or the like under atmospheric pressure; then the tetracarboxylic dianhydride represented by the general formula (1) is added thereto at the above-described reaction temperature; and then the reaction is allowed to proceed for 10 to 48 hours. If the reaction temperature or the reaction time is less than the lower limit, it tends to be difficult to conduct a reaction sufficiently. Meanwhile, if the reaction temperature or the reaction time exceeds the upper limit, there is a tendency that the possibility of inclusion of a substance (oxygen or the like) which degrades the polymerization product is increased, so that the molecular weight is lowered.

Note that, when the polyimide obtained by the present invention is one comprising another repeating unit in addition to the repeating unit represented by the general formula (4), for example, another tetracarboxylic dianhydride may be used in the step (I) together with the tetracarboxylic dianhydride represented by the general formula (1), and these may be reacted with the aromatic diamine. Examples of the another tetracarboxylic dianhydride other than the tetracarboxylic dianhydride represented by the general formula (1) include aliphatic or alicyclic tetracarboxylic dianhydrides such as butanetetracarboxylic dianhydride, 1,2,3,4-cyclobutanetetracarboxylic dianhydride, 1,2,3,4-cyclopentanetetracarboxylic dianhydride, 2,3,5-tricarboxycyclopentylacetic dianhydride, 3,5,6-tricarboxynorbornane-2-acetic dianhydride, 2,3,4,5-tetrahydrofurantetracarboxylic dianhydride, 1,3,3a,4,5,9b-hexahydro-5-(tetrahydro-2,5-dioxo-3-furanyl)-naphtho[1,2-c]-furan-1,3-dione, 1,3,3a,4,5,9b-hexahydro-5-methyl-5-(tetrahydro-2,5-dioxo-3-furanyl)-naphtho[1,2-c]-furan-1,3-dione, 1,3,3a,4,5,9b-hexahydro-8-methyl-5-(tetrahydro-2,5-dioxo-3-furanyl)-naphtho[1,2-c]-furan-1,3-dione, 5-(2,5-dioxotetrahydrofural)-3-methyl-3-cyclohexene-1,2-dicarboxylic dianhydride, and bicyclo[2,2,2]-oct-7-ene-2,3,5,6-tetracarboxylic dianhydride; aromatic tetracarboxylic dianhydride such as pyromellitic dianhydride, 3,3',4,4'-benzophenonetetracarboxylic dianhydride, 3,3',4,4'-biphenyl sulfone tetracarboxylic dianhydride, 1,4,5,8-naphthalenetetracarboxylic dianhydride, 2,3,6,7-naphthalenetetracarboxylic dianhydride, 3,3',4,4'-biphenyl ether tetracarboxylic dianhydride, 3,3',4,4'-dimethyldiphenylsilanetetracarboxylic dianhydride, 3,3',4,4'-tetraphenylsilanetetracarboxylic dianhydride, 1,2,3,4-furantetracarboxylic dianhydride, 4,4'-bis(3,4-dicarboxyphenoxy)diphenyl sulfide dianhydride, 4,4'-bis(3,4-dicarboxyphenoxy)diphenyl sulfone dianhydride, 4,4'-bis(3,4-dicarboxyphenoxy)diphenylpropane dianhydride, 3,3',4,4'-perfluoroisopropylidenediphthalic dianhydride, 4,4'-(2,2-hexafluoroisopropylidene)diphthalic dianhydride, 3,3',4,4'-biphenyltetracarboxylic dianhydride, 2,3,3',4'-biphenyltetracarboxylic dianhydride, bis(phthalic acid) phenylphosphine oxide dianhydride, p-phenylene-bis(triphenylphthalic) dianhydride, m-phenylene-bis(triphenylphthalic) dianhydride, bis(triphenylphthalic acid)-4,4'-diphenyl ether dianhydride, and bis(triphenylphthalic acid)-4,4'-diphenylmethane dianhydride; and the like. Note that, when an aromatic tetracarboxylic acid is used, the amount of the aromatic tetracarboxylic acid used is preferably changed as appropriate within a range in which the obtained polyimide can have a sufficient transparency, in order to prevent coloring due to the intramolecular CT.

Next, the step (II) is described. The step (II) is a step of subjecting the polyamic acid having a repeating unit represented by the general formula (9) and being obtained in the step (I) to imidization, to thereby obtain a polyimide having a repeating unit represented by the general formula (4).

The method for performing the imidization is not particularly limited, as long as the polyamic acid can be subjected to imidization by the method. As the method, a known method can be employed as appropriate. It is preferable to employ, for example, a method in which the polyamic acid having a repeating unit represented by the general formula (9) is subjected to imidization by performing a heat treatment under a temperature condition of 60 to 400° C. (more preferably 60 to 350° C., further preferably 150 to 350° C., and particularly preferably 150° C. to 250° C.); or a method in which the imidization is conducted by using a so-called "imidization agent." In a case where the method for performing the imidization by performing such a heat treatment, if the heating temperature is lower than 60° C., the reaction tend to proceed slow, whereas, if the heating temperature exceeds the upper limit, coloring or decrease in molecular weight due to thermal decomposition tends to occur.

In addition, in a case where the method for performing the imidization by performing such a heat treatment, the following method may be employed. Specifically, in this method, after the step (I) is conducted, the reaction liquid (the reaction liquid containing the polyamic acid having a repeating unit represented by the general formula (9)) obtained by reacting the tetracarboxylic dianhydride represented by the general formula (1) with the aromatic diamine represented by the general formula (10) in the organic solvent is used as it is, without isolating the polyamic acid having a repeating unit represented by the general formula (9). This reaction liquid is subjected to a drying treatment, to thereby remove the solvent, and then the heat treatment is conducted thereon for the imidization. The drying treatment makes it possible to perform a heat treatment and the like, after the polyamic acid having a repeating unit represented by the general formula (9) is isolated in a form of a film or the like. A temperature condition in the method of the drying treatment is preferably 0 to 180° C., and more preferably 60 to 150° C. If the temperature condition in the drying treatment is lower than the lower limit, there is a tendency that the solvent is not dried. Meanwhile, if the temperature condition exceeds the upper limit, there is a tendency that the solvent boils, so that the film contains babbles and voids. In this case, for example, in a case where a film-shaped polyimide is produced, the obtained reaction liquid may be applied, as it is, onto a substrate (for example, a glass plate), and the drying treatment and the heat treatment may be conducted thereon. Thus, a film-shaped polyimide can be produced by a simple method. Note that a method for applying the reaction liquid is not particularly limited, and a known method (a casting method or the like) can be employed as appropriate. In addition, when the polyamic acid having a repeating unit represented by the general formula (9) is isolated for use from the reaction liquid, the isolating method is not particularly limited. A known method capable of isolating the polyamic acid can be employed as appropriate. For example, a method in which the polyamic acid is isolated as a product of reprecipitation or the like may be employed.

In addition, when a method for performing the imidization by using a so-called "imidization agent" is employed, the polyamic acid having a repeating unit represented by the general formula (9) is preferably subjected to imidization in the presence of the imidization agent in a solvent. As the solvent, organic solvents described for the step (I) can be used preferably. For this reason, when the method for performing the imidization by using an imidization agent is employed, it is more preferable to employ a method in which the reaction liquid (the reaction liquid containing the polyamic acid having a repeating unit represented by the general formula (9)) obtained by reacting the tetracarboxylic dianhydride represented by the general formula (1) with the aromatic diamine represented by the general formula (10) in the organic solvent is used as it is, without isolating the polyamic acid having a repeating unit represented by the general formula (9), and the imidization is conducted by adding an imidization agent to the reaction liquid. As the imidization agent, a known imidization agent can be used as appropriate, and examples thereof include acid anhydrides such as acetic anhydride, propionic anhydride, and trifluoroacetic anhydride; tertiary amines such as pyridine, collidine, lutidine, triethylamine, and N-methylpiperidine; and the like. In addition, a reaction temperature of the imidization in a case where the imidization is conducted by adding the imidization agent is preferably 0 to 180° C., and more preferably 60 to 150° C. In addition, the reaction time is preferably set to 0.1 to 48 hours. If the reaction temperature or the reaction time is less than the lower limit, it tends to difficult to perform the imidization sufficiently. Meanwhile, if the reaction temperature or the reaction time exceeds the upper limit, there is a tendency that the possibility of inclusion of a substance (oxygen or the like) which degrades the polymerization product is increased, so that the molecular weight is lowered. In addition, the amount of the imidization agent used is not particularly limited, and may be set to several millimoles to several moles (preferably about 0.05 to 4.0 mol) relative to 1 mol of the repeating unit represented by the general formula (9) in the polyamic acid.

The polyimide obtained as described above is obtained by using an alicyclic tetracarboxylic dianhydride, and hence has an extremely high transparency. In addition, the polyimide is particularly useful as a material for producing films for flexible printed wiring boards, heat resistant insulating tapes, enamels for wires, protective coating agents for semiconductors, liquid crystal orientation films, transparent electro-conductive films for organic ELs, flexible substrate films, flexible transparent electro-conductive films, transparent electro-conductive films for organic thin-film solar cells, transparent electro-conductive films for dye-sensitized solar cells, flexible gas-barrier films, films for touch panels, transfer belts, interlayer dielectric films, substrates for sensors, and the like.

The solution of the present invention comprises the above-described polyamic acid of the present invention, and the organic solvent. As the organic solvent used for the solution of the present invention, the above mentioned organic solvents used in the step (I) can be used preferably. As mentioned above, the organic solvent used for the solution of the present invention is preferably the same one as the organic solvent described in the step (I). Moreover, the solution of the present invention may be prepared by the step (I). In other words, the reaction liquid obtained by conducting the step (I) may be used as the solution of the present invention. As mentioned above, the solution of the present invention may be prepared by reacting the tetracarboxylic dianhydride represented by the general formula (1) with the aromatic diamine represented by the general formula (10) in the organic solvent to obtain the reaction liquid (the reaction liquid (the solution) containing the polyamic acid having a repeating unit represented by the general formula (9)).

The amount of the polyamic acid contained in the solution of the present invention is not particularly limited. Here, the amount of the polyamic acid contained in the solution is preferably 1 to 80% by mass, and is more preferably 5 to 50% by mass. If the amount of the polyamic acid is less than the lower limit, the molecular weight of the polyamic acid tends to decrease. Meanwhile, if the amount of the polyamic acid exceeds the upper limit, it tends to be difficult to prepare the polyimide. Note that, the solution of the present invention can be preferably used for producing the polyimide of the present invention.

EXAMPLES

Hereinafter, the present invention will be described more specifically based on Examples and Comparative Examples. However, the present invention is not limited to Examples below.

Note that, in the following description, the molecule structure of the compound obtained in each of Synthesis Examples and Examples was identified by measuring IR and NMR spectra by use of IR measuring apparatuses (manufactured by JASCO Corporation, trade name: FT/IR-460 and FT/IR-4100) and NMR measuring apparatuses (manufactured by VARIAN, trade name: UNITY INOVA-600, and manufactured by JEOL Ltd., JNM-Lambda500). Meanwhile, the 5% weight loss temperature was determine by heating a sample under a nitrogen gas flow under a condition of 10° C./min from room temperature (25° C.) by use of a thermogravimetric analyzer ("TG/DTA 220" manufactured by SII NanoTechnology Inc.), and measuring a temperature at which the weight loss of the sample used reached 5%. In addition, the glass transition temperature (Tg) was measured by using a differential scanning calorimeter ("DSC220" manufactured by SII NanoTechnology Inc.) under a nitrogen gas flow (under a nitrogen atmosphere) under conditions of a rate of temperature rise of 10° C./min from room temperature (25° C.) and a rate of temperature drop of 30° C./min. In addition, the thermal decomposition temperature (Td) was measured by using a TG/DTA 220 thermogravimetric analyzer (manufactured by SII NanoTechnology Inc.) under a nitrogen atmosphere under a condition of a rate of temperature rise of 10° C./min. The intrinsic viscosity [η] was, as mentioned above, measured by using "KINEMATIC VISCOMETER TV-5S" manufactured by THOMAS SCI- ENTIFIC CO., under a temperature condition of 30° C., while a measurement sample having a concentration of 0.5 g/dL and using N,N-dimethylacetamide as a solvent was used. Each molecular weight (Mw or Mn) and the molecular weight distribution (Mw/Mn) were determined by measurement using a gel permeation chromatograph (GPC, manufactured by Tosoh Corporation, trade name: HLC-8020; Four columns: manufactured by Tosoh Corporation, trade name: TSK gel GMH$_{HR}$, solvent: tetrahydrofuran (THF)), and converting the obtained data in terms of polystyrene.

Synthesis Example 1

First, to a 100-ml two-necked flask, 6.83 g of a 50% by mass aqueous dimethylamine solution (dimethylamine: 75.9 mmol) was added. Next, to a 100-ml dropping funnel, 8.19 g of a 35% by mass aqueous solution of hydrochloric acid (hydrogen chloride: 78.9 mmol) was added. Subsequently, the dropping funnel was set to the two-necked flask, and the aqueous solution of hydrochloric acid was added dropwise to the aqueous dimethylamine solution under ice-cooling. Thus, dimethylamine hydrochloride was prepared in the two-necked flask. Next, to the two-necked flask, 2.78 g (92.4 mmol) of paraformaldehyde and 2.59 g (30.8 mmol) of cyclopentanone were further added. Subsequently, a bulb condenser was set to the two-necked flask, and then the inside of the two-necked flask was replaced with nitrogen. Thereafter, the two-necked flask was immersed in an oil bath of 90° C., and heated for 3 hours with stirring. Thus, a reaction liquid was obtained which contained a Mannich base (a compound represented by the general formula (I-2) described in the reaction formula (I), in which n was 2, $R^2$ and $R^3$ were all hydrogen atoms, Rs were each a methyl group, and $X^-$ was a chlorine ion). Note that the thus obtained reaction liquid was subjected to a gas chromatography analysis (GC analysis: a detector manufactured by Agilent Technologies under the trade name of "6890N" was used). As a result, it was found that the conversion of cyclopentanone was 99%.

Next, the reaction liquid in the two-necked flask was cooled to 50° C. Then, to the reaction liquid, methyl cellosolve (50 ml), 1.12 g (12.4 mmol) of a 50% by mass aqueous dimethylamine solution, and 7.13 g (108 mmol) of cyclopentadiene were added. Thus, a mixture liquid was obtained. Subsequently, the inside of the two-necked flask was replaced with nitrogen, then the two-necked flask was immersed in an oil bath of 120° C., and the mixture liquid was heated for 90 minutes. Then, the mixture liquid was cooled to room temperature (25° C.). Next, the mixture liquid was transferred to a 200-ml separatory funnel, and a first extraction operation was conducted by adding n-heptane (80 ml) to the mixture liquid, and then recovering a n-heptane layer from the mixture liquid. Next, a second extraction operation was conducted by adding again n-heptane (40 ml) to a methyl cellosolve layer remaining after the recovery of the n-heptane layer from the mixture liquid, and then recovering a n-heptane layer therefrom. Then, the n-heptane layers obtained by the first and second extraction operations were mixed with each other. Thus, a n-heptane extraction liquid was obtained.

Next, the n-heptane extraction liquid was washed once with 5% by mass aqueous NaOH (25 ml), and then once with 5% by mass aqueous hydrochloric acid (25 ml). Subsequently, the n-heptane extraction liquid washed with the aqueous hydrochloric acid was washed once with 5% by mass aqueous sodium hydrogen carbonate (25 ml), and further once with saturated aqueous sodium chloride (25 ml). Subsequently, the thus washed n-heptane extraction liquid was dried over anhydrous magnesium sulfate, and then the anhydrous magnesium sulfate was filtered off. Thus, a filtrate was obtained. Subsequently, the obtained filtrate was concentrated by using an evaporator, and n-heptane was evaporated. Thus, 7.4 g of a crude product (5-norbornene-2-spiro-α-cyclopentanone-α'-spiro-2"-5"-norbornene) was obtained (percentage yield of crude: 99%). Next, the thus obtained crude product was subjected to Kugelrohr distillation (boiling point: 105° C./0.1 mmHg), and 4.5 g of 5-norbornene-2-spiro-α-cyclopentanone-α'-spiro-2"-5"-norbornene was obtained (percentage yield: 610).

Figure 2:
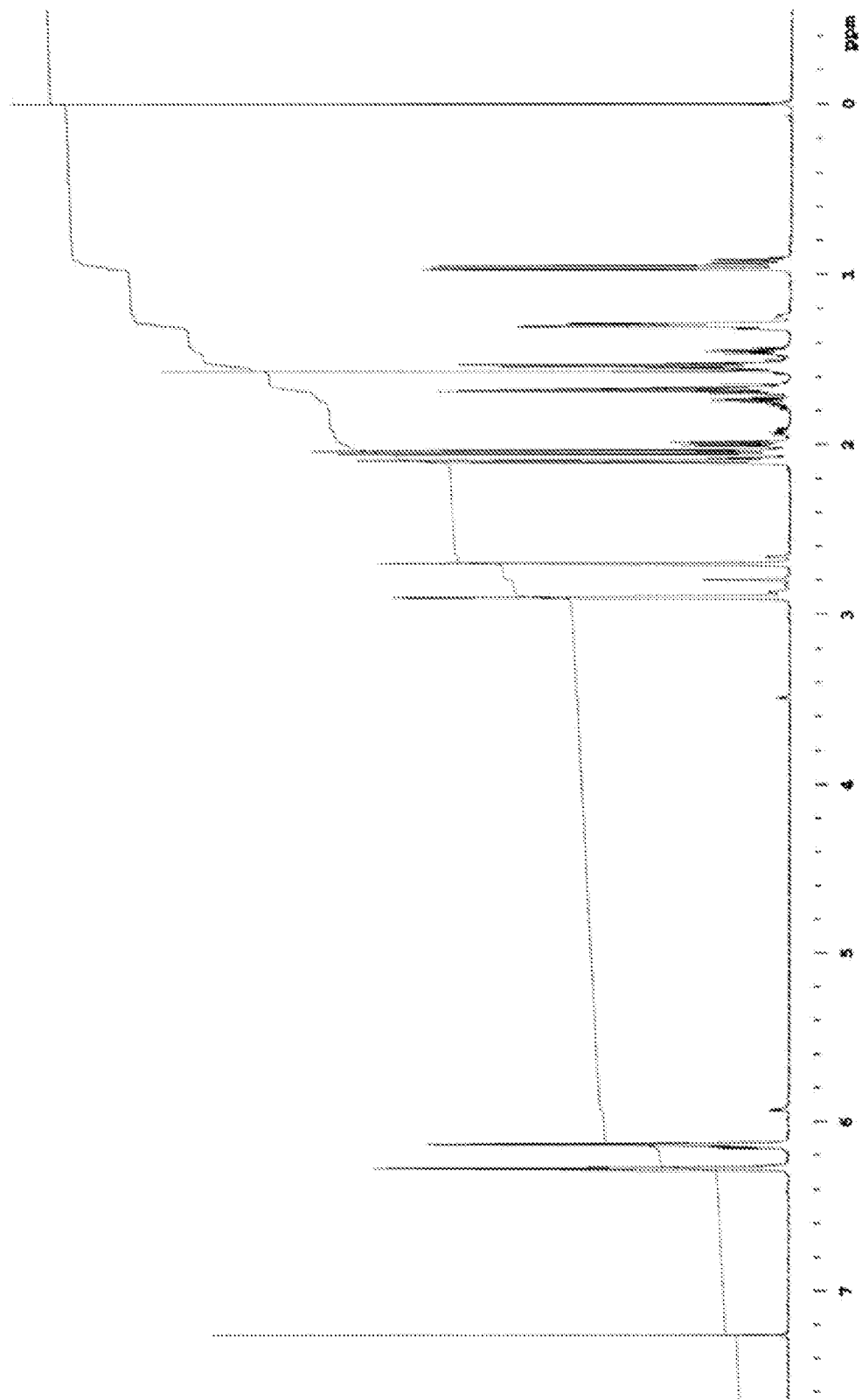
FIG. 2 is a graph showing a $^1$H-NMR (CDCl$_3$) spectrum of the 5-norbornene-2-spiro-α-cyclopentanone-α'-spiro-2''-5''-norbornene obtained in Synthesis Example 1.
Figure 3:
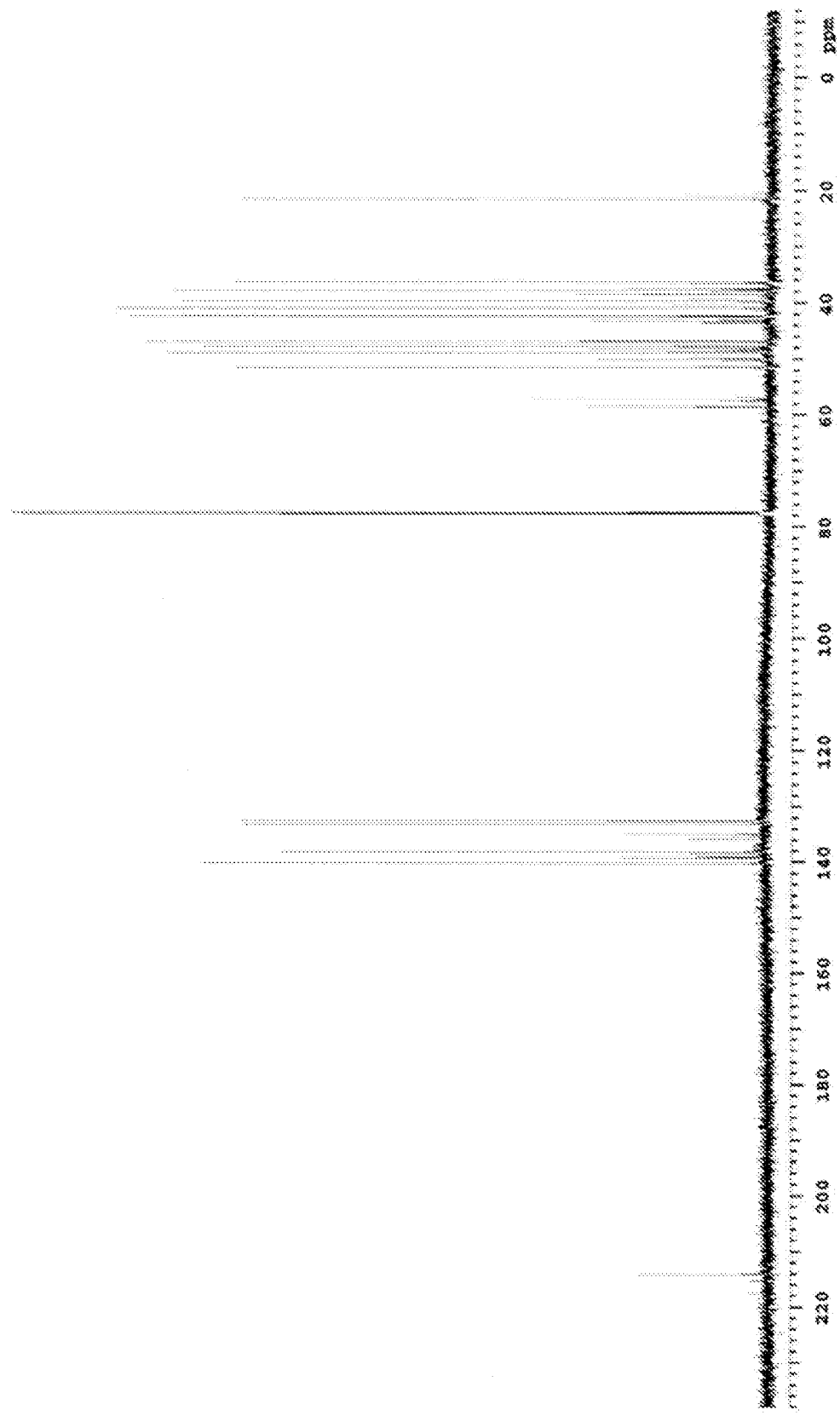
FIG. 3 is a graph showing a $^{13}$C-NMR (CDCl$_3$) spectrum of the 5-norbornene-2-spiro-α-cyclopentanone-α'-spiro-2''-5''-norbornene obtained in Synthesis Example 1.

To confirm the structure of the thus obtained compound, IR and NMR ($^1$H-NMR and $^{13}$C-NMR) measurements were conducted. FIG. 1 shows an IR spectrum of the thus obtained compound, FIG. 2 shows a $^1$H-NMR (CDCl$_3$) spectrum thereof, and FIG. 3 shows a $^{13}$C-NMR (CDCl$_3$) spectrum thereof. From the results shown in FIGS. 1 to 3, the obtained compound was confirmed to be 5-norbornene-2-spiro-α-cyclopentanone-α'-spiro-2"-5"-norbornene (also referred to as "5-norbornene-2-spiro-2'-cyclopentanone-5'-spiro-2"-5"-norbornene") represented by the following general formula (13):

[Chem. 24]

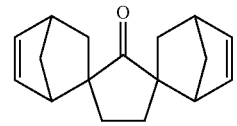

(13)

In addition, from the results shown in FIGS. 1 to 3, it was found that the ratio (endo/exo) between the endo isomer and the exo isomer was 10/90 in the 5-norbornene-2-spiro-α-cyclopentanone-α'-spiro-2"-5"-norbornene.

Synthesis Example 2

First, to a 100-ml two-necked flask, 6.83 g of a 50% by mass aqueous dimethylamine solution (dimethylamine: 75.9 mmol) was added. Next, to a 100-ml dropping funnel, 8.19 g of a 35% by mass aqueous solution of hydrochloric acid (hydrogen chloride: 78.9 mmol) was added. Subsequently, the dropping funnel was set to the two-necked flask, and the aqueous solution of hydrochloric acid was added dropwise to the aqueous dimethylamine solution under ice-cooling. Thus, dimethylamine hydrochloride was prepared in the two-necked flask. Next, to the two-necked flask, 2.78 g (92.4 mmol) of paraformaldehyde and 3.02 g (30.8 mmol) of cyclohexanone were further added. Subsequently, a bulb condenser was set to the two-necked flask, and then the inside of the two-necked flask was replaced with nitrogen. Thereafter, the two-necked flask was immersed in an oil bath of 90° C., and heated for 4 hours with stirring. Thus, a reaction liquid was obtained which contained a Mannich base (a compound represented by the general formula (I-2) described in the reaction formula (I), in which n was 3, $R^2$ and $R^3$ were all hydrogen atoms, Rs were each a methyl group, and $X^-$ was a chlorine ion). Note that the thus obtained reaction liquid was subjected to a GC analysis in the same manner as in Synthesis Example 1. As a result, it was found that the conversion of cyclohexanone was 99%.

Next, the reaction liquid in the two-necked flask was cooled to 50° C. Then, to the reaction liquid, methyl cellosolve (50 ml), 1.12 g (12.4 mmol) of a 50% by mass aqueous dimethylamine solution, and 7.13 g (108 mmol) of cyclopentadiene were added. Thus, a mixture liquid was obtained. Subsequently, the inside of the two-necked flask was replaced with nitrogen, then the two-necked flask was immersed in an oil bath of 120° C., and the mixture liquid was heated for 90 minutes. Then, the mixture liquid was cooled to room temperature (25° C.). Next, the mixture liquid was transferred to a 200-ml separatory funnel, and a first extraction operation was conducted by adding n-heptane (80 ml) to the mixture liquid, and recovering a n-heptane layer from the mixture liquid. Next, a second extraction operation was conducted by adding again n-heptane (40 ml) to a methyl cellosolve layer remaining after the recovery of the n-heptane layer from the mixture liquid, and then recovering a n-heptane layer therefrom. Then, the n-heptane layers obtained by the first and second extraction operations were mixed with each other. Thus, a n-heptane extraction liquid was obtained.

Next, the n-heptane extraction liquid was washed once with 5% by mass aqueous NaOH (25 ml), and then once with 5% by mass aqueous hydrochloric acid (25 ml). Subsequently, the n-heptane extraction liquid washed with the aqueous hydrochloric acid was washed once with 5% by mass aqueous sodium hydrogen carbonate (25 ml), and further once with saturated aqueous sodium chloride (25 ml). Subsequently, the thus washed n-heptane extraction liquid was dried over anhydrous magnesium sulfate, and then the anhydrous magnesium sulfate was filtered off. Thus, a filtrate was obtained. Subsequently, the obtained filtrate was concentrated by using an evaporator, and n-heptane was evaporated. Thus, 7.8 g of a crude product (5-norbornene-2-spiro-α-cyclohexanone-α'-spiro-2"-5"-norbornene) was obtained (percentage yield of crude: 99%). Next, the thus obtained crude product was subjected to Kugelrohr distillation (boiling point: 120 to 145° C./0.1 mmHg), and 4.4 g of 5-norbornene-2-spiro-α-cyclohexanone-α'-spiro-2"-5"-norbornene was obtained (percentage yield: 56%).

Figure 4:
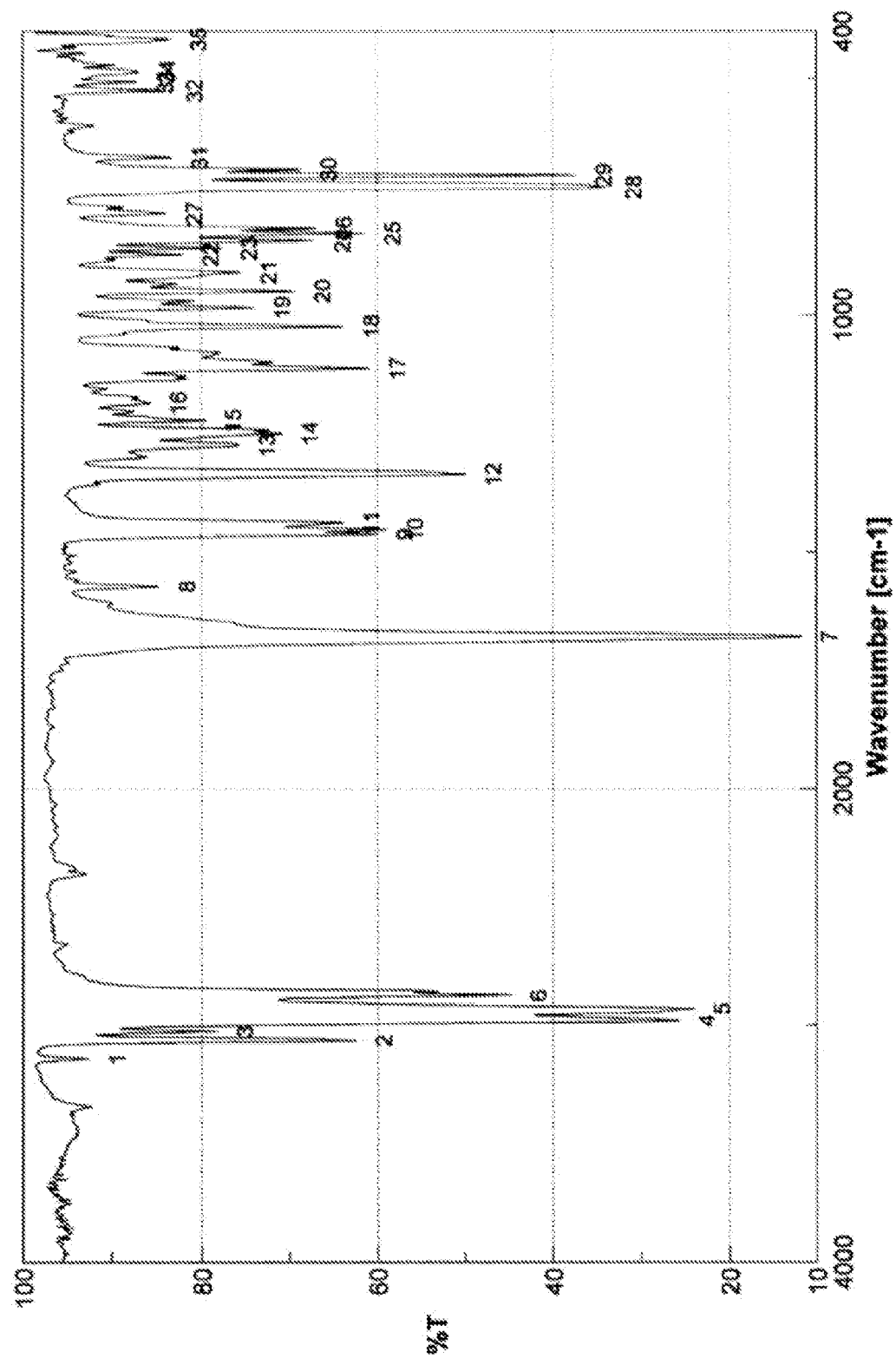
FIG. 4 is a graph showing an IR spectrum of 5-norbornene-2-spiro-α-cyclohexanone-α'-spiro-2''-5''-norbornene obtained in Synthesis Example 2.
Figure 5:
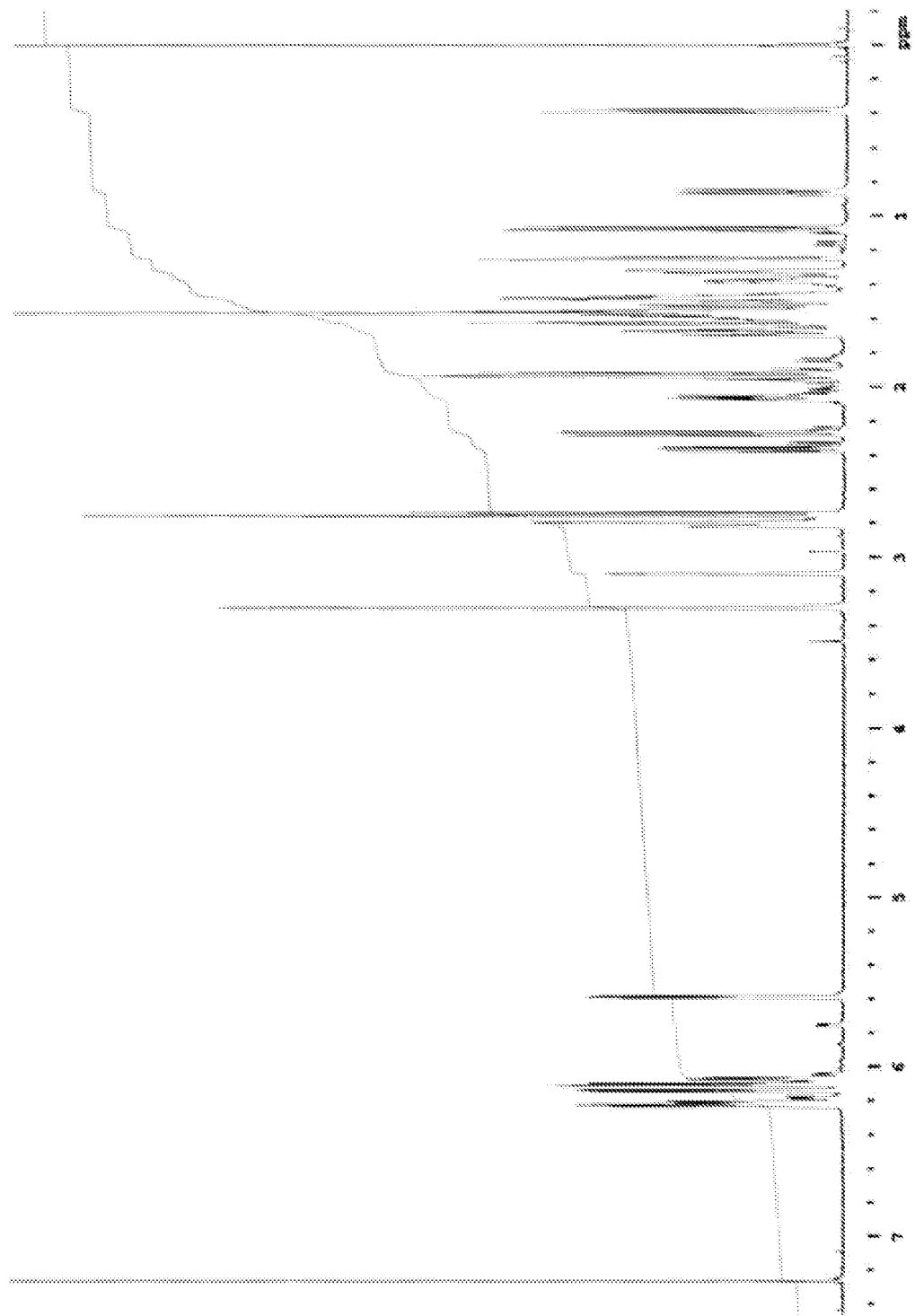
FIG. 5 is a graph showing a $^1$H-NMR (CDCl$_3$) spectrum of the 5-norbornene-2-spiro-α-cyclohexanone-α'-spiro-2''-5''-norbornene obtained in Synthesis Example 2.
Figure 6:
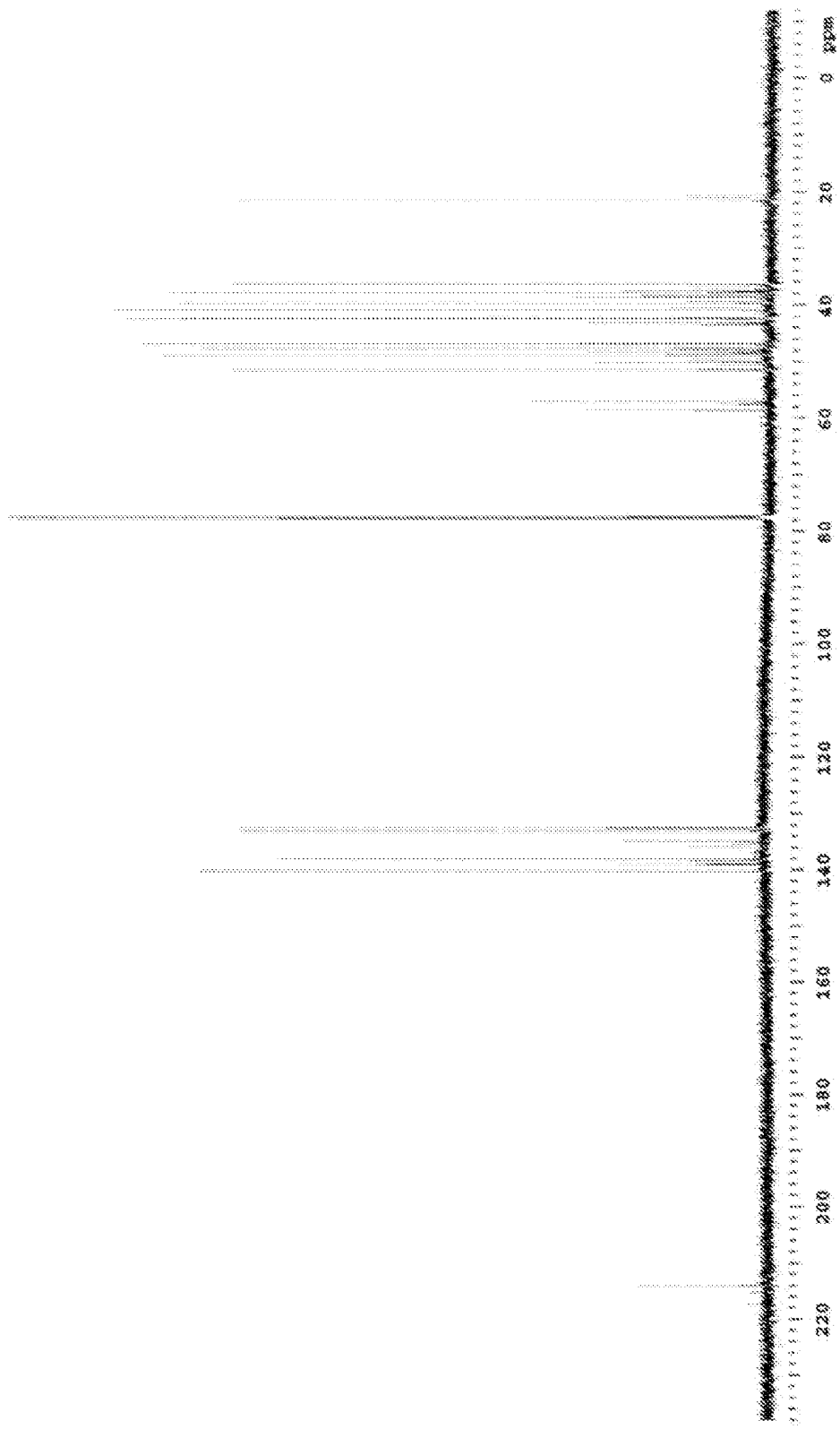
FIG. 6 is a graph showing a $^{13}$C-NMR (CDCl$_3$) spectrum of the 5-norbornene-2-spiro-α-cyclohexanone-α'-spiro-2''-5''-norbornene obtained in Synthesis Example 2.

To confirm the structure of the thus obtained compound, IR and NMR ($^1$H-NMR and $^{13}$C-NMR) measurements were conducted. FIG. 4 shows an IR spectrum of the thus obtained compound, FIG. 5 shows a $^1$H-NMR (CDCl$_3$) spectrum thereof, and FIG. 6 shows a $^{13}$C-NMR (CDCl$_3$) spectrum thereof. From the results shown in FIGS. 4 to 6, the obtained compound was confirmed to be 5-norbornene-2-spiro-α-cyclohexanone-α'-spiro-2"-5"-norbornene (also referred to as "5-norbornene-2-spiro-2'-cyclohexanone-6'-spiro-2"-5"-norbornene") represented by the following general formula (14):

[Chem. 25]

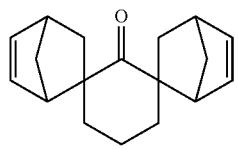

(14)

It was found that cis and trans isomers of the spiro condensation ring had an endo isomer and an exo isomer, in the 5-norbornene-2-spiro-α-cyclohexanone-α'-spiro-2"-5"-norbornene, and it was found based on the number of olefins that the 5-norbornene-2-spiro-α-cyclohexanone-α'-spiro-2"-5"-norbornene was a mixture of six isomers.

Example 1

A mixture liquid was obtained by introducing the 5-norbornene-2-spiro-α-cyclopentanone-α'-spiro-2"-5"-norbornene obtained in Synthesis Example 1 (2.00 g, 8.32 mmol), methanol (800 ml), sodium acetate (7.52 g, 91.67 mmol), CuCl$_2$(II) (8.95 g, 66.57 mmol), and PdCl$_2$ (34 mg, 0.19 mmol) into a 2-L four-necked flask. Then, the atmosphere inside the flask was replaced with nitrogen. Next, a reaction liquid was obtained by vigorously stirring the mixture liquid for 1 hour under conditions of 25° C. and 0.1 MPa, with carbon monoxide (3.2 L) being introduced into the flask by using a balloon. Subsequently, carbon monoxide was removed from the inside of the flask, and methanol was completely removed from the reaction liquid by concentrating the reaction liquid by use of an evaporator. Thus, a reaction product was obtained. After that, chloroform (500 ml) was added to the reaction product, followed by filtration through Celite. Then, the filtrate was subjected to separation using a saturated aqueous solution of sodium hydrogen carbonate, and the organic layer was collected. Then, a drying agent (anhydrous magnesium sulfate) was added to the organic layer, which was then stirred for 2 hours. Subsequently, the drying agent was separated from the organic layer by filtration, and the organic layer was concentrated by using an evaporator. Thus, norbornane-2-spiro-α-cyclopentanone-α'-spiro-2"-norbornane-5,5",6,6"-tetracarboxylic acid tetramethyl ester was obtained (yield: 3.93 g, percentage yield: 99.1%).

Figure 7:
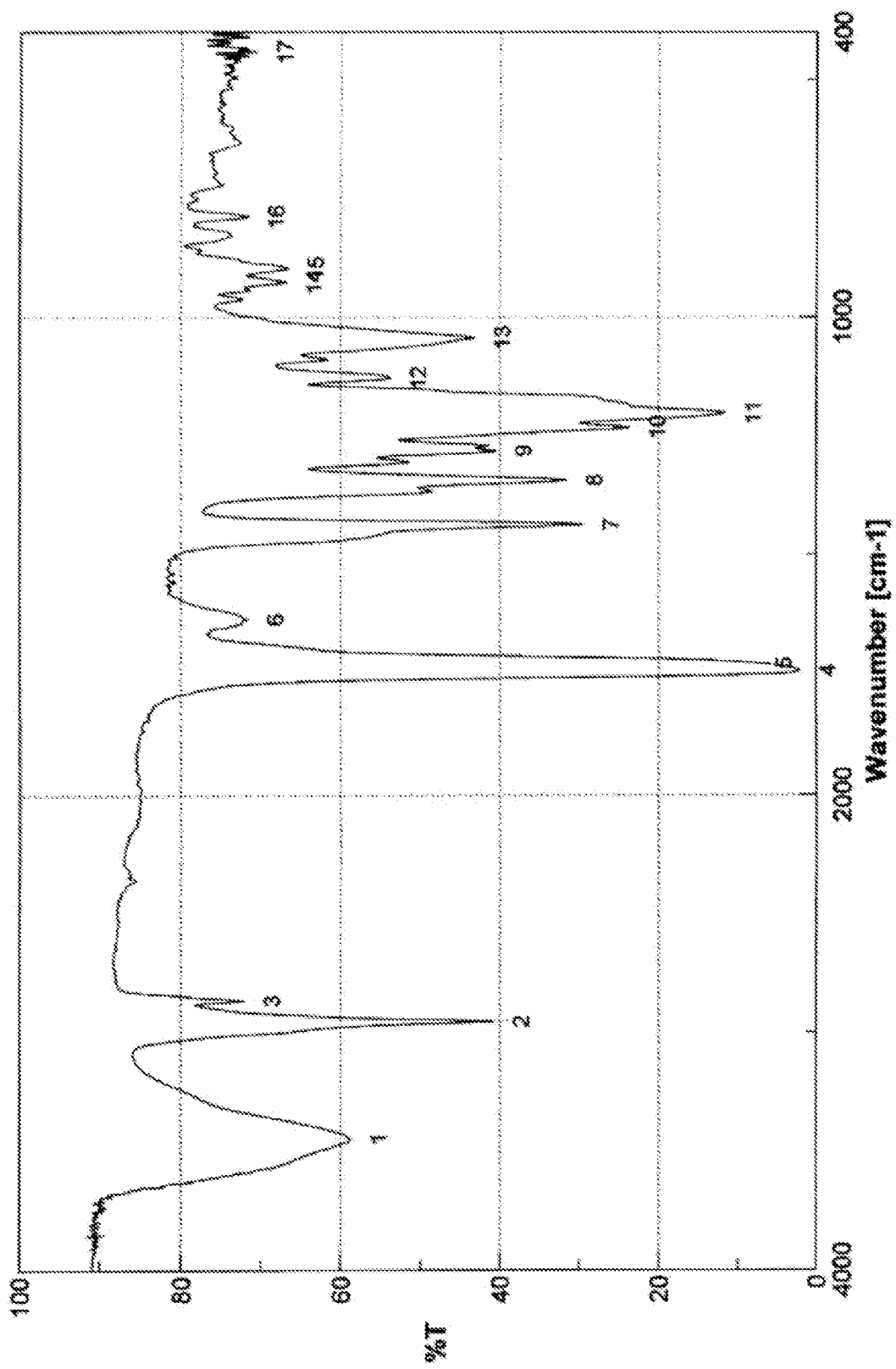
FIG. 7 is a graph showing an IR spectrum of norbornane-2-spiro-α-cyclopentanone-α'-spiro-2''-norbornane-5,5'',6,6''-tetracarboxylic acid tetramethyl ester obtained in Example 1.
Figure 8:
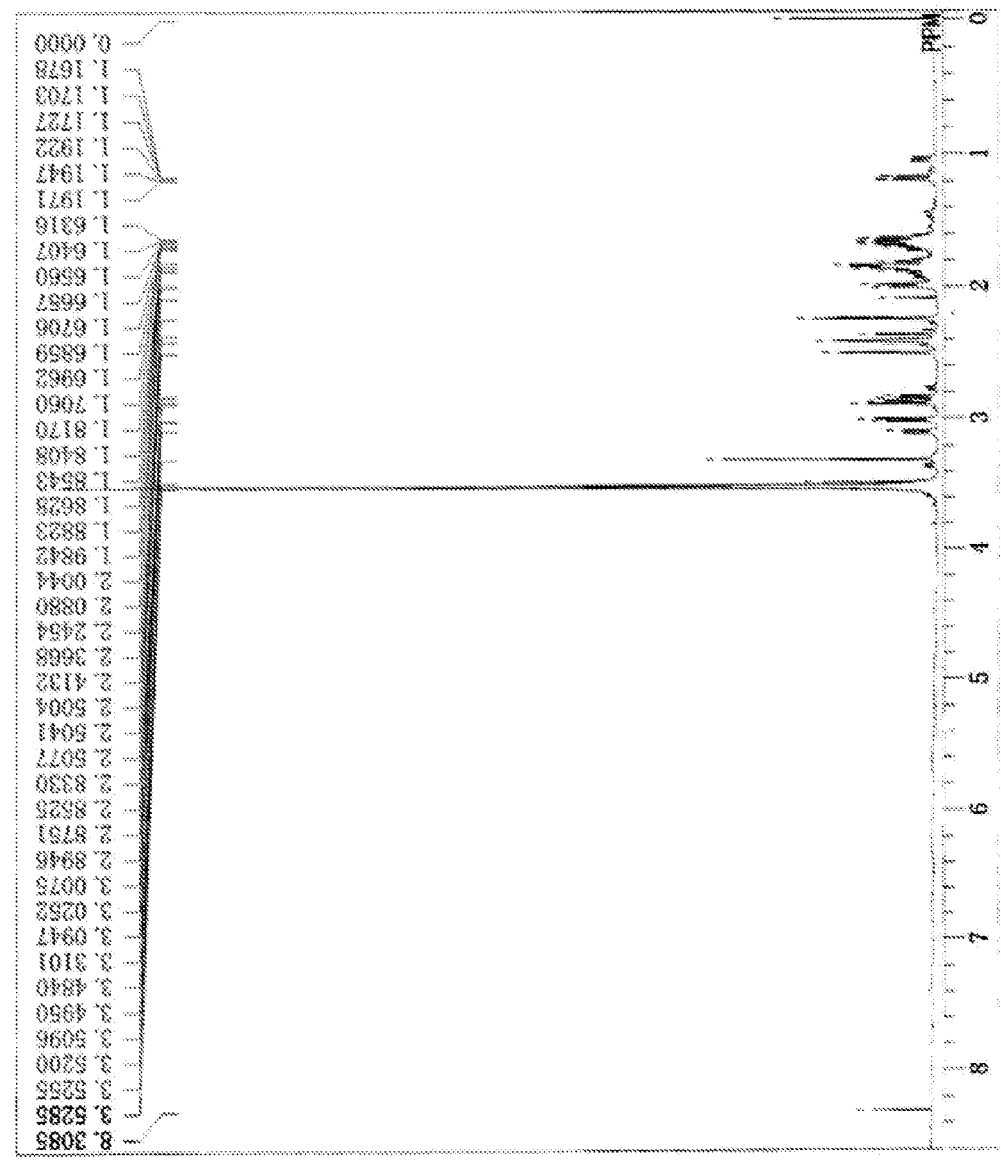
FIG. 8 is a graph showing a $^1$H-NMR (DMSO-d$^6$) spectrum of the norbornane-2-spiro-α-cyclopentanone-α'-spiro-2''-norbornane-5,5'',6,6''-tetracarboxylic acid tetramethyl ester obtained in Example 1.
Figure 9:
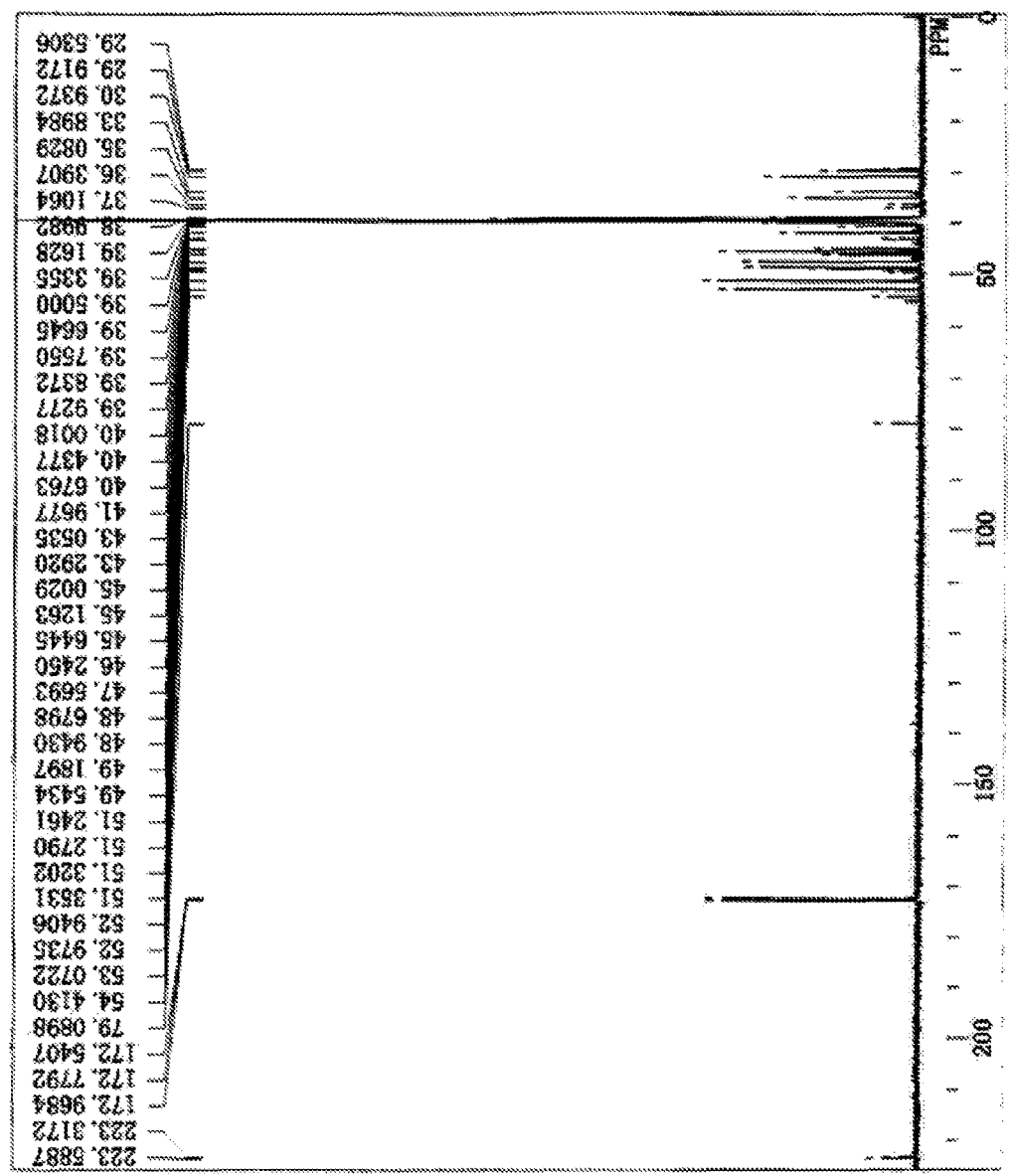
FIG. 9 is a graph showing a $^{13}$C-NMR (DMSO-d$^6$) spectrum of the norbornane-2-spiro-α-cyclopentanone-α'-spiro-2''-norbornane-5,5'',6,6''-tetracarboxylic acid tetramethyl ester obtained in Example 1.

To confirm the structure of the thus obtained compound, IR and NMR measurements were conducted. FIG. 7 shows an IR spectrum of the thus obtained compound, FIG. 8 shows a $^1$H-NMR (DMSO-d$^6$) spectrum thereof, and FIG. 9 shows a $^{13}$C-NMR (DMSO-d$^6$) spectrum thereof. As is apparent from the results shown in FIGS. 7 to 9, the obtained compound was confirmed to be norbornane-2-spiro-α-cyclopentanone-α'-spiro-2"-norbornane-5,5",6,6"-tetracarboxylic acid tetramethyl ester represented by the following general formula (15):

[Chem. 26]

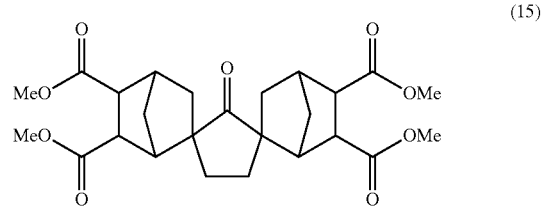

(15)

Example 2

A mixture liquid was obtained by introducing the norbornane-2-spiro-α-cyclopentanone-α'-spiro-2"-norbornane-5, 5",6,6"-tetracarboxylic acid tetramethyl ester obtained in Example 1 (1.93 g, 4.05 mmol), formic acid (14 ml, 222 mmol), and p-toluenesulfonic acid (anhydrous, 0.1 g, 0.306 mmol) into a 100-ml three-necked flask, followed by heating under reflux for 6 hours in an oil bath of 120° C. Subsequently, the mixture liquid was concentrated by evaporation under reduced pressure such that the liquid amount of the mixture liquid was about halved. Thus, a liquid concentrate was obtained. After that, formic acid (7 ml, 111 mmol) was added to the liquid concentrate, followed by heating under reflux for 6 hours at 120° C. Then, the obtained mixture liquid was again concentrated by evaporation under reduced pressure such that the liquid amount of the mixture liquid was about halved. Thus, a liquid concentrate was obtained. Then, such an operation including addition of formic acid to the liquid concentrate and concentration of the liquid concentrate was further repeated three times in total. Then, formic acid (7 ml, 111 mmol) and acetic anhydride (18 ml, 127 mmol) were added to the obtained liquid concentrate, followed by heating under reflux for 3 hours at 120° C. Thus, a reaction liquid was obtained. Then, the obtained reaction liquid was concentrated to dryness by using an evaporator. Thus, a solid matter was obtained. Next, the thus obtained solid matter was washed by adding diethyl ether thereto. Thus, a gray crude product was obtained (1.56 g, quantitatively). Subsequently, the obtained crude product (0.1 g) was placed in a sublimation purification apparatus, and purified by sublimation at 250 to 270° C./1 mmHg for three and a half hours. Thus, 0.89 g of a white solid was obtained (percentage yield: 89.1%).

Figure 10:
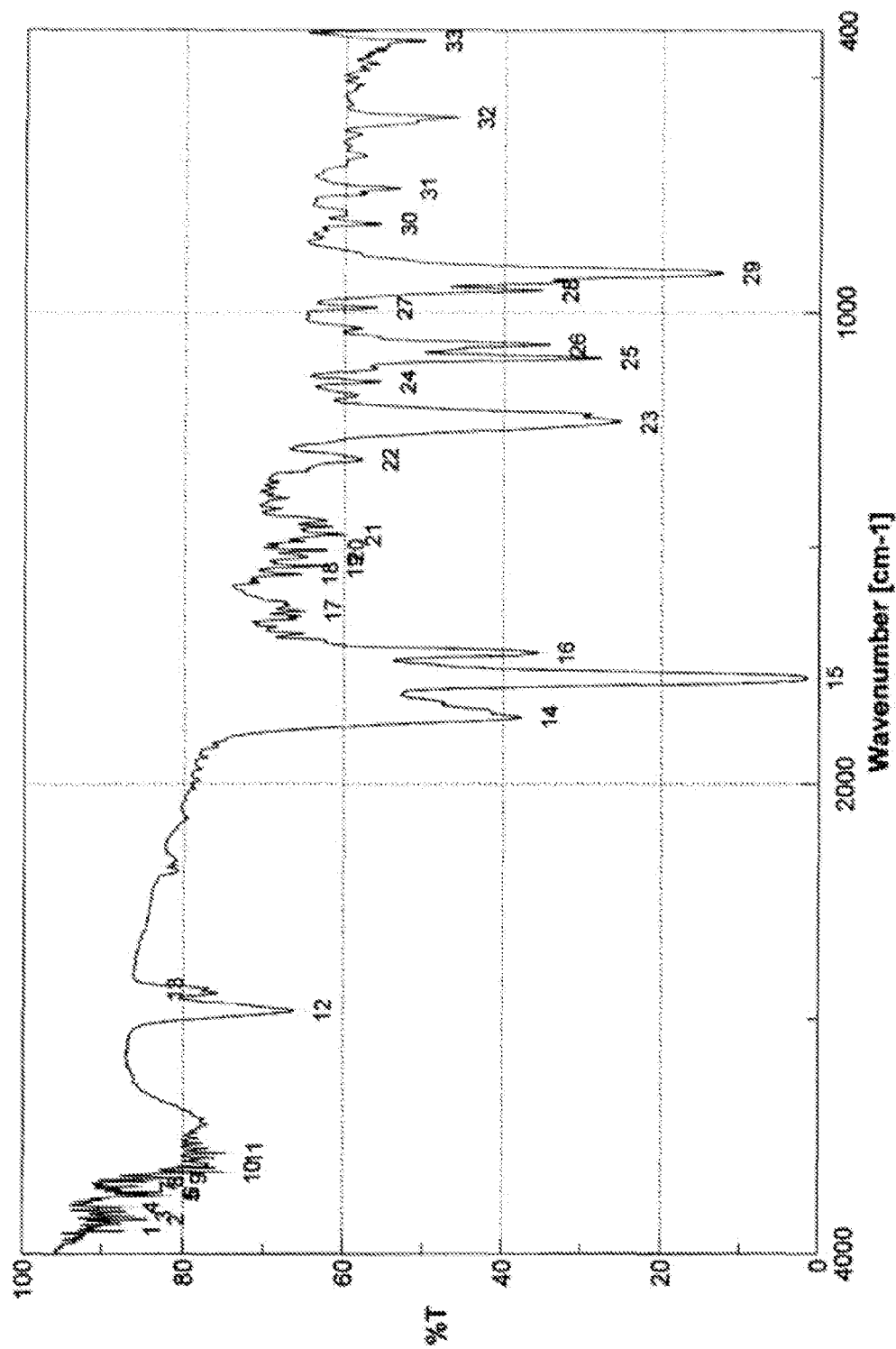
FIG. 10 is a graph showing an IR spectrum of norbornane-2-spiro-α-cyclopentanone-α'-spiro-2''-norbornane-5,5'',6,6''-tetracarboxylic dianhydride obtained in Example 2.
Figure 11:
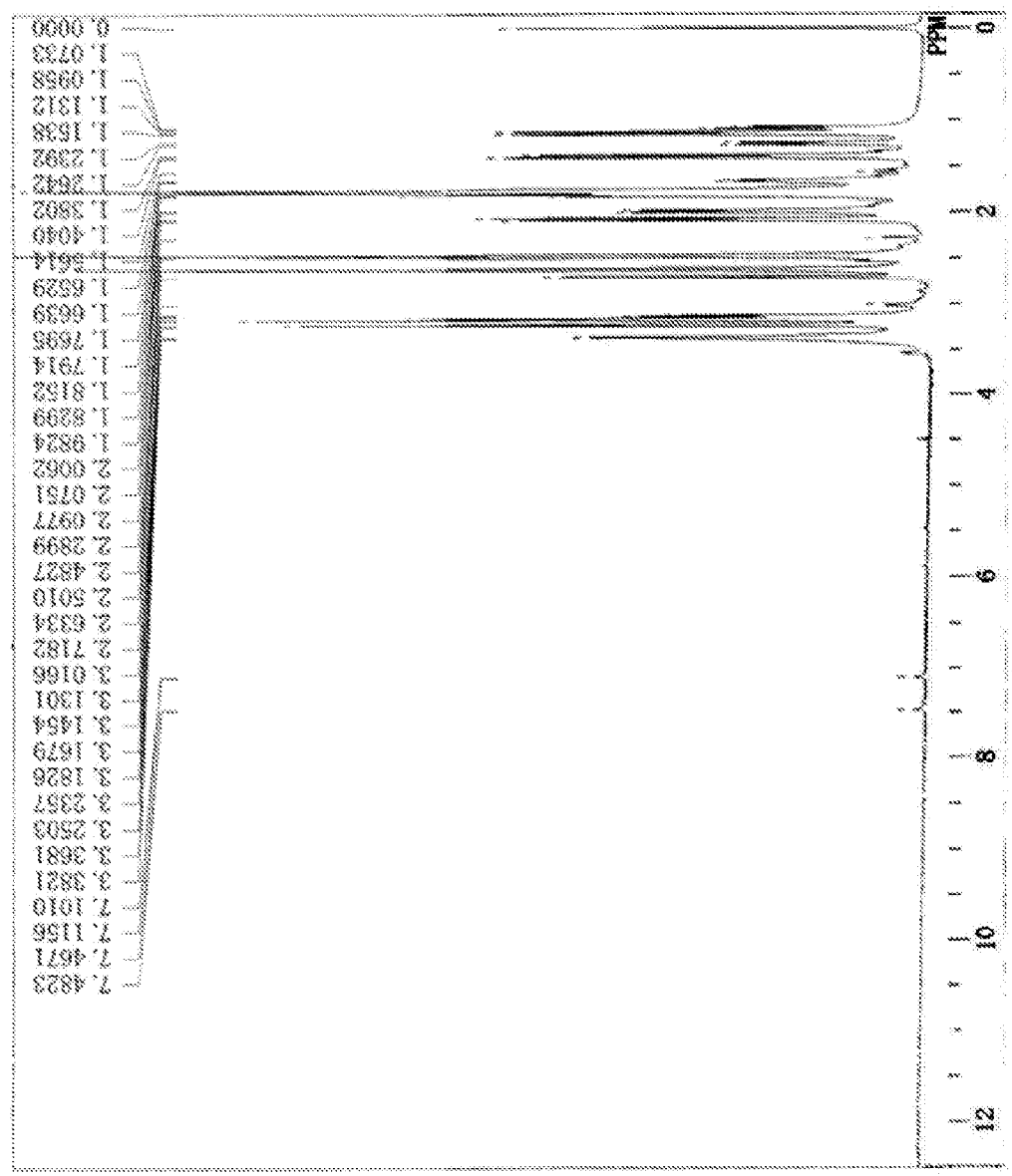
FIG. 11 is a graph showing a $^1$H-NMR (DMSO-d$^6$) spectrum of the norbornane-2-spiro-α-cyclopentanone-α'-spiro-2''-norbornane-5,5'',6,6''-tetracarboxylic dianhydride obtained in Example 2.
Figure 12:
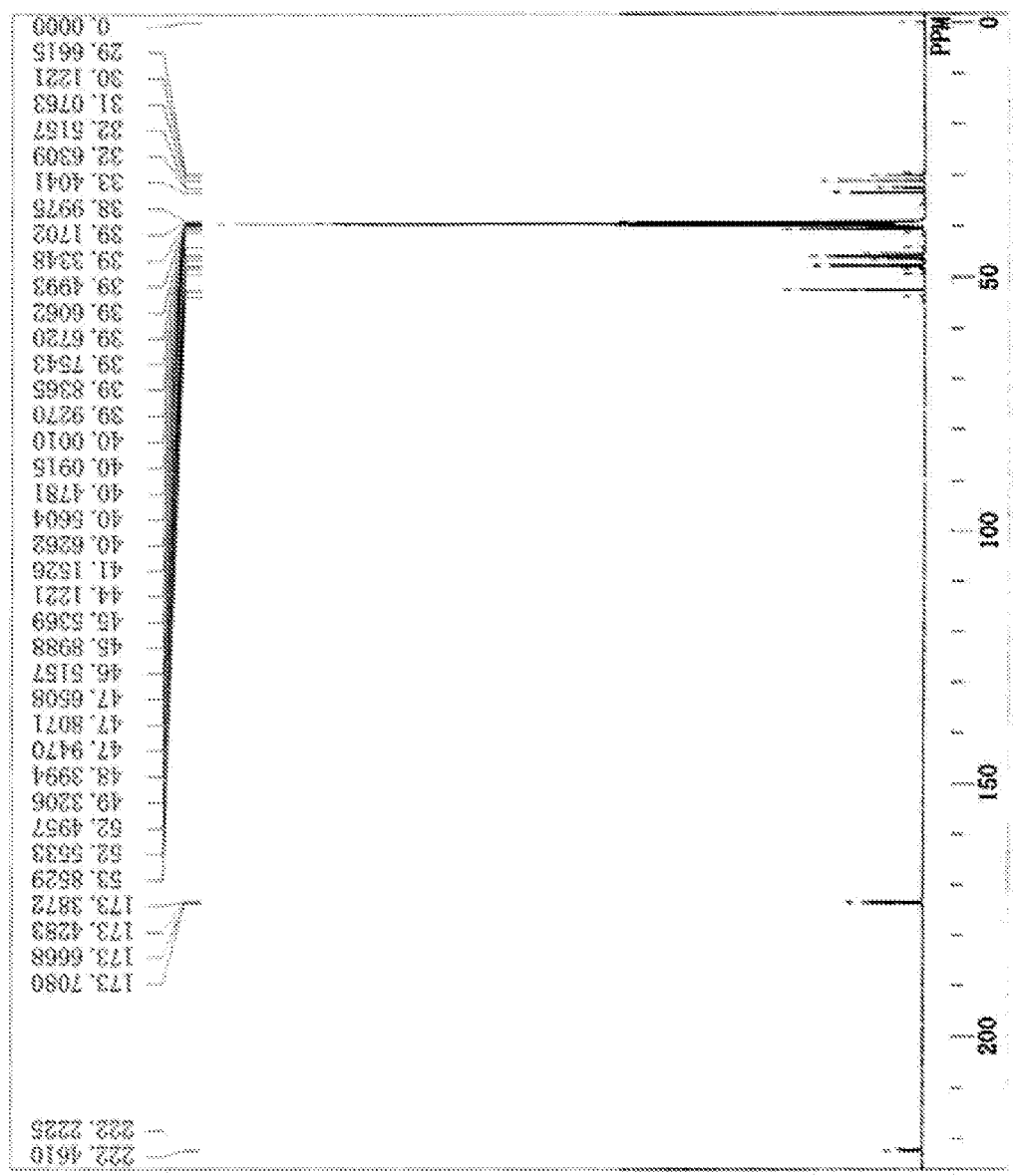
FIG. 12 is a graph showing a $^{13}$C-NMR (DMSO-d$^6$) spectrum of the norbornane-2-Spiro-α-cyclopentanone-α'-spiro-2''-norbornane-5,5'',6,6''-tetracarboxylic dianhydride obtained in Example 2.

To confirm the structure of the thus obtained compound, IR and NMR measurements were conducted. FIG. 10 shows an IR spectrum, FIG. 11 shows a $^1$H-NMR (DMSO-d$^6$) spectrum, and FIG. 12 shows a $^{13}$C-NMR (DMSO-d$^6$) spectrum. As is apparent from the results shown in FIGS. 10 to 12, the obtained compound was confirmed to be norbornane-2-spiro-α-cyclopentanone-α'-spiro-2"-norbornane-5,5",6,6"-tetracarboxylic dianhydride (also referred to as "norbornane-2-spiro-2'-cyclopentanone-5'-spiro-2"-norbornane-5,5",6,6"-tetracarboxylic dianhydride") represented by the following general formula (16):

[Chem. 27]

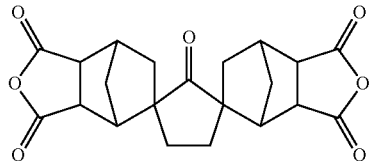

(16)

Example 3

A mixture liquid was obtained by introducing the 5-norbornene-2-spiro-α-cyclohexanone-α'-spiro-2"-5"-norbornene obtained in Synthesis Example 2 (2.12 g, 8.32 mmol), methanol (800 ml), sodium acetate (7.52 g, 91.67 mmol), CuCl$_2$(II) (8.95 g, 66.57 mmol), and PdCl$_2$ (34 mg, 0.19 mmol) into a 2-L four-necked flask. Then, the atmosphere inside the flask was replaced with nitrogen. Next, a reaction liquid was obtained by vigorously stirring the mixture liquid for 1 hour under conditions of 25° C. and 0.1 MPa, with carbon monoxide (3.2 L) being introduced into the flask by using a balloon. Subsequently, carbon monoxide was removed from the inside of the flask, and methanol was completely removed from the reaction liquid by concentrating the reaction liquid by use of an evaporator. Thus, a reaction product was obtained. After that, chloroform (500 ml) was added to the reaction product, followed by filtration through Celite. Then, the filtrate was subjected to separation using a saturated aqueous solution of sodium hydrogen carbonate, and the organic layer was collected. Then, a drying agent (anhydrous magnesium sulfate) was added to the organic layer, which was then stirred for 2 hours. Subsequently, the drying agent was separated from the organic layer by filtration, and the organic layer was concentrated by using an evaporator. Thus, norbornane-2-spiro-α-cyclohexanone-α'-spiro-2"-norbornane-5,5",6,6"-tetracarboxylic acid tetramethyl ester was obtained (yield: 4.04 g, percentage yield: 99.0%).

Figure 13:
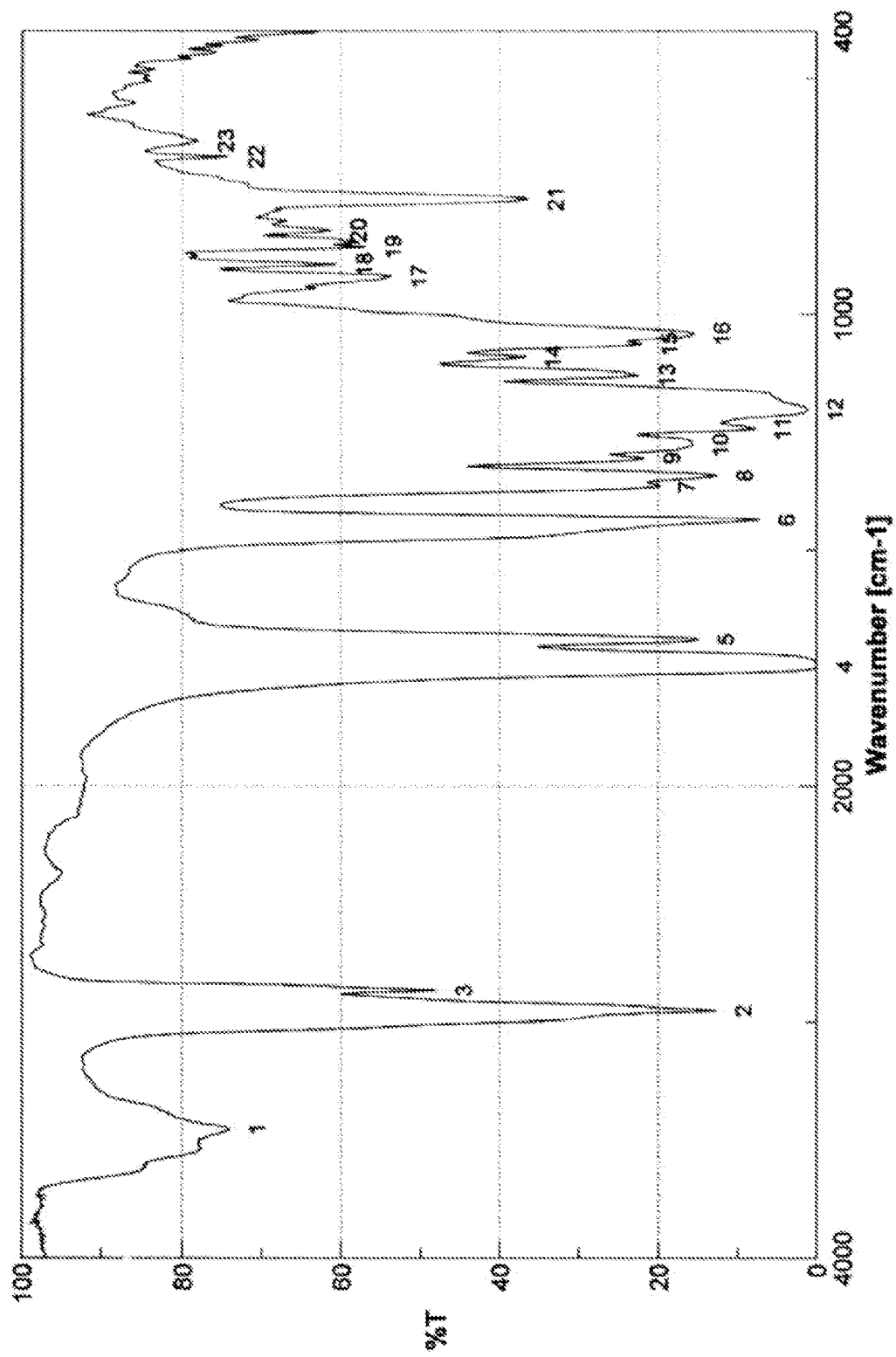
FIG. 13 is a graph showing an IR spectrum of norbornane-2-spiro-α-cyclohexanone-α'-spiro-2''-norbornane-5,5'',6,6''-tetracarboxylic acid tetramethyl ester obtained in Example 3.
Figure 14:
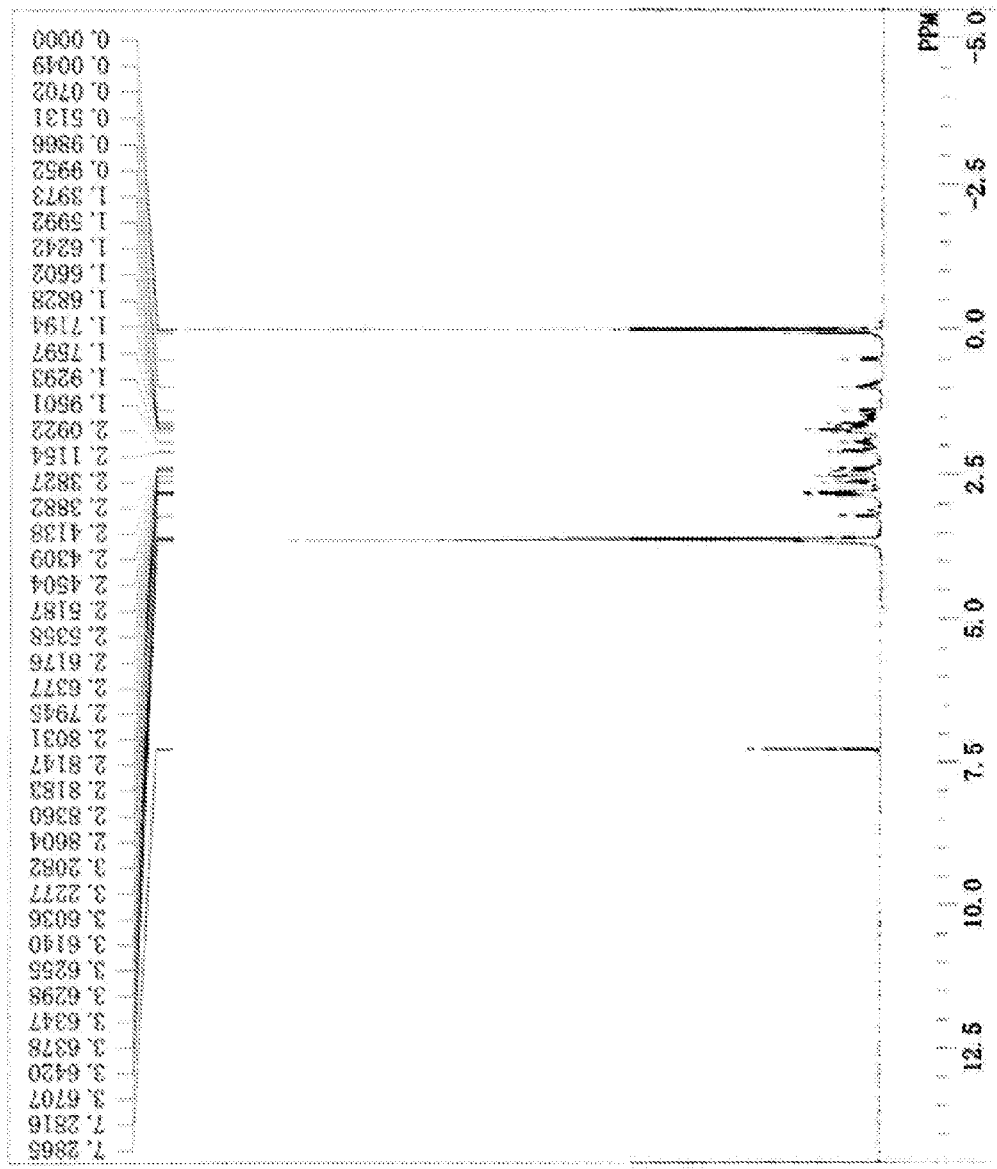
FIG. 14 is a graph showing a $^1$H-NMR (CDCl$_3$) spectrum of the norbornane-2-spiro-α-cyclohexanone-α'-spiro-2"-norbornane-5,5",6,6"-tetracarboxylic acid tetramethyl ester obtained in Example 3.
Figure 15:
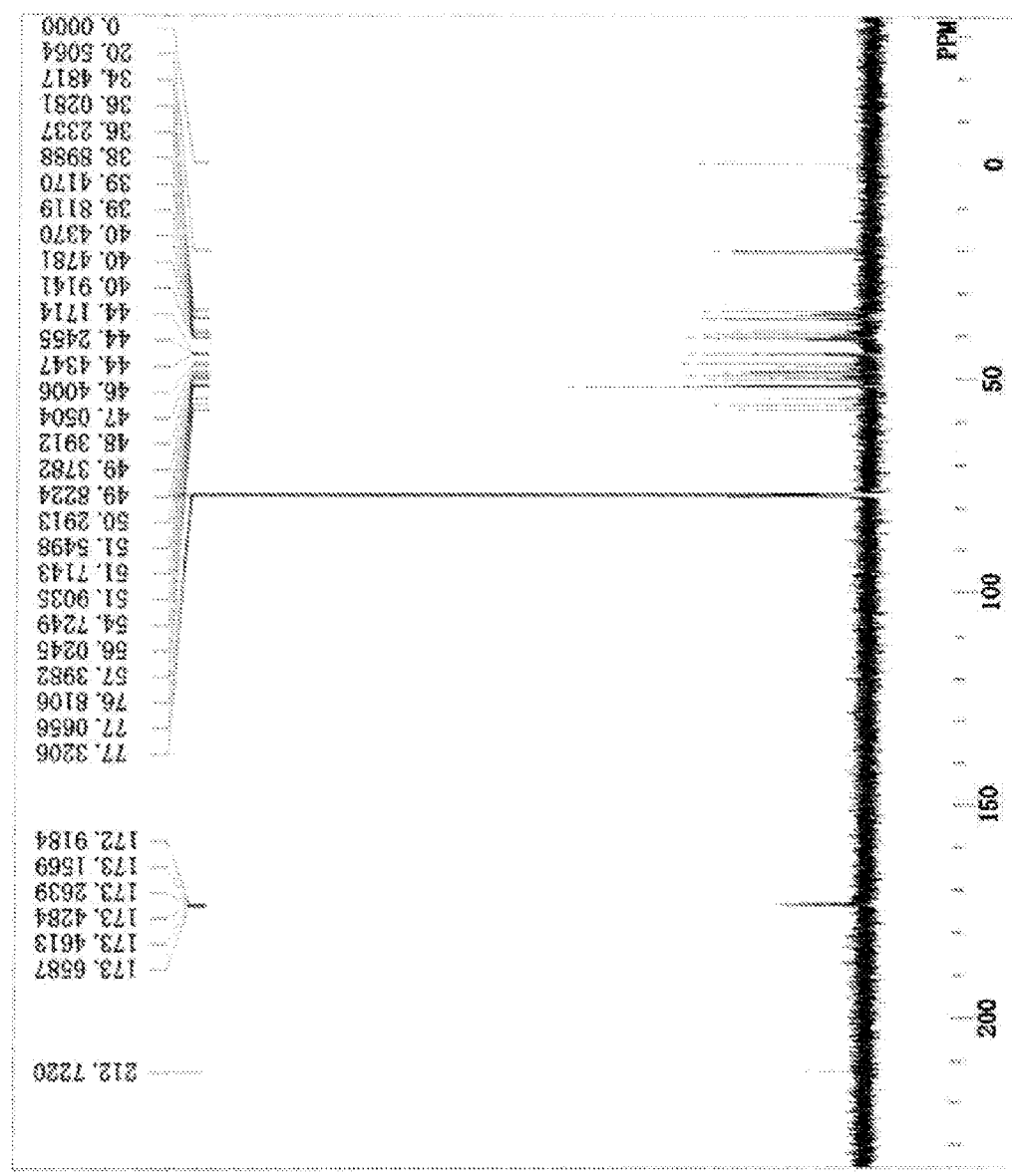
FIG. 15 is a graph showing a $^{13}$C-NMR (CDCl$_3$) spectrum of the norbornane-2-spiro-α-cyclohexanone-α'-spiro-2"-norbornane-5,5",6,6"-tetracarboxylic acid tetramethyl ester obtained in Example 3.

To confirm the structure of the thus obtained compound, IR and NMR measurements were conducted. FIG. 13 shows an IR spectrum of the thus obtained compound, FIG. 14 shows a $^1$H-NMR (CDCl$_3$) spectrum thereof, and FIG. 15 shows a $^{13}$C-NMR (CDCl$_3$) spectrum thereof. As is apparent from the results shown in FIGS. 13 to 15, the obtained compound was confirmed to be norbornane-2-spiro-α-cyclohexanone-α'-spiro-2"-norbornane-5,5",6,6"-tetracarboxylic acid tetramethyl ester represented by the following general formula (17):

[Chem. 28]

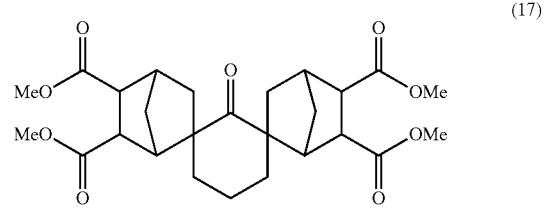

(17)

Example 4

A mixture liquid was obtained by introducing the norbornane-2-spiro-α-cyclohexanone-α'-spiro-2"-norbornane-5,5",6,6"-tetracarboxylic acid tetramethyl ester obtained in Example 3 (1.99 g, 4.05 mmol), formic acid (14 ml, 222 mmol), and p-toluenesulfonic acid (anhydrous, 0.1 g, 0.306 mmol) into a 100-ml three-necked flask, followed by heating under reflux for 6 hours in an oil bath of 120° C. Subsequently, the mixture liquid was concentrated by evaporation under reduced pressure such that the liquid amount of the mixture liquid was about halved. Thus, a liquid concentrate was obtained. After that, formic acid (7 ml, 111 mmol) was added to the liquid concentrate, followed by heating under reflux for 6 hours at 120° C. Then, the obtained mixture liquid was again concentrated by evaporation under reduced pressure such that the liquid amount of the mixture liquid was about halved. Thus, a liquid concentrate was obtained. Then, such an operation including addition of formic acid to the liquid concentrate and concentration of the liquid concentrate was further repeated three times in total. Then, formic acid (7 ml, 111 mmol) and acetic anhydride (18 ml, 127 mmol) were added to the obtained liquid concentrate, followed by heating under reflux for 3 hours at 120° C. Thus, a reaction liquid was obtained. Then, the obtained reaction liquid was concentrated to dryness by using an evaporator. Thus, a solid matter was obtained. Next, the thus obtained solid matter was washed by adding diethyl ether thereto. Thus, a gray crude product was obtained (1.61 g, quantitatively). Subsequently, the obtained crude product (0.1 g) was placed in a sublimation purification apparatus, and purified by sublimation at 260 to 280° C./1 mmHg for three and a half hours. Thus, 0.88 g of a white solid was obtained (percentage yield: 88.0%).

Figure 16:
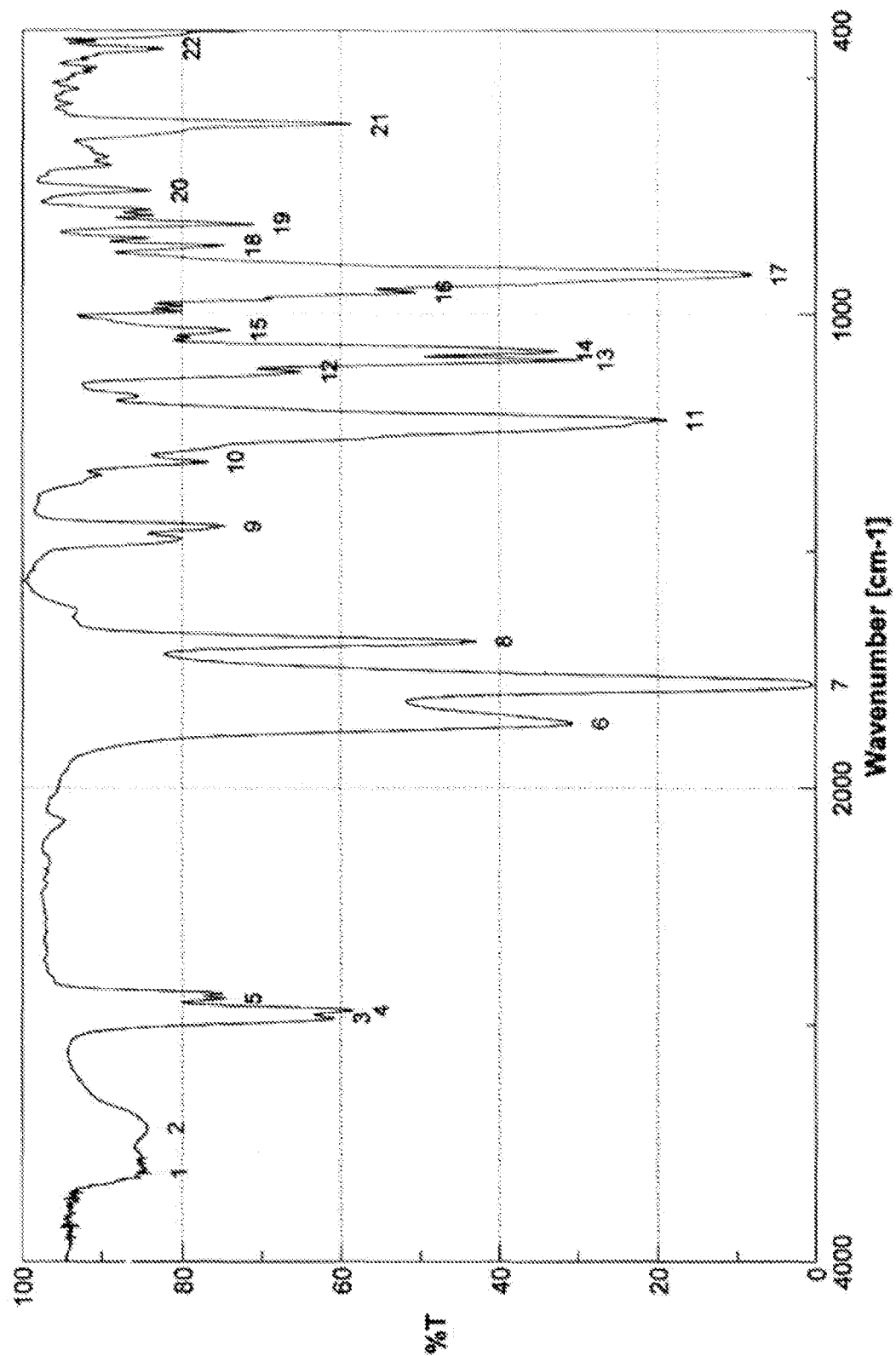
FIG. 16 is a graph showing an IR spectrum of norbornane-2-spiro-α-cyclohexanone-α'-spiro-2"-norbornane-5,5",6,6"-tetracarboxylic dianhydride obtained in Example 4.
Figure 17:
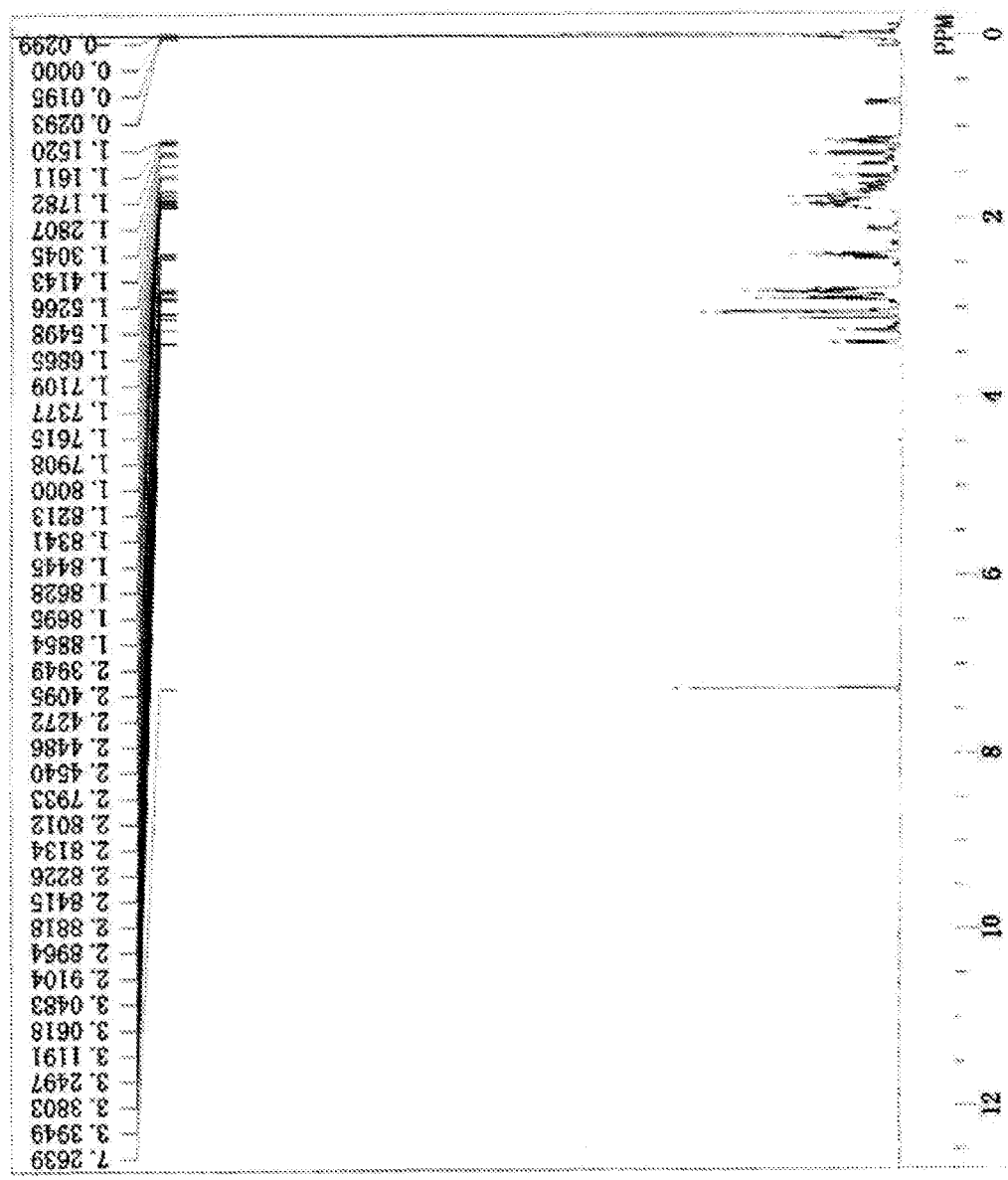
FIG. 17 is a graph showing a $^1$H-NMR (CDCl$_3$) spectrum of the norbornane-2-spiro-α-cyclohexanone-α'-spiro-2"-norbornane-5,5",6,6"-tetracarboxylic dianhydride obtained in Example 4.
Figure 18:
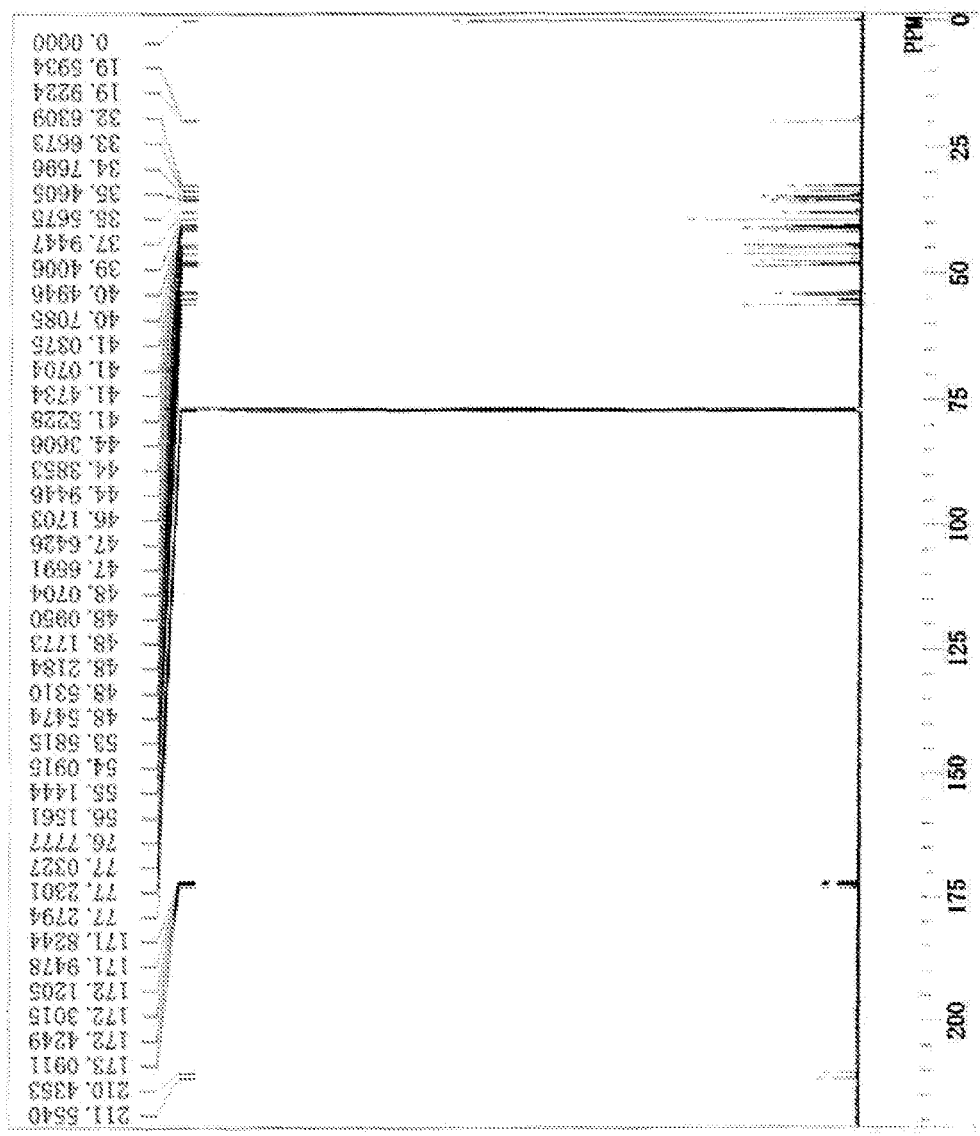
FIG. 18 is a graph showing a $^{13}$C-NMR (CDCl$_3$) spectrum of the norbornane-2-spiro-α-cyclohexanone-α'-spiro-2"-norbornane-5,5",6,6"-tetracarboxylic dianhydride obtained in Example 4.

To confirm the structure of the thus obtained compound, IR and NMR measurements were conducted. FIG. 16 shows an IR spectrum, FIG. 17 shows a $^1$H-NMR (CDCl$_3$) spectrum, and FIG. 18 shows a $^{13}$C-NMR (CDCl$_3$) spectrum. As is apparent from the results shown in FIGS. 16 to 18, the obtained compound was confirmed to be norbornane-2-spiro-α-cyclohexanone-α'-spiro-2"-norbornane-5,5",6,6"-tetracarboxylic dianhydride (also referred to as "norbornane-2-spiro-2'-cyclohexanone-6'-spiro-2?-norbornane-5,5",6,6"-tetracarboxylic dianhydride) represented by the following general formula (18):

[Chem. 29]

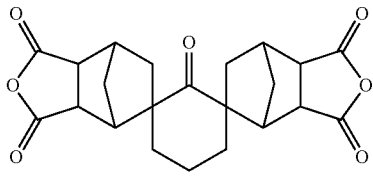

(18)

Example 5

Synthesis of Norbornane-2-spiro-α-cyclopentanone-α'-spiro-2"-norbornane-5,5",6,6"-tetracarboxylic acid by Transesterification Reaction A solution was obtained by introducing norbornane-2-spiro-α-cyclopentanone-α'-spiro-2"-norbornane-5,5",6,6"-tetracarboxylic acid tetramethyl ester (0.85 g, 1.78 mmol) and p-toluenesulfonic acid (42.7 mg, 0.13 mmol) into a 100-ml three-necked flask, and then further adding formic acid (30 ml), followed by mixing. Next, the obtained solution was refluxed at 120° C. for 11 hours. Subsequently, to remove methyl formate produced in the solution, the solution after reflux was concentrated to about a half amount by using an evaporator. Then, formic acid (10 ml) was added again, followed by reflux at 120° C. for 11 hours (concentration-reflux heating operation). Subsequently, such a concentration-reflux heating operation was repeated once again, and a reaction liquid was obtained. After that, the reaction liquid was concentrated to dryness by using an evaporator. Thus, a solid matter was obtained. The thus obtained solid matter was washed with diethyl ether, and a diethyl ether solution containing the insoluble matter was obtained. Then, the solid was recovered by filtering the solution. Next, the yield of the thus obtained solid after drying was 0.39 g (percentage yield: 55%). In addition, the diethyl ether solution used as a filtrate was concentrated by using an evaporator, and the obtained sol id was dried. As a result, the yield was 0.28 g (percentage yield: 39%). The total percentage yield obtained by adding this yield to the above-described yield was 94%.

Figure 19:
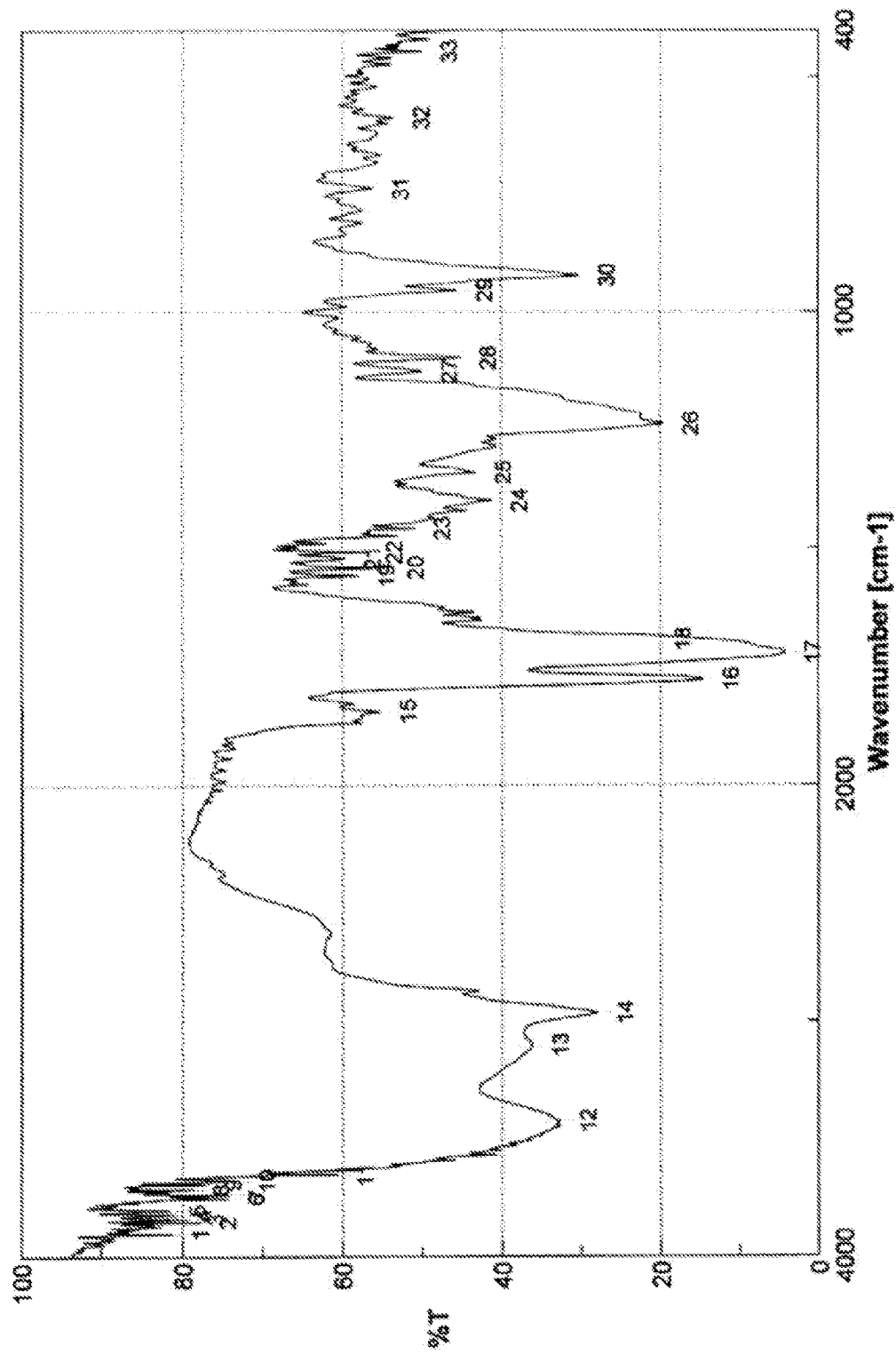
FIG. 19 is a graph showing an IR spectrum of norbornane-2-spiro-α-cyclopentanone-α'-spiro-2"-norbornane-5,5",6,6"-tetracarboxylic acid obtained in Example 5.
Figure 20:
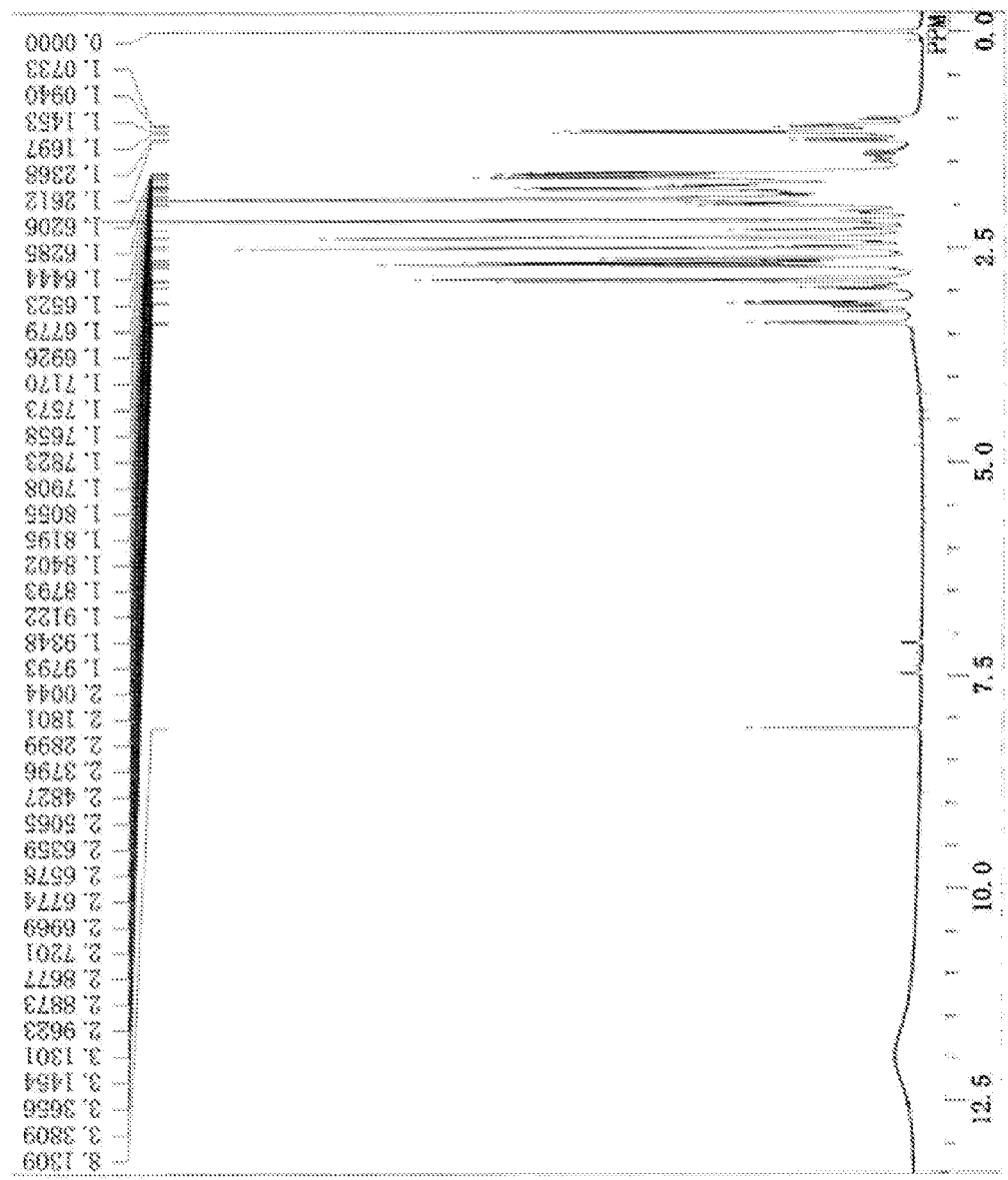
FIG. 20 is a graph showing a $^1$H-NMR (DMSO-d$^6$) spectrum of the norbornane-2-spiro-α-cyclopentanone-α'-spiro-2"-norbornane-5,5",6,6"-tetracarboxylic acid obtained in Example 5.
Figure 21:
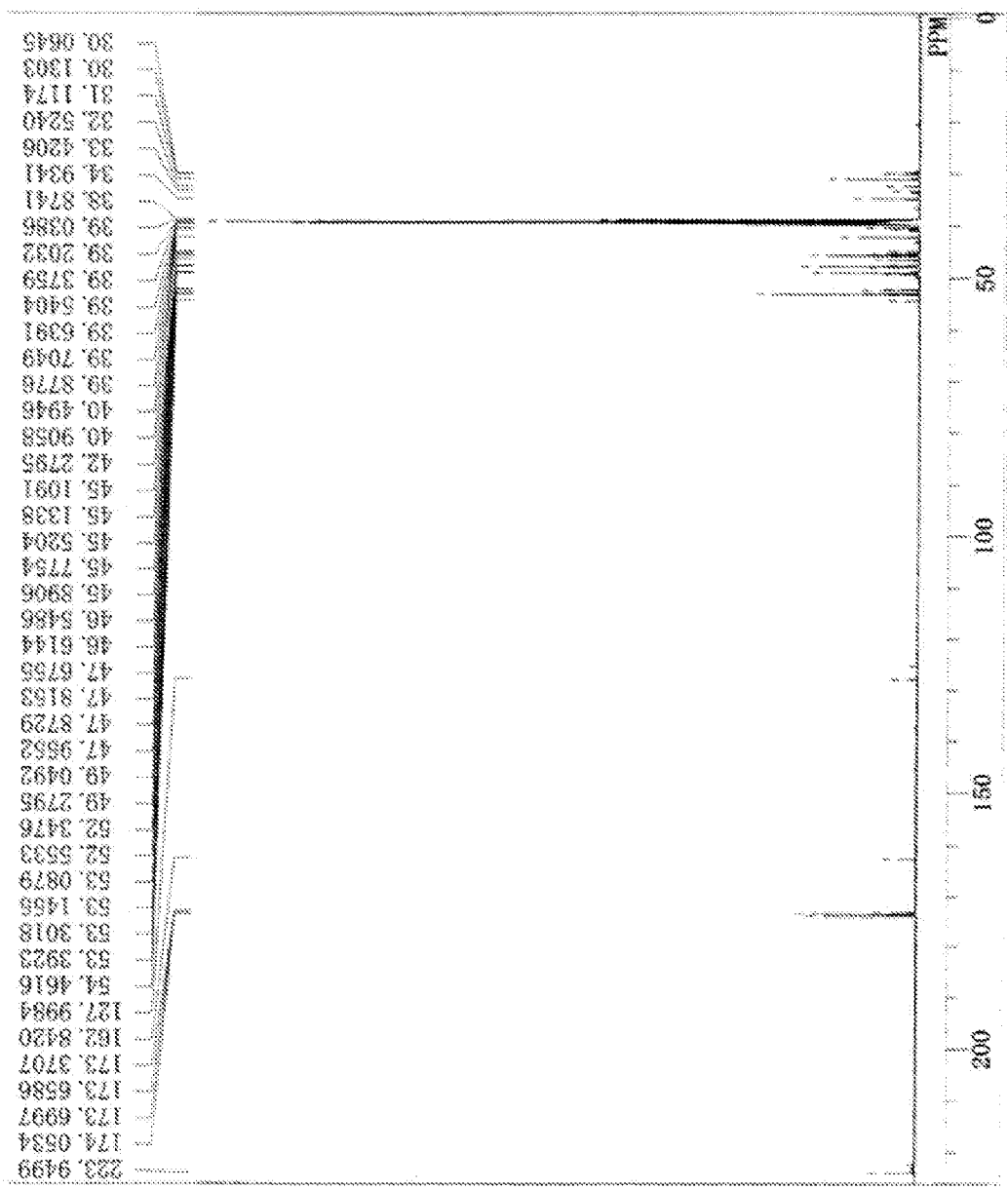
FIG. 21 is a graph showing a $^{13}$C-NMR (DMSO-d$^6$) spectrum of the norbornane-2-spiro-α-cyclopentanone-α'-spiro-2"-norbornane-5,5",6,6"-tetracarboxylic acid obtained in Example 5.

To confirm the structure of the thus obtained compound, IR and NMR measurements were conducted. FIG. 19 shows an IR spectrum of the diethyl ether insoluble portion of the obtained compound, FIG. 20 shows a $^1$H-NMR (DMSO-d$^6$) spectrum of the diethyl ether insoluble portion of the compound, and FIG. 21 shows a $^{13}$C-NMR (DMSO-d$^6$) spectrum of the diethyl ether insoluble portion of the compound. As a result of the IR measurement, the diethyl ether insoluble portion and the diethyl ether soluble portion showed substantially the same IR spectrums, and no difference was found. In addition, from the results shown in FIGS. 19 to 21, it was found that the obtained compound was norbornane-2-spiro-α-cyclopentanone-α'-spiro-2"-norbornane-5,5",6,6"-tetracarboxylic acid.

Example 6

Synthesis of Norbornane-2-spiro-α-cyclohexanone-α'-spiro-2"-norbornane-5,5",6,6"-tetracarboxylic Acid by Transesterification Reaction A solution was obtained by introducing norbornane-2-spiro-α-cyclohexanone-α'-spiro-2"-norbornane-5,5",6,6"-tetracarboxylic acid tetramethyl ester (3.3 g, 6.72 mmol) and p-toluenesulfonic acid (100 mg) into a 100-ml three-necked flask, and then further adding formic acid (25 ml), followed by mixing. Next, the obtained solution was refluxed at 120° C. for 6 hours. Subsequently, to remove methyl formate produced in the solution, the solution after reflux was concentrated to about a half amount by using an evaporator. Then, formic acid (10 ml) was added again, followed by reflux at 120° C. for 6 hours (concentration-reflux heating operation). Such a concentration-reflux heating operation was repeated once again, and a reaction liquid was obtained. After that, the reaction liquid was concentrated to dryness by using an evaporator. Thus, a solid matter was obtained. The thus obtained solid matter was washed with diethyl ether, and a diethyl ether solution containing the insoluble matter was obtained. Then, the solid was recovered by filtering the solution. The yield of the thus obtained solid after drying was 1.63 g (percentage yield: 55%). In addition, the diethyl ether solution used as a filtrate was concentrated by using an evaporator, and the obtained solid was dried. As a result, the yield was 1.13 g (percentage yield: 38%). The total percentage yield obtained by adding this yield to the above-described yield was 93%.

Figure 22:
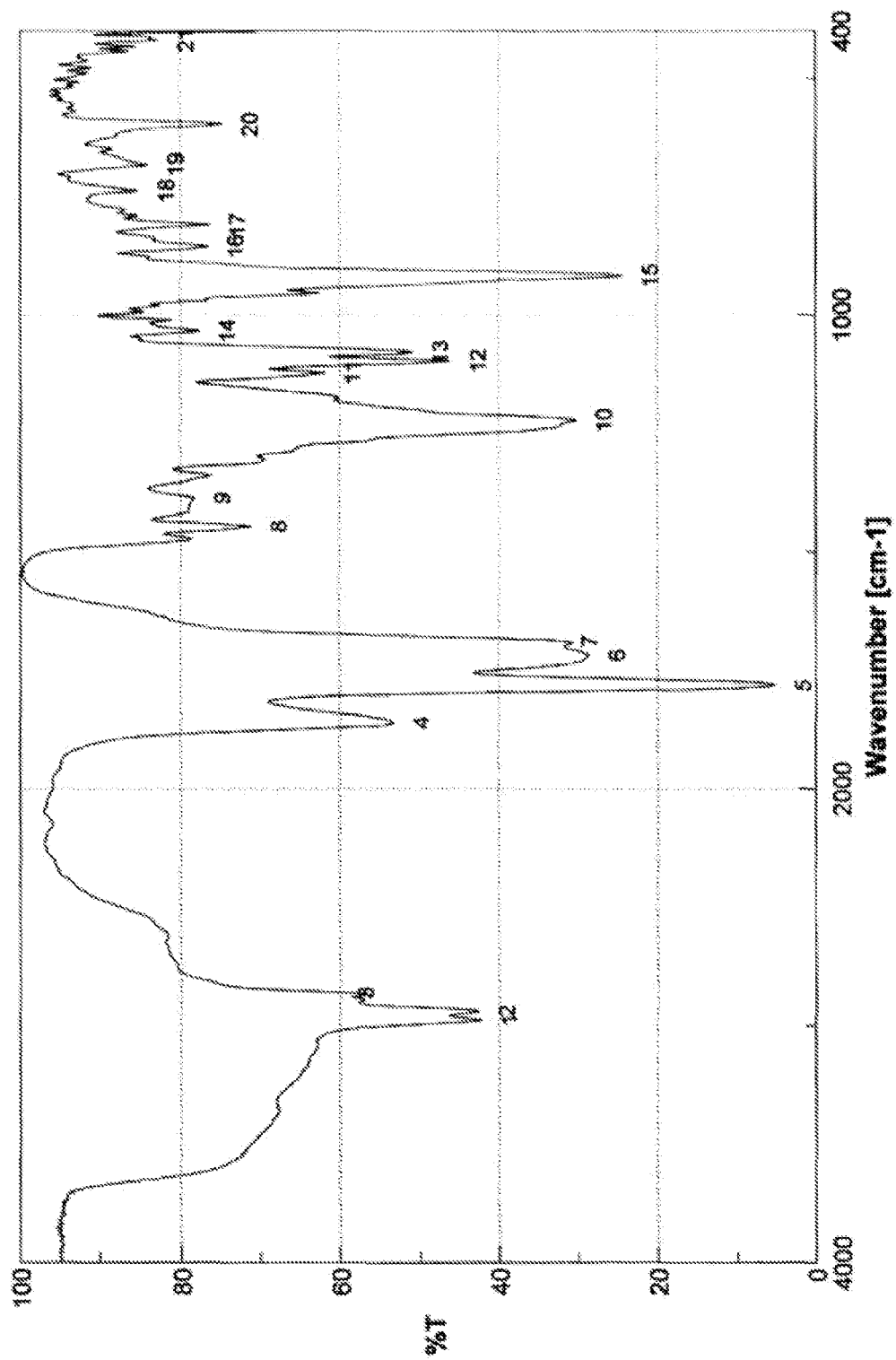
FIG. 22 is a graph showing an IR spectrum of norbornane-2-spiro-α-cyclohexanone-α'-spiro-2"-norbornane-5,5",6,6"-tetracarboxylic acid obtained in Example 6.
Figure 23:
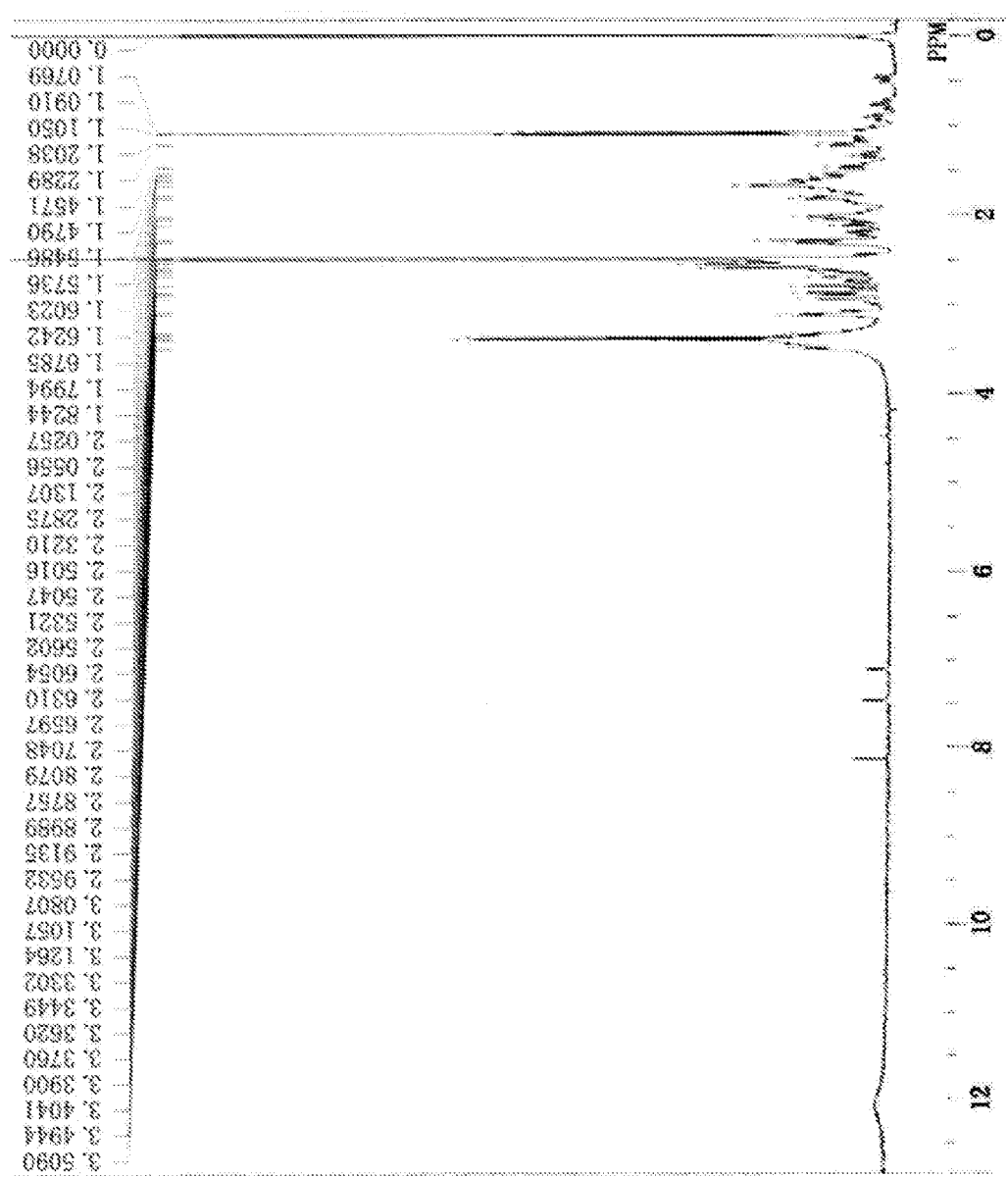
FIG. 23 is a graph showing a $^1$H-NMR (DMSO-d$^6$) spectrum of the norbornane-2-spiro-α-cyclohexanone-α'-spiro-2"-norbornane-5,5",6,6"-tetracarboxylic acid obtained in Example 6.
Figure 24:
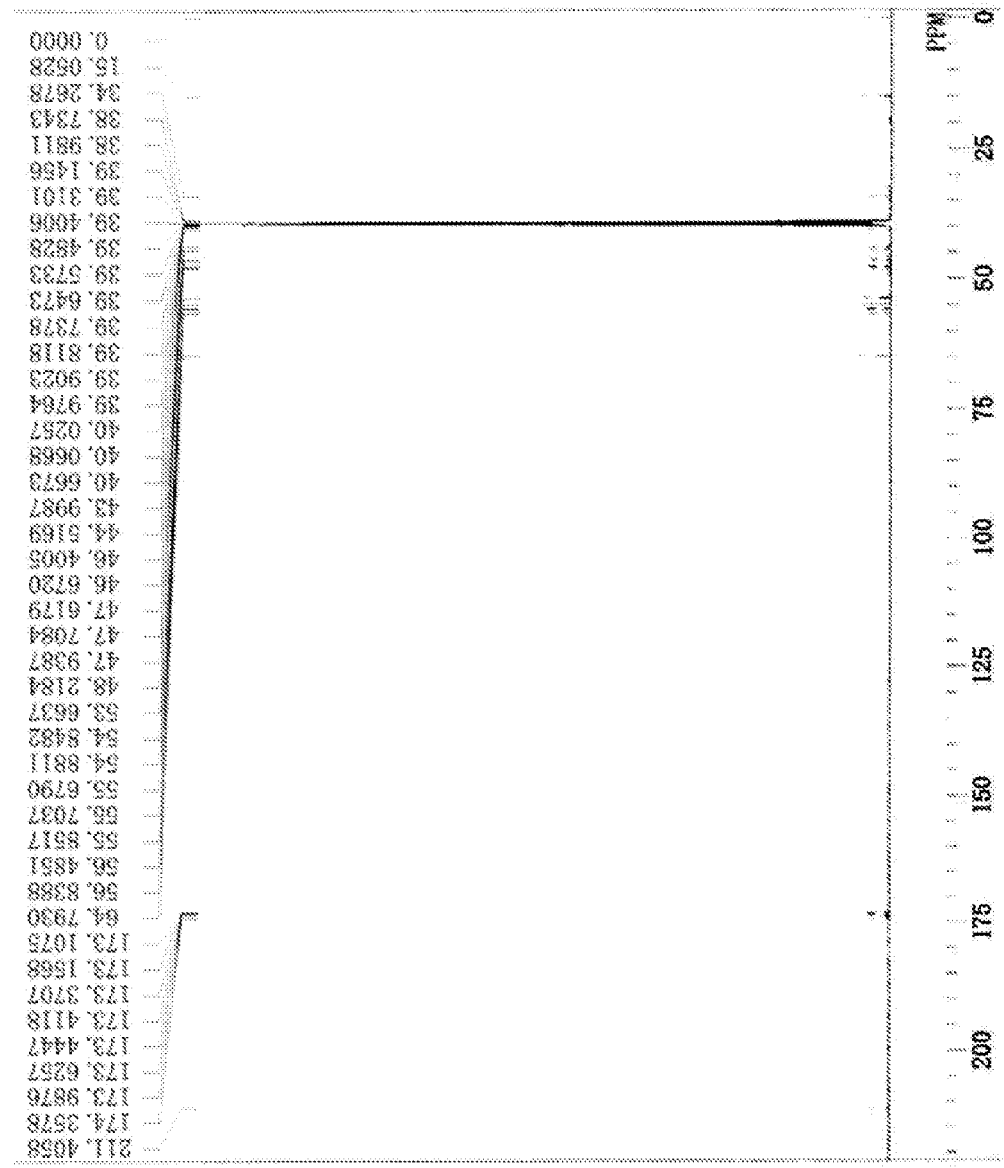
FIG. 24 is a graph showing a $^{13}$C-NMR (DMSO-d$^6$) spectrum of the norbornane-2-spiro-α-cyclohexanone-α'-spiro-2"-norbornane-5,5",6,6"-tetracarboxylic acid obtained in Example 6.

To confirm the structure of the thus obtained compound, IR and NMR measurements were conducted. FIG. 22 shows an IR spectrum of the diethyl ether insoluble portion of the thus obtained compound, FIG. 23 shows a $^1$H-NMR (DMSO-d$^6$) spectrum of the diethyl ether insoluble portion of the compound, and FIG. 24 shows a $^{13}$C-NMR (DMSO-d$^6$) spectrum of the diethyl ether insoluble portion of the compound. As a result of the IR measurement, the diethyl ether insoluble portion and the diethyl ether soluble portion showed substantially the same IR spectrums, and no difference was found. In addition, from the results shown in FIGS. 22 to 24, it was found that the obtained compound was norbornane-2-spiro-α-cyclohexanone-α'-spiro-2"-norbornane-5,5",6,6"-tetracarboxylic acid.

Example 7

Polyimide Preparation 1

A 30-ml three-necked flask was dried by heating with a heat gun. After that, the atmosphere inside the sufficiently dried three-necked flask was replaced with a nitrogen atmosphere, and 0.292 g (1.00 mmol) of 1,3-bis(4-aminophenoxy)benzene (solid) was introduced into the three-necked flask. Subsequently, 2.7 g of dimethylacetamide (N,N-dimethylacetamide) was added to the three-necked flask, and the solid was dissolved with stirring. Thus, a solution was obtained. Next, 0.384 g (1.00 mmol) of norbornane-2-spiro-α-cyclopentanone-α'-spiro-2"-norbornane-5,5",6,6"-tetracarboxylic dianhydride, which was the above-described compound obtained in Example 2, was added to the solution under a nitrogen atmosphere, followed by stirring under a nitrogen atmosphere at room temperature (25° C.) for 22 hours. Thus, a reaction liquid was obtained. Note that, by using the thus obtained reaction liquid (a dimethylacetamide solution of a polyamic acid), a dimethylacetamide solution having a polyamic acid concentration of 0.5 g/dL was prepared, and the intrinsic viscosity [η] of the polyamic acid was measured. As a result, the intrinsic viscosity [η] was 0.31 dL/g.

Subsequently, the reaction liquid was cast on a glass plate to form a coating on the glass plate. Then, the glass plate on which the coating was formed was introduced into an vacuum oven, and the coating was cured by heating under a pressure of 1 mmHg at 80° C. for 1 hour, 170° C. for 1 hour, and 250° C. for 1 hour, in this order. Thus, a film was formed on the glass plate. Then, the glass plate on which the film was formed was taken out of the vacuum oven, and the film was recovered from the glass plate by immersing the glass plate in hot water of 70° C.

Figure 25:
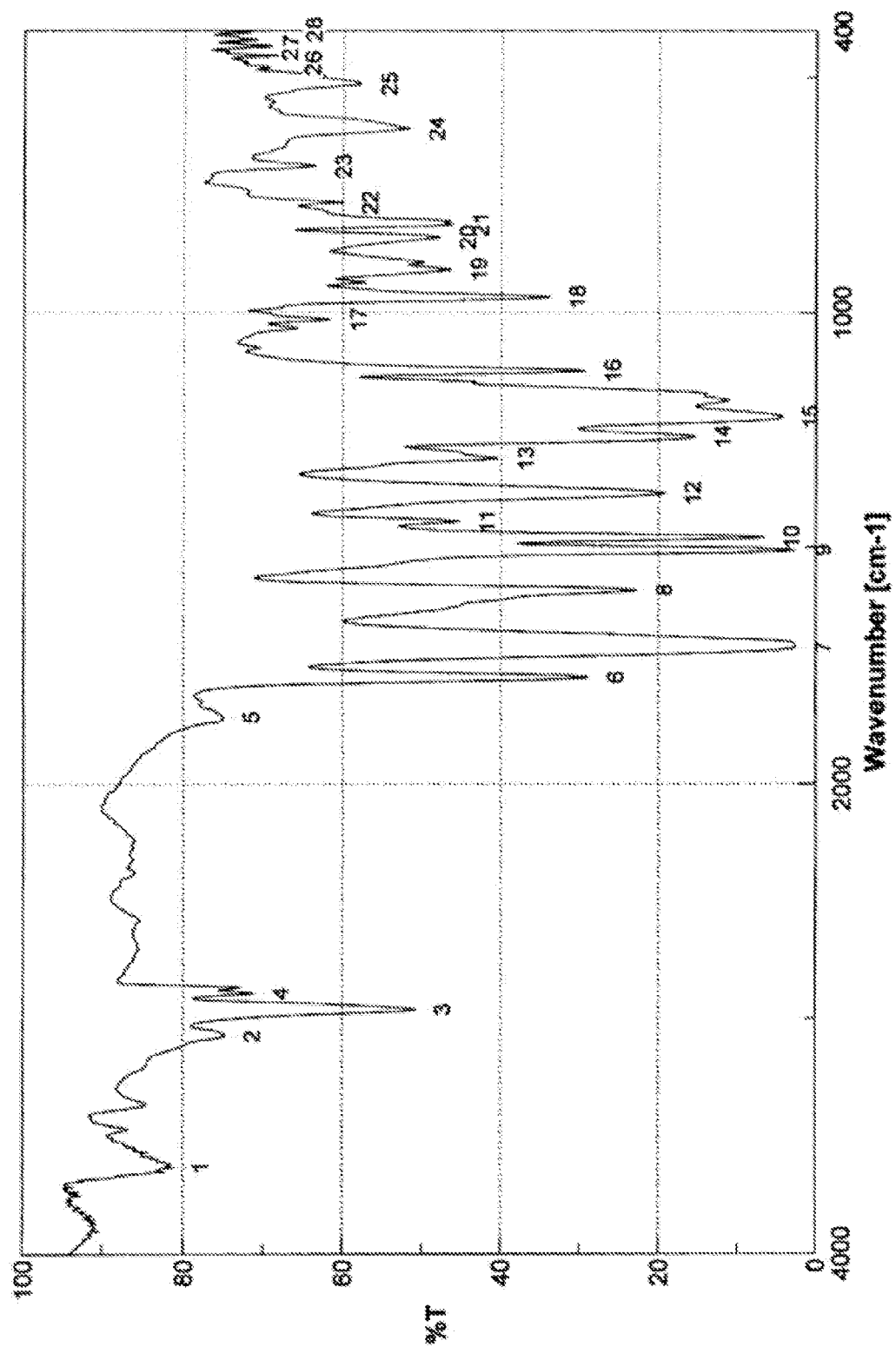
FIG. 25 is a graph showing an IR spectrum of a polyimide obtained in Example 7.

An IR spectrum of the thus obtained film was measured. FIG. 25 shows the IR spectrum of the obtained film. As is also apparent from the result shown in FIG. 25, C=O stretching vibration of imidocarbonyl was observed at 1777 and 1706 cm$^{-1}$, and hence the obtained film was confirmed to be made of a polyimide.

In addition, the 5% weight loss temperature of the thus obtained film-shaped polyimide was measured based on thermogravimetric analysis (TGA). As a result, the 5% weight loss temperature was 487° C. Moreover, differential scanning calorimetry (DSC) was conducted on the obtained polyimide. As a result, it was found that the glass transition temperature was 290° C. In addition, it was found that the thermal decomposition temperature (Td) of the polyimide was 497° C. In addition, the number average molecular weight (Mn) of the polyimide was 5,500 in terms of polystyrene, the weight average molecular weight (Mw) thereof was 7,000 in terms of polystyrene, and the molecular weight distribution (Mw/Mn) was 1.3. Moreover, the solubility of the thus obtained film made of the polyimide was checked. As a result, the thus obtained film was soluble in N-methyl-2-pyrrolidone, N,N-dimethylacetamide, 1,3-dimethyl-2-imidazolidinone, dimethyl sulfoxide, and m-cresol at room temperature (25° C.). From the results of the thermal analyses and the solubility test, it was found that the polyimide obtained in Example 7 was sufficiently soluble in organic solvents, and had a sufficient processability, and also that the polyimide obtained in Example 7 had a sufficiently high level of heat resistance.

Example 8

Polyimide Preparation 2

A 30-ml three-necked flask was dried by heating with a heat gun. After that, the atmosphere inside the sufficiently dried three-necked flask was replaced with a nitrogen atmosphere, and 0.292 g (1.00 mmol) of 1,3-bis(4-aminophenoxy)benzene (solid) was introduced into the three-necked flask. Subsequently, 2.7 g of dimethylacetamide was added into the three-necked flask, and the solid was dissolved with stirring. Thus, a solution was obtained. Next, 0.398 g (1.00 mmol) of norbornane-2-spiro-α-cyclohexanone-α'-spiro-2"-norbornane-5,5",6,6"-tetracarboxylic dianhydride, which was the above-described compound obtained in Example 4, was added to the solution under a nitrogen atmosphere, followed by stirring under a nitrogen atmosphere at room temperature (25° C.) for 22 hours. Thus, a reaction liquid was obtained. Note that, by using the thus obtained reaction liquid (a dimethylacetamide solution of a polyamic acid), a dimethylacetamide solution having a polyamic acid concentration of 0.5 g/dL was prepared, and the intrinsic viscosity [η] of the polyamic acid was measured. As a result, the intrinsic viscosity [η] was 0.30 dL/g.

Subsequently, the reaction liquid was cast on a glass plate to form a coating on the glass plate. Then, the glass plate on which the coating was formed was introduced into a vacuum oven, and the coating was cured by heating under a pressure of 1 mmHg at 80° C. for 1 hour, 170° C. for 1 hour, and 250° C. for 1 hour, in this order. Thus, a film was formed on the glass plate. Then, the glass plate on which the film was formed was taken out of the vacuum oven, and the film was recovered from the glass plate by immersing the glass plate in hot water of 70° C.

Figure 26:
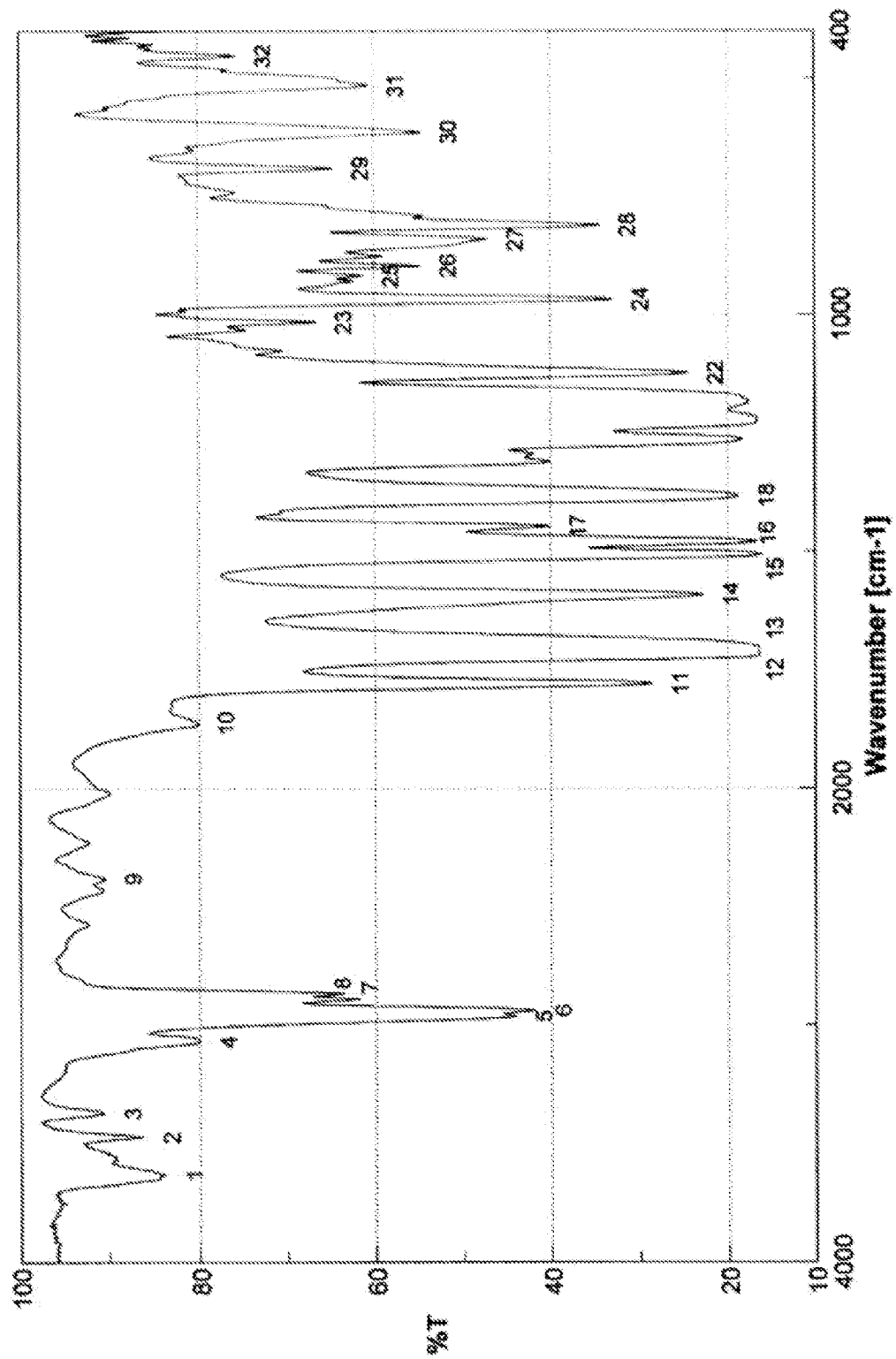
FIG. 26 is a graph showing an IR spectrum of a polyimide obtained in Example 8.

An IR spectrum of the thus obtained film was measured. FIG. 26 shows the IR spectrum of the obtained film. As is also apparent from the result shown in FIG. 26, C=O stretching vibration of imidocarbonyl was observed at 1779 and 1702 cm$^{-1}$, and hence the obtained film was confirmed to be made of a polyimide.

In addition, the 5% weight loss temperature of the thus obtained film-shaped polyimide was measured based on thermogravimetric analysis (TGA). As a result, the 5% weight loss temperature was 471° C. Moreover, differential scanning calorimetry (DSC) was conducted on the obtained polyimide. As a result, the glass transition temperature was 292° C. In addition, it was found that the thermal decomposition temperature (Td) of the polyimide was 483° C. In addition, the number average molecular weight (Mn) of the polyimide was 5,800 in terms of polystyrene, the weight average molecular weight (Mw) thereof was 8,400 in terms of polystyrene, and the molecular weight distribution (Mw/Mn) was 1.4. Moreover, the solubility of the thus obtained film made of the polyimide was checked. As a result, the thus obtained film was soluble in N-methyl-2-pyrrolidone, N,N-dimethylacetamide, 1,3-dimethyl-2-imidazolidinone, dimethyl sulfoxide, and m-cresol at room temperature (25° C.). From the results of the thermal analyses and the solubility test, it was found that the polyimide obtained in Example 8 was sufficiently soluble in organic solvents, and had a sufficient processability, and also that the polyimide obtained in Example 8 had a sufficiently high level of heat resistance.

Example 9

Polyimide Preparation 3

A 30-ml three-necked flask was dried by heating with a heat gun. Then, the atmosphere inside the sufficiently dried three-necked flask was replaced with a nitrogen atmosphere. First, 0.200 g (1.00 mmol) of 4,4'-diaminodiphenyl ether (solid) was introduced, then 2.7 g of N,N-dimethylacetamide was added, and the solid was dissolved with stirring. Thus, a solution was obtained. Subsequently, 0.384 g (1.00 mmol) of norbornane-2-spiro-α-cyclopentanone-α'-spiro-2"-norbornane-5,5",6,6"-tetracarboxylic dianhydride (also referred to as "norbornane-2-Spiro-2'-cyclopentanone-5'-spiro-2"-nor bornane-5,5",6,6"-tetracarboxylic dianhydride"), which was the above-described compound obtained in Example 2, was added to the solution under a nitrogen atmosphere, followed by stirring under a nitrogen atmosphere at room temperature (25° C.) for 22 hours. Thus, a reaction liquid was obtained. Note that, by using the thus obtained reaction liquid (a dimethylacetamide solution of a polyamic acid), a dimethylacetamide solution having a polyamic acid concentration of 0.5 g/dL was prepared, and the intrinsic viscosity [η] of the polyamic acid was measured. As a result, the intrinsic viscosity [η] was 0.35 dL/g.

Subsequently, the reaction liquid was cast on a glass plate to form a coating on the glass plate. Then, the glass plate on which the coating was formed was introduced into a vacuum oven, and the coating was cured by heating under a pressure of 1 mmHg at 80° C. for 1 hour, 170° C. for 1 hour, and 250° C. for 1 hour, in this order. Thus, a film was formed on the glass plate. Then, the glass plate on which the film was formed was taken out of the vacuum oven, and the film was recovered from the glass plate by immersing the glass plate in hot water of 70° C. Thus, a colorless transparent film made of a polyimide was obtained.

Figure 27:
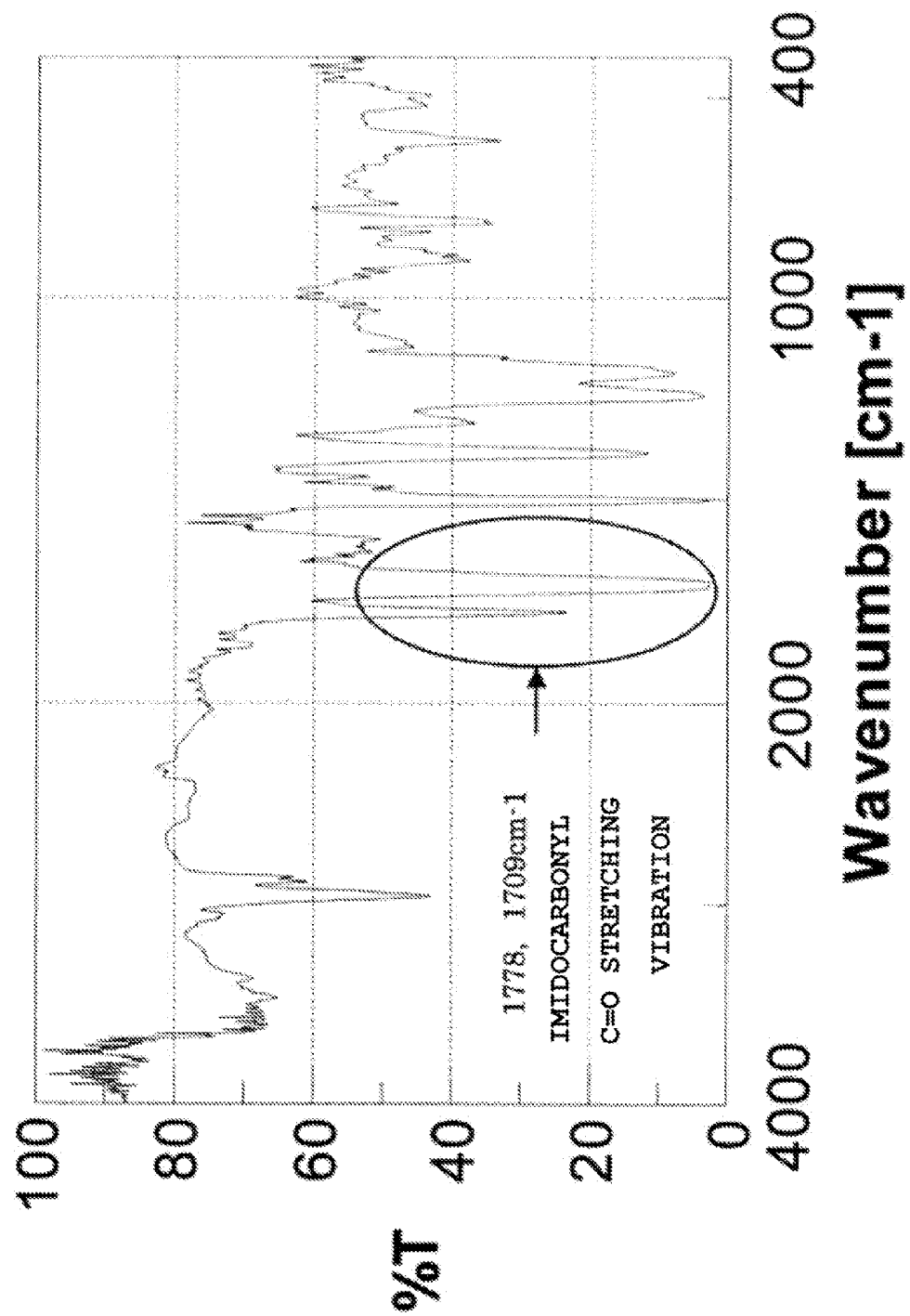
FIG. 27 is a graph showing an IR spectrum of a polyimide obtained in Example 9.

An IR spectrum of the thus obtained film was measured. FIG. 27 shows the IR spectrum of the obtained film. As is also apparent from the result shown in FIG. 27, C=O stretching vibration of imidocarbonyl was observed at 1778 and 1709 cm$^{-1}$, in the obtained film, and hence the obtained film was confirmed to be made of a polyimide.

The 5% weight loss temperature of the thus obtained film-shaped polyimide was measured based on thermogravimetric analysis (TGA). As a result, it was found that the 5% weight loss temperature in nitrogen was 468° C. Moreover, differential scanning calorimetry (DSC) was conducted on the obtained polyimide. As a result, no glass transition temperature Tg was observed from room temperature to 420° C., and it was found that the glass transition temperature Tg of the obtained polyimide exceeded 420° C. In addition, it was found that the thermal decomposition temperature (Td) of the polyimide was 489° C. In addition, the number average molecular weight (Mn) of the polyimide was 2,700 in terms of polystyrene, the weight average molecular weight (Mw) thereof was 3,600 in terms of polystyrene, and the molecular weight distribution (Mw/Mn) was 1.3. Moreover, the solubility of the thus obtained film made of the polyimide was checked. As a result, it was found that the thus obtained film was soluble in N-methyl-2-pyrrolidone, N,N-dimethylacetamide, 1,3-dimethyl-2-imidazolidinone, dimethyl sulfoxide, and m-cresol at room temperature (25° C.). From the results of the thermal analyses and the solubility test, it was found that the polyimide obtained in Example 9 was sufficiently soluble in organic solvents and had a sufficient processability, and also that the polyimide obtained in Example 9 had a sufficiently high level of heat resistance.

Example 10

Polyimide Preparation 4

A 30-ml three-necked flask was dried by heating with a heat gun. Then, the atmosphere inside the sufficiently dried three-necked flask was replaced with a nitrogen atmosphere. First, 0.200 g (1.00 mmol) of 4,4'-diaminodiphenyl ether (solid) was introduced, then 2.7 g of N,N-dimethylacetamide was added, and the solid was dissolved with stirring. Thus, a solution was obtained. Subsequently, 0.398 g (1.00 mmol) of norbornane-2-spiro-α-cyclohexanone-α'-spiro-2"-norbornane-5,5",6,6"-tetracarboxylic dianhydride (also referred to as "norbornane-2-spiro-2'-cyclohexanone-6'-spiro-2"-norbornane-5,5",6,6"-tetracarboxylic dianhydride"), which was the above-described compound obtained in Example 4, was added to the solution, under a nitrogen atmosphere, followed by stirring under a nitrogen atmosphere at room temperature (25° C.) for 22 hours. Thus, a reaction liquid was obtained. Note that, by using the thus obtained reaction liquid (a dimethylacetamide solution of a polyamic acid), a dimethylacetamide solution having a polyamic acid concentration of 0.5 g/dL was prepared, and the intrinsic viscosity [η] of the polyamic acid was measured. As a result, the intrinsic viscosity [η] was 0.34 dL/g.

Subsequently, the reaction liquid was cast on a glass plate to form a coating on the glass plate. Then, the glass plate on which the coating was formed was introduced into a vacuum oven, and the coating was cured by heating under a pressure of 1 mmHg at 80° C. for 1 hour, 170° C. for 1 hour, and 250° C. for 1 hour, in this order. Thus, a film was formed on the glass plate. Then, the glass plate on which the film was formed was taken out of the vacuum oven, and the film was recovered from the glass plate by immersing the glass plate in hot water of 70° C. Thus, a colorless transparent film made of a polyimide was obtained.

An IR spectrum of the thus obtained film was measured. As a result, C=O stretching vibration of imidocarbonyl was observed at 1779 and 1702 cm$^{-1}$, and hence the obtained film was confirmed to be made of a polyimide. The 5% weight loss temperature of the thus obtained film-shaped polyimide was measured based on thermogravimetric analysis (TGA). As a result, it was found that the 5% weight loss temperature in nitrogen was 489° C. Moreover, differential scanning calorimetry (DSC) was conducted on the obtained polyimide. As a result, no glass transition temperature Tg was observed from room temperature to 420° C., and it was found that the glass transition temperature Tg of the obtained polyimide exceeded 420° C. In addition, it was found that the thermal decomposition temperature (Td) of the polyimide was 499° C. In addition, the number average molecular weight (Mn) of the polyimide was 3,000 in terms of polystyrene, the weight average molecular weight (Mw) thereof was 4,200 in terms of polystyrene, and the molecular weight distribution (Mw/Mn) was 1.4. Moreover, the solubility of the thus obtained film made of the polyimide was checked. As a result, it was found that the thus obtained film was soluble in N-methyl-2-pyrrolidone, N,N-dimethylacetamide, 1,3-dimethyl-2-imidazolidinone, dimethyl sulfoxide, and m-cresol at room temperature (25° C.). From the results of the thermal analyses and the solubility test, it was found that the polyimide obtained in Example 10 was sufficiently soluble in organic solvents and had a sufficient processability, and also that the polyimide obtained in Example 10 had a sufficiently high level of heat resistance.

Comparative Example 1

Polyimide Preparation for Comparison

A polyimide film for comparison was obtained in the same manner as in Example 7, except that bicyclo[2.2.1]heptane-2,3,5-tricarboxyl-5-acetic 2,3:5,5-dianhydride (0.250 g, 1.00 mmol), which is a monospiro acid dianhydride described in Japanese Unexamined Patent Application Publication No. Hei 10-310640, and which is represented by the following general formula (19), was used instead of norbornane-2-spiro-α-cyclopentanone-α'-spiro-2"-norbornane-5,5",6,6"-tetracarboxylic dianhydride, which was the above-described compound obtained in Example 2:

[Chem. 30]

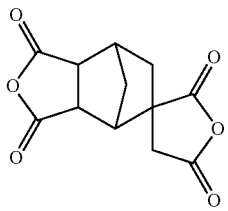

(19)

The 5% weight loss temperature of the thus obtained polyimide film was measured based on thermogravimetric analysis (TGA). As a result, the 5% weight loss temperature was 465° C. Moreover, differential scanning calorimetry (DSC) was conducted on the obtained polyimide. As a result, the glass transition temperature was 227° C.

Evaluation of Polyimides Obtained in Examples 7 and 8 and Comparative Example 1

As is also apparent from the above-described results of Examples 7 and 8 and Comparative Example 1, it was found that, in each of the cases (Examples 7 and 8) where the norbornane-2-spiro-α-cycloalkanone-α'-spiro-2"-norbornane-5,5",6,6"-tetracarboxylic dianhydrides obtained in Examples 2 and 4 were used, the polyimide was sufficiently soluble in the organic solvent, and hence had a high level of processability during the production of the film. In addition, it was found that, in each of the cases (Examples 7 and 8) where polyimides were prepared by using the norbornane-2-spiro-α-cycloalkanone-α'-spiro-2"-norbornane-5,5",6,6"-tetracarboxylic dianhydrides obtained in Examples 2 and 4, the obtained polyimide had a glass transition temperature which was higher by 63 to 65° C. than that of the polyimide obtained in Comparative Example 1. In addition, of conventional alicyclic polyimides using 1,3-bis(4-aminophenoxy)benzene, the alicyclic polyimide having a glass transition temperature (Tg) of 256° C. described in "Macromolecules" published in 1994, vol. 27, p. 1117 has been known as an alicyclic polyimide having the highest Tg. However, it was found that the alicyclic polyimides (Examples 7 and 8) prepared by using the norbornane-2-spiro-α-cycloalkanone-α'-spiro-2"-norbornane-5,5",6,6"-tetracarboxylic dianhydrides of the present invention (Examples 2 and 4) had Tgs of 290° C. and 292° C., respectively, and that the alicyclic polyimides (Examples 7 and 8) had extremely higher glass transition temperatures than conventional alicyclic polyimides using 1,3-bis(4-aminophenoxy)benzene.

[Industrial Applicability]

As described above, according to the present invention, it is possible to provide a norbornane-2-spiro-α-cycloalkanone-α'-spiro-2"-norbornane-5,5",6,6"-tetracarboxylic dianhydride which can be used as a raw material monomer for producing a polyimide having a high light transmittance, a sufficiently excellent solubility in a solvent, and further a sufficiently high level of heat resistance; a norbornane-2-spiro-α-cycloalkanone-α'-spiro-2"-norbornane-5,5",6,6"-tetracarboxylic acid and an ester thereof which are obtained as intermediates thereof; and a method for producing a norbornane-2-spiro-α-cycloalkanone-α'-spiro-2"-norbornane-5,5",6,6"-tetracarboxylic dianhydride, the method being capable of efficiently and reliably producing a norbornane-2-spiro-α-cycloalkanone-α'-spiro-2"-norbornane-5,5",6,6"-tetracarboxylic dianhydride.

In addition, according to the present invention, it is possible to provide a polyimide which can have a high light transmittance and a sufficiently high level of heat resistance, and a method for producing a polyimide capable of efficiently and reliably producing the polyimide.

Accordingly, although being an aliphatic tetracarboxylic dianhydride, the norbornane-2-spiro-α-cycloalkanone-α'-spiro-2"-norbornane-5,5",6,6"-tetracarboxylic dianhydride of the present invention had a sufficiently high level of heat resistance. Hence, the norbornane-2-spiro-α-cycloalkanone-α'-spiro-2"-norbornane-5,5",6,6"-tetracarboxylic dianhydride of the present invention is particularly useful as a material (raw material monomer) for producing polyimides for flexible printed wiring boards, polyimides for heat resistant insulating tapes, polyimides for enamels for wires, polyimides for protective coatings of semiconductors, polyimides for liquid crystal orientation films, polyimides for transparent electrode substrates of organic ELs, polyimides for transparent electrode substrates of solar cells, polyimides for transparent electrode substrates of electronic papers, materials for substrates of various gas-barrier films, and the like; and as the like.

Moreover, although being an alicyclic polyimide, the polyimide of the present invention can have a sufficiently high level of heat resistance with a glass transition temperature comparable to those of wholly aromatic polyimides (for example, trade name "Kapton," glass transition temperature: 410° C.). In addition, the polyimide of the present invention is soluble in a solvent and has a high processability, and hence is, for example, particularly useful as a raw material for producing polyimides for flexible printed wiring boards, polyimides for heat resistant insulating tapes, polyimides for enamels for wires, polyimides for protective coatings of semiconductors, polyimides for liquid crystal orientation films, polyimides for transparent electrode substrates of organic ELs, polyimides for transparent electrode substrates of solar cells, polyimides for transparent electrode substrates of electronic papers, materials for substrates of various gas-barrier films, polyimides for transfer belts, polyimides for interlayer dielectric films, polyimides for substrates for sensors and the like, where an extremely high level of heat resistance is required; and as the like.

The invention claimed is:

1. A norbornane-2-spiro-α-cycloalkanone-α'-spiro-2"-norbornane-5,5",6,6"-tetracarboxylic dianhydride represented by the following general formula (1):

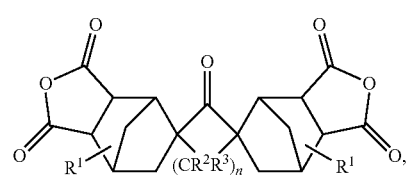

(1)

wherein, in the formula (1), $R^1$s, $R^2$, and $R^3$ each independently represent one selected from the group consisting of a hydrogen atom, alkyl groups having 1 to 10 carbon atoms, and a fluorine atom, and n represents an integer of 0 to 12.

2. A norbornane-2-spiro-α-cycloalkanone-α'-spiro-2"-norbornane-5,5",6,6"-tetracarboxylic acid and an ester thereof represented by the following general formula (2):

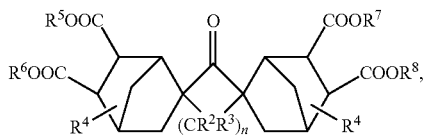

wherein, in the formula (2), $R^2$, $R^3$, and $R^4$s each independently represent one selected from the group consisting of a hydrogen atom, alkyl groups having 1 to 10 carbon atoms, and a fluorine atom, $R^5$, $R^6$, $R^7$, and $R^8$ each independently represent one selected from the group consisting of a hydrogen atom, alkyl groups having 1 to 10 carbon atoms, cycloalkyl groups having 3 to 10 carbon atoms, alkenyl groups having 2 to 10 carbon atoms, aryl groups having 6 to 20 carbon atoms, and aralkyl groups having 7 to 20 carbon atoms, and n represents an integer of 0 to 12.

3. A method for producing a norbornane-2-spiro-α-cycloalkanone-α'-spiro-2"-norbornane-5,5",6,6"-tetracarboxylic dianhydride, comprising:

a step of reacting a 5-norbornene-2-spiro-α-cycloalkanone-α'-spiro-2"-5"-norbornene with an alcohol and carbon monoxide in the presence of a palladium catalyst and an oxidizing agent, to thereby obtain at least one compound of norbornane-2-spiro-α-cycloalkanone-α'-spiro-2"-norbornane-5,5",6,6"-tetracarboxylic acids and esters thereof, the 5-norbornene-2-spiro-α-cycloalkanone-α'-spiro-2"-5"-norbornene being represented by the following general formula (3):

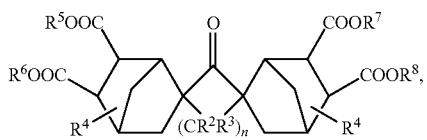

wherein, in the formula (3), $R^2$, $R^3$, and $R^9$s each independently represent one selected from the group consisting of a hydrogen atom, alkyl groups having 1 to 10 carbon atoms, and a fluorine atom, and n represents an integer of 0 to 12, the norbornane-2-spiro-α-cycloalkanone-α'-spiro-2"-norbornane-5,5",6,6"-tetracarboxylic acids and esters thereof is represented by the following general formula (2):

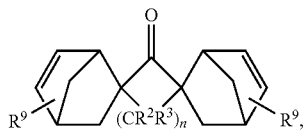

wherein the formula (2), $R^2$, $R^3$, and $R^4$s each independently represent one selected from the group consisting of a hydrogen atom, alkyl groups having 1 to 10 carbon atoms, and a fluorine atom, $R^5$, $R^6$, $R^7$, and $R^8$ each independently represent one selected from the group consisting of a hydrogen atom, alkyl groups having 1 to 10 carbon atoms, cycloalkyl groups having 3 to 10 carbon atoms, alkenyl groups having 2 to 10 carbon atoms, aryl groups having 6 to 20 carbon atoms, and aralkyl groups having 7 to 20 carbon atoms, and n represents an integer of 0 to 12; and a step of obtaining a norbornane-2-spiro-α-cycloalkanone-α'-spiro-2"-norbornane-5,5",6,6"-tetracarboxylic dianhydride according to claim 1 from the compound by using formic acid, an acid catalyst, and acetic anhydride, the norbornane-2-spiro-α-cycloalkanone-α'-spiro-2"-norbornane-5,5",6,6"-tetracarboxylic dianhydride is represented by the following general formula (1):

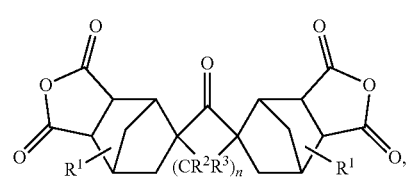

wherein the formula (1), $R^1$s, $R^2$, and $R^3$ each independently represent one selected from the group consisting of a hydrogen atom, alkyl groups having 1 to 10 carbon atoms, and a fluorine atom, and n represents an integer of 0 to 12.

4. A polyimide having a repeating unit represented by the following general formula (4):

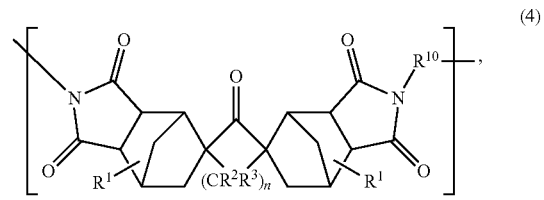

wherein, in the formula (4), $R^1$s, $R^2$, and $R^3$ each independently represent one selected from the group consisting of a hydrogen atom, alkyl groups having 1 to 10 carbon atoms, and a fluorine atom, $R^{10}$ represents an aryl group having 6 to 40 carbon atoms, and n represents an integer of 0 to 12.

5. The polyimide according to claim 4, wherein $R^{10}$ in the general formula (4) is at least one of groups represented by the following general formula (5) to (8):

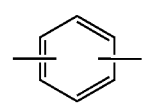

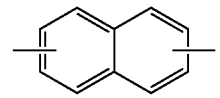

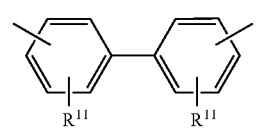

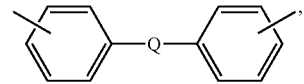

wherein, in the formula (7), $R^{11}$s represent one selected from the group consisting of a hydrogen atom, a fluorine atom, a methyl group, an ethyl group, and a trifluoromethyl group, and in the formula (8), Q represents one selected from the group consisting of groups represented by the formulae: —O—, —S—, —CO—, —CONH—, —SO$_2$—, —C(CF$_3$)$_2$—, —C(CH$_3$)$_2$—, —CH$_2$—, —O—C$_6$H$_4$—C(CH$_3$)$_2$—C$_6$H$_4$—O—, —O—C$_6$H$_4$—SO$_2$—C$_6$H$_4$—O—, —C(CH$_3$)$_2$—C$_6$H$_4$—C(CH$_3$)$_2$—, —O—C$_6$H$_4$—C$_6$H$_4$—O—, and —O—C$_6$H$_4$—O—.

6. A polyamic acid having a repeating unit represented by the following general formula (9):

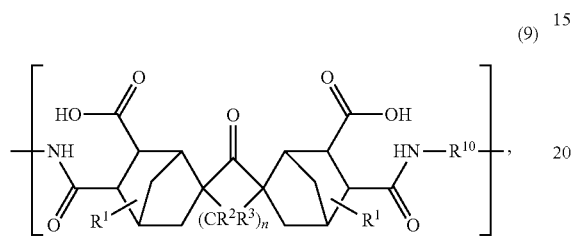
(9)

wherein, in the formula (9), $R^1$s, $R^2$, and $R^3$ each independently represent one selected from the group consisting of a hydrogen atom, alkyl groups having 1 to 10 carbon atoms, and a fluorine atom, $R^{10}$ represents an aryl group having 6 to 40 carbon atoms, and n represents an integer of 0 to 12.

7. The polyamic acid according to claim 6, wherein $R^{10}$ in the general formula (9) is at least one of groups represented by the following general formulae (5) to (8):

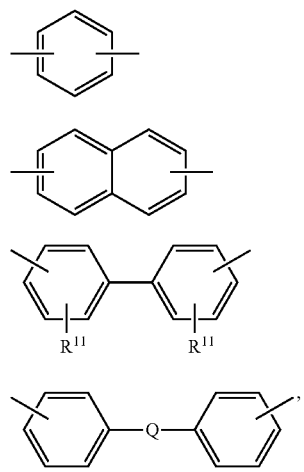
(5)
(6)
(7)
(8)

wherein, in the formula (7), $R^{11}$s represent one selected from the group consisting of a hydrogen atom, a fluorine atom, a methyl group, an ethyl group, and a trifluoromethyl group, and in the formula (8), Q represents one selected from the group consisting of groups represented by the formulae: —O—, —S—, —CO—, —CONH—, —SO$_2$—, —C(CF$_3$)$_2$—, —C(CH$_3$)$_2$—, —CH$_2$—, —O—C$_6$H$_4$—C(CH$_3$)$_2$—C$_6$H$_4$—O—, —O—C$_6$H$_4$—SO$_2$—C$_6$H$_4$—O—, —C(CH$_3$)$_2$—C$_6$H$_4$—C(CH$_3$)$_2$—, —O—C$_6$H$_4$—C$_6$H$_4$—O—, and —O—C$_6$H$_4$—O—.

8. The polyamic acid according to claim 6, wherein the polyamic acid has an intrinsic viscosity [η] of 0.05 to 3.0 dL/g, the intrinsic viscosity [η] being measured with a kinematic viscometer under a temperature condition of 30° C. by using a solution of the polyamic acid at a concentration of 0.5 g/dL obtained by dissolving the polyamic acid in N,N-dimethylacetamide.

9. A method for producing a polyimide, comprising:
a step of reacting a norbornane-2-spiro-α-cycloalkanone-α'-spiro-2"-norbornane-5,5",6,6"-tetracarboxylic dianhydride with an aromatic diamine in the presence of an organic solvent, to thereby obtain a polyamic acid,
the norbornane-2-spiro-α-cycloalkanone-α'-spiro-2"-norbornane-5,5",6,6"-tetracarboxylic dianhydride being represented by the following general formula (1):

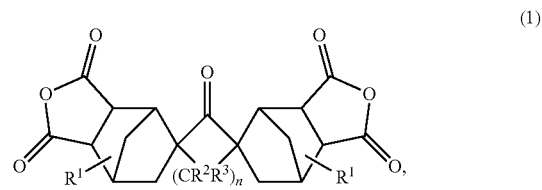
(1)

wherein the formula (1), $R^1$s, $R^2$, and $R^3$ each independently represent one selected from the group consisting of a hydrogen atom, alkyl groups having 1 to 10 carbon atoms, and a fluorine atom, and n represents an integer of 0 to 12,
the aromatic diamine being represented by the following general formula (10):

$$H_2N—R^{10}—NH_2 \quad (10)$$

wherein, in the formula (10), $R^{10}$ represents an aryl group having 6 to 40 carbon atoms,
the polyamic acid having a repeating unit is represented by the following general formula (9):

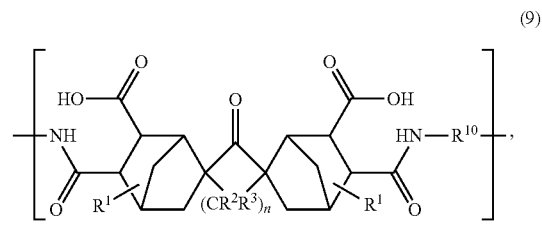
(9)

wherein, in the formula (9), $R^1$s, $R^2$, and $R^3$ each independently represent one selected from the group consisting of a hydrogen atom, alkyl groups having 1 to 10 carbon atoms, and a fluorine atom, $R^{10}$ represents an aryl group having 6 to 40 carbon atoms, and n represents an integer of 0 to 12; and
a step of subjecting the polyamic acid to imidization, to thereby obtain the polyimide according to claim 4, the polymide having a repeating unit represented by the following general formula (4):

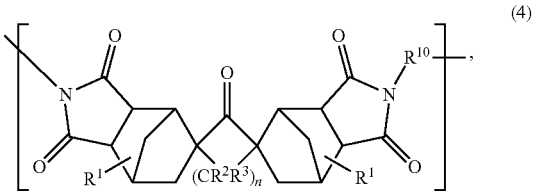
(4)

wherein the formula, $R^1$s, $R^2$, and $R^3$ each independently represent one selected from the group consisting of a hydrogen atom, alkyl groups having 1 to 10 carbon atoms, and a fluorine atom, $R^{10}$ represents an aryl group having 6 to 40 carbon atoms, and n represents an integer of 0 to 12.

10. A film comprising the polyimide according to claim 4.

11. A flexible printed wiring board comprising the polyimide according to claim 4.

12. A liquid crystal orientation film comprising the polyimide according to claim 4.

13. A transparent electrode substrate of an organic EL, comprising the polyimide according to claim 4.

14. A transparent electrode substrate of a solar cell, comprising the polyimide according to claim 4.

15. A transparent electrode substrate of an electronic paper, comprising the polyimide according to claim 4.

16. A heat resistant insulating tape comprising the polyimide according to claim 4.

17. An enamel for a wire, comprising the polyimide according to claim 4.

18. A protective coating of a semiconductor, comprising the polyimide according to claim 4.

19. A solution comprising the polyamic acid according to claim 6, and an organic solvent.

* * * * *